(12) United States Patent
Shughrue et al.

(10) Patent No.: US 10,442,855 B2
(45) Date of Patent: Oct. 15, 2019

(54) ANTIBODIES RECOGNIZING MEDIN

(71) Applicant: PROTHENA BIOSCIENCES LIMITED, Dublin (IE)

(72) Inventors: Paul Joseph Shughrue, Burlingame, CA (US); Tarlochan S. Nijjar, Orinda, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

(21) Appl. No.: 15/199,236

(22) Filed: Jun. 30, 2016

(65) Prior Publication Data
US 2017/0121397 A1 May 4, 2017

Related U.S. Application Data

(63) Continuation-in-part of application No. 15/004,854, filed on Jan. 22, 2016, now abandoned.

(60) Provisional application No. 62/106,690, filed on Jan. 22, 2015.

(51) Int. Cl.
| C07K 16/18 | (2006.01) |
|---|---|
| C07K 16/00 | (2006.01) |
| A61K 49/00 | (2006.01) |
| C07K 16/30 | (2006.01) |

(52) U.S. Cl.
CPC .......... *C07K 16/18* (2013.01); *A61K 49/0004* (2013.01); *C07K 16/3015* (2013.01); *C07K 2317/24* (2013.01); *C07K 2317/34* (2013.01); *C07K 2317/565* (2013.01); *C07K 2317/567* (2013.01); *C07K 2317/92* (2013.01); *G01N 2800/329* (2013.01); *G01N 2800/7047* (2013.01)

(58) Field of Classification Search
None
See application file for complete search history.

(56) References Cited

U.S. PATENT DOCUMENTS

2016/0251417 A1    9/2016  Shughrue et al.

FOREIGN PATENT DOCUMENTS

WO    WO 2016/118930 A1    7/2016

OTHER PUBLICATIONS

Paul, Fundamental Immunology, (textbook), 1993, pp. 292-295, under the heading "Fv Structure and Diversity in Three Dimensions".*
Rudikoff et al., Single amino acid substitution altering antigen-binding specificity.Proc Natl Acad Sci U S A. Mar. 1982; 79(6):1979-1983.*

(Continued)

*Primary Examiner* — Kimberly Ballard
*Assistant Examiner* — Aurora M Fontainhas
(74) *Attorney, Agent, or Firm* — Alston & Bird LLP

(57) ABSTRACT

The invention provides antibodies that specifically bind to medin. The antibodies have the capacity to bind to monomeric, misfolded, aggregated, fibril or deposited forms of medin. The antibodies can be used for treating or effecting prophylaxis of diseases associated with medin, medin accumulation or accumulation of medin deposits (e.g., medin amyloidosis). The antibodies can also be used for diagnosing medin amyloidosis and inhibiting or reducing aggregation of medin, among other applications.

33 Claims, 26 Drawing Sheets
(16 of 26 Drawing Sheet(s) Filed in Color)
Specification includes a Sequence Listing.

(56) References Cited

OTHER PUBLICATIONS

U.S. Appl. No. 15/004,854 Restriction Requirement dated Jan. 10, 2017.
PCT/US2016/014633 International Search Report and Written Opinion dated Jun. 8, 2016.
Häggqvist, et al., "Medin: An integral fragment of aortic smooth muscle cell-produced lactadherin forms the most common human amyloid", *Proc. Natl. Acad. Sci., USA,* vol. 96, No. 15, pp. 8669-8674 (Jul. 1999).
Peng, et al., "Medin-amyloid: A recently characterized age-associated arterial amyloid form affects mainly arteries in the upper part of the body", *Amyloid,* 12(2): 96-102 (Jun. 2005).
Peng, et al., "Role of aggregated medin in the pathogenesis of thoracic aortic aneurysm and dissection", *Laboratory Investigation,* 87, 1195-1205 (2007).
Shughrue, et al., "Abstract 464: Novel Anti-Medin Antibodies Detect Medin Amyloid Deposits in the Aorta of Patients with Thoracic Aneurysms or Marfan Syndrome", *Arteriosclerosis, Thrombosis, and Vascular Biology, Poster Abstract Presentation, Poster Session II,* vol. 35, A464 (May 1, 2015) retrieved from the Internet on Apr. 21, 2016: <URL:http://atvb.ahajournals.org/content/35/Suppl_1/A464.abstract?sid=7079a197-c00d-42ec-9b72-33f4c809fb590>.
PCT/US2016/014633 International Preliminary Report on Patentability dated Jul. 25, 2017.
Downs, et al., "Analysis of collagenase-cleavage of type II collagen using a neoepitope ELISA," *J Immunol Methods,,* 247(1-2):25-34, (Jan. 1, 2001).
Janatova, "C2, C4 Components and C3a, C4a, and C5a Fragments of the Complement System," *Methods in Enzymology,* vol. 162, pp. 579-625, Copyright 1988 by Academic Press Inc.
Murphy, et al., "Development of a Monoclonal Antibody Specific for the COOH-Terminal of β-Amyloid 1-42 and Its Immunohistochemical Reactivity in Alzheimer's Disease and Related Disorders," *American Journal of Pathology,* vol. 144, No. 5, (May 1994).
Mort, et al., "The use of cleavage site specific antibodies to delineate protein processing and breakdown pathways," *J Clin Pathol: Mol Pathol,* 52:11-18, (1999).

\* cited by examiner

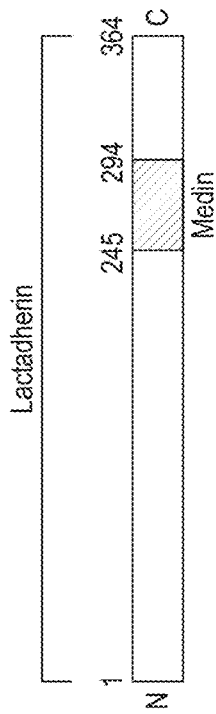

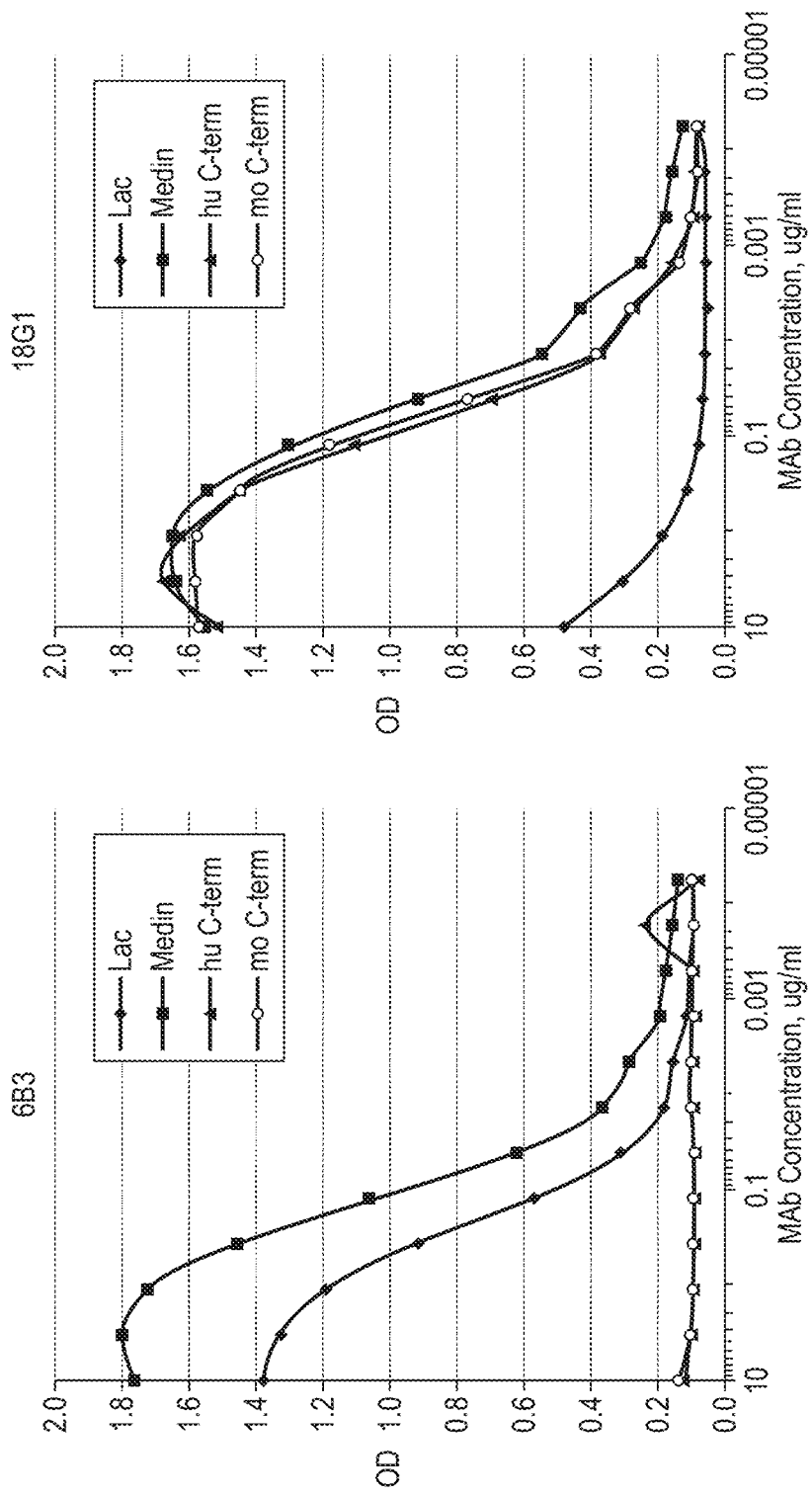

| | | | | | | |
|---|---|---|---|---|---|---|
| | | 10 | 20 | 30 | 40 | 50 | 60 |

```
              10         20         30         40         50         60
              |          |          |          |          |          |
M6B3VH     QVTLKESGPGILQPSQTLSLTCSFSGFSLSTSDMGVGWIRQPSGKGLEWLAHIWWNDNKYY
AAD53863.1 QVTLKESGPALVKPTQTLTLTCTFSGFSLSTSGMRVSWIRQPPGKALEWLARIDWDDDKFY
Hu6B3VHv1  QVQLQESGPGLVKPSQTLSLTCTFSGFSLSTSDMGVGWIRQPPGKALEWLAHIWWNDNKYY
Hu6B3VHv2  EVQLQESGPGLVKPSQTLSLTCTFSGFSLSTSDMGVGWIRQPPGKGLEWLAHIWWNDNKYY
Hu6B3VHv3  EVQLQESGPGLVKPSQTLSLTCTFSGFSLSTSDMGVGWIRQPPGKGLEWIGHIWWNDNKYY 70         80         90        100        110
              |          |          |          |          |
M6B3VH     NIALKNRLTVSKDTSNNQVFLKIASVDTADTATYYCARLVGSWF-AYWGQGTLVTVSA   (SEQ ID NO:11)
AAD53863.1 STSLKTRLTISKDTSKNQVVLTMTNMDPVDTATYYCARIMMGNWFDPWGQGTLVTVSS   (SEQ ID NO:25)
Hu6B3VHv1  NIALKNRLTISKDTSKNQVVLTMTNMDPVDTATYYCARLVGSWF-AYWGQGTLVTVSS   (SEQ ID NO:26)
Hu6B3VHv2  NIALKNRLTISKDTSKNQVSLKLTSVTAADTAVYYCARLVGSWF-AYWGQGTLVTVSS   (SEQ ID NO:27)
Hu6B3VHv3  NIALKNRVTISKDTSKNQFSLKLSSVTAADTAVYYCARLVGSWF-AYWGQGTTVTVSS   (SEQ ID NO:28)
```

FIG. 7

| | | |
|---|---|---|
| M18G1VH | EVQLVESGGGLVKPGGSLKLSCAASGFTFSSYAMSWVRQTPEKRLEWVAGISSSGDYYTYYP | |
| AAX82494.1 | QVQLQESGGGLVKPGGSLKLSCAASGFTFSSYGMSWVRQTPDKRLEWVATISSGGSYTYYP | |
| Hu18G1VHv1 | QVQLQESGGGLVKPGGSLKLSCAASGFTFSSYAMSWVRQTPDKRLEWVAGISSGDYYTYYP | |
| Hu18G1VHv2 | EVQLVESGGGLVQPGGSLRLSCAASGFTFSSYAMSWVRQAPGKGLEWVSGISSGDYYTYYP | |
| M18G1VH | DTVKGRFTISRDNARNTLYLQMRSLRSEDTAMYYCVRGRGNTGPRVGYWGQGTSVTVSS | (SEQ ID NO:3) |
| AAX82494.1 | DSVKGRFTISRDNAKNTLYLQMSSLKSEDTAMYYCARLYYGYRYYFDYWGQGTMVTVSS | (SEQ ID NO:33) |
| Hu18G1VHv1 | DTVKGRFTISRDNAKNTLYLQMSSLKSEDTAMYYCARGRGNTGPRVGYWGQGTMVTVSS | (SEQ ID NO:34) |
| Hu18G1VHv2 | DTVKGRFTISRDNAKNSLYLQMNSLRAEDTAVYYCVRGRGNTGPRVGYWGQGTTVTVSS | (SEQ ID NO:35) |

FIG. 9

```
              10         20         30         40         50         60
M18G1VL      DIVMTQSQKFMSTSVGDRVSVTCKASQNVGTNVAWYQQKPGQSPKALIYSASYRYSGVPDR
AAD39507.1   DIQMTQSPSFLSASVGDRVTITCRASQHINSWLAWYQQKPGKAPKLLIYAASRLQSGVPSR
Hu18G1VLv1   DIVMTQSPSSLSVSPGDRASISCKASQNVGTNVAWYQQKPGQAPQLLIYSASYRYSGVPSR
Hu18G1VLv2   DIVMTQSPSSLSVSPGDRASISCKASQNVGTNVAWYQQKPGQAPKLLIYSASYRYSGVPDR 70         80         90         100
M18G1VL      FTGSGSGTDFTLTISNVQSEDLAEYFCQQYNSFPLTFGAGTKLELK  (SEQ ID NO:36)
AAD39507.1   FSGSGSGTEFTLTISSLQPEDFATYYCQQLNSYPLTFGGGTKLEIK  (SEQ ID NO:37)
Hu18G1VLv1   FSGSGSGTDFTLTISRVQAEDFAVYYCQQYNSFPLTFGGGTKLEIK  (SEQ ID NO:38)
Hu18G1VLv2   FSGSGSGTDFTLTISRVQAEDLAVYYCQQYNSFPLTFGGGTKLEIK  (SEQ ID NO:39)
```

| Kabat residue # | Linear residue # | FR or CDR | Murine 6B3VH (SEQ ID NO: 11) | Hu VH Acceptor FR Acc# AAD53863.1 (SEQ ID NO: 25) | Hu6B3VHv1 (SEQ ID NO: 26) | Hu6B3VHv2 (SEQ ID NO:27) | Hu6B3VHv3 (SEQ ID NO:28) |
|---|---|---|---|---|---|---|---|
| 1 | 1 | Fr1 | Q | Q | Q | E | E |
| 2 | 2 | Fr1 | V | V | V | V | V |
| 3 | 3 | Fr1 | T | T | Q | Q | Q |
| 4 | 4 | Fr1 | L | L | L | L | L |
| 5 | 5 | Fr1 | K | K | Q | Q | Q |
| 6 | 6 | Fr1 | E | E | E | E | E |
| 7 | 7 | Fr1 | S | S | S | S | S |
| 8 | 8 | Fr1 | G | G | G | G | G |
| 9 | 9 | Fr1 | P | P | P | P | P |
| 10 | 10 | Fr1 | G | A | G | G | G |
| 11 | 11 | Fr1 | I | L | L | L | L |
| 12 | 12 | Fr1 | L | V | V | V | V |
| 13 | 13 | Fr1 | Q | K | K | K | K |
| 14 | 14 | Fr1 | P | P | P | P | P |
| 15 | 15 | Fr1 | S | T | S | S | S |
| 16 | 16 | Fr1 | Q | Q | Q | Q | Q |
| 17 | 17 | Fr1 | T | T | T | T | T |
| 18 | 18 | Fr1 | L | L | L | L | L |
| 19 | 19 | Fr1 | S | T | S | S | S |
| 20 | 20 | Fr1 | L | L | L | L | L |
| 21 | 21 | Fr1 | T | T | T | T | T |
| 22 | 22 | Fr1 | C | C | C | C | C |
| 23 | 23 | Fr1 | S | T | T | T | T |
| 24 | 24 | Fr1 | F | F | F | F | F |
| 25 | 25 | Fr1 | S | S | S | S | S |
| 26 | 26 | CDR-H1 | G | G | G | G | G |
| 27 | 27 | CDR-H1 | F | F | F | F | F |
| 28 | 28 | CDR-H1 | S | S | S | S | S |
| 29 | 29 | CDR-H1 | L | L | L | L | L |
| 30 | 30 | CDR-H1 | S | S | S | S | S |
| 31 | 31 | CDR-H1 | T | T | T | T | T |
| 32 | 32 | CDR-H1 | S | S | S | S | S |
| 33 | 33 | CDR-H1 | D | G | D | D | D |

Figure 11B

| | | | | | | | |
|---|---|---|---|---|---|---|---|
| Humanized 6B3 VH Regions |||||||||
| Kabat residue # | Linear residue # | FR or CDR | Murine 6B3VH (SEQ ID NO: 11) | Hu VH Acceptor FR Acc# AAD53863.1 (SEQ ID NO: 25) | Hu6B3VHv1 (SEQ ID NO: 26) | Hu6B3VHv2 (SEQ ID NO:27) | Hu6B3VHv3 (SEQ ID NO:28) |
| 34 | 34 | CDR-H1 | M | M | M | M | M |
| 35 | 35 | CDR-H1 | G | R | G | G | G |
| 35A | 36 | CDR-H1 | V | V | V | V | V |
| 35B | 37 | CDR-H1 | G | S | G | G | G |
| 36 | 38 | Fr2 | W | W | W | W | W |
| 37 | 39 | Fr2 | I | I | I | I | I |
| 38 | 40 | Fr2 | R | R | R | R | R |
| 39 | 41 | Fr2 | Q | Q | Q | Q | Q |
| 40 | 42 | Fr2 | P | P | P | P | P |
| 41 | 43 | Fr2 | S | P | P | P | P |
| 42 | 44 | Fr2 | G | G | G | G | G |
| 43 | 45 | Fr2 | K | K | K | K | K |
| 44 | 46 | Fr2 | G | A | A | G | G |
| 45 | 47 | Fr2 | L | L | L | L | L |
| 46 | 48 | Fr2 | E | E | E | E | E |
| 47 | 49 | Fr2 | W | W | W | W | W |
| 48 | 50 | Fr2 | L | L | L | L | I |
| 49 | 51 | Fr2 | A | A | A | A | G |
| 50 | 52 | CDR-H2 | H | R | H | H | H |
| 51 | 53 | CDR-H2 | I | I | I | I | I |
| 52 | 54 | CDR-H2 | W | D | W | W | W |
| 52A | | CDR-H2 | | | | | |
| 52B | | CDR-H2 | | | | | |
| 52C | | CDR-H2 | — | — | — | — | — |
| 53 | 55 | CDR-H2 | W | W | W | W | W |
| 54 | 56 | CDR-H2 | N | D | N | N | N |
| 55 | 57 | CDR-H2 | D | D | D | D | D |
| 56 | 58 | CDR-H2 | N | D | N | N | N |
| 57 | 59 | CDR-H2 | K | K | K | K | K |
| 58 | 60 | CDR-H2 | Y | F | Y | Y | Y |
| 59 | 61 | CDR-H2 | Y | Y | Y | Y | Y |
| 60 | 62 | CDR-H2 | N | S | N | N | N |
| 61 | 63 | CDR-H2 | I | T | I | I | I |
| 62 | 64 | CDR-H2 | A | S | A | A | A |

Figure 11C

| | | | | Humanized 6B3 VH Regions | | | |
|---|---|---|---|---|---|---|---|
| Kabat residue # | Linear residue # | FR or CDR | Murine 6B3VH (SEQ ID NO: 11) | Hu VH Acceptor FR Acc# AAD53863.1 (SEQ ID NO: 25) | Hu6B3VHv1 (SEQ ID NO: 26) | Hu6B3VHv2 (SEQ ID NO:27) | Hu6B3VHv3 (SEQ ID NO:28) |
| 63 | 65 | CDR-H2 | L | L | L | L | L |
| 64 | 66 | CDR-H2 | K | K | K | K | K |
| 65 | 67 | CDR-H2 | N | I | N | N | N |
| 66 | 68 | Fr3 | R | R | R | R | R |
| 67 | 69 | Fr3 | L | L | L | L | V |
| 68 | 70 | Fr3 | T | T | T | T | T |
| 69 | 71 | Fr3 | V | I | I | I | I |
| 70 | 72 | Fr3 | S | S | S | S | S |
| 71 | 73 | Fr3 | K | K | K | K | K |
| 72 | 74 | Fr3 | D | D | D | D | D |
| 73 | 75 | Fr3 | T | T | T | T | T |
| 74 | 76 | Fr3 | S | S | S | S | S |
| 75 | 77 | Fr3 | N | K | K | K | K |
| 76 | 78 | Fr3 | N | N | N | N | N |
| 77 | 79 | Fr3 | Q | Q | Q | Q | Q |
| 78 | 80 | Fr3 | V | V | V | V | F |
| 79 | 81 | Fr3 | F | V | V | S | S |
| 80 | 82 | Fr3 | L | L | L | L | L |
| 81 | 83 | Fr3 | K | T | T | K | K |
| 82 | 84 | Fr3 | I | M | M | L | L |
| 82A | 85 | Fr3 | A | T | T | T | S |
| 82B | 86 | Fr3 | S | N | N | S | S |
| 82C | 87 | Fr3 | V | M | M | V | V |
| 83 | 88 | Fr3 | D | D | D | T | T |
| 84 | 89 | Fr3 | T | P | P | A | A |
| 85 | 90 | Fr3 | A | V | V | A | A |
| 86 | 91 | Fr3 | D | D | D | D | D |
| 87 | 92 | Fr3 | T | T | T | T | T |
| 88 | 93 | Fr3 | A | A | A | A | A |
| 89 | 94 | Fr3 | T | T | T | V | V |
| 90 | 95 | Fr3 | Y | Y | Y | Y | Y |
| 91 | 96 | Fr3 | Y | Y | Y | Y | Y |
| 92 | 97 | Fr3 | C | C | C | C | C |
| 93 | 98 | Fr3 | A | A | A | A | A |

Figure 11D

| | | | | | | | |
|---|---|---|---|---|---|---|---|
| Humanized 6B3 VH Regions ||||||||
| Kabat residue # | Linear residue # | FR or CDR | Murine 6B3VH (SEQ ID NO: 11) | Hu VH Acceptor FR Acc# AAD53863.1 (SEQ ID NO: 25) | Hu6B3VHv1 (SEQ ID NO: 26) | Hu6B3VHv2 (SEQ ID NO:27) | Hu6B3VHv3 (SEQ ID NO:28) |
| 94 | 99 | Fr3 | R | R | R | R | R |
| 95 | 100 | CDR-H3 | L | I | L | L | L |
| 96 | 101 | CDR-H3 | V | M | V | V | V |
| 97 | 102 | CDR-H3 | G | M | G | G | G |
| 98 | 103 | CDR-H3 | S | G | S | S | S |
| 99 | 104 | CDR-H3 | W | N | W | W | W |
| 100 | 105 | CDR-H3 | F | W | F | F | F |
| 100A | | CDR-H3 | | F | | | |
| 100B | | CDR-H3 | | | | | |
| 100C | | CDR-H3 | | | | | |
| 100D | | CDR-H3 | | | | | |
| 100E | | CDR-H3 | | | | | |
| 100F | | CDR-H3 | | | | | |
| 100G | | CDR-H3 | | | | | |
| 100H | | CDR-H3 | | | | | |
| 100I | | CDR-H3 | | | | | |
| 100J | | CDR-H3 | | | | | |
| 100K | | CDR-H3 | | | | | |
| 101 | 106 | CDR-H3 | A | D | A | A | A |
| 102 | 107 | CDR-H3 | Y | P | Y | Y | Y |
| 103 | 108 | Fr4 | W | W | W | W | W |
| 104 | 109 | Fr4 | G | G | G | G | G |
| 105 | 110 | Fr4 | Q | Q | Q | Q | Q |
| 106 | 111 | Fr4 | G | G | G | G | G |
| 107 | 112 | Fr4 | T | T | T | T | T |
| 108 | 113 | Fr4 | L | L | L | L | T |
| 109 | 114 | Fr4 | V | V | V | V | V |
| 110 | 115 | Fr4 | T | T | T | T | T |
| 111 | 116 | Fr4 | V | V | V | V | V |
| 112 | 117 | Fr4 | S | S | S | S | S |
| 113 | 118 | Fr4 | A | S | S | S | S |

Figure 12A

| | | | | Hu VL Acceptor Fr Acc# | | |
|---|---|---|---|---|---|---|
| Kabat residue # | Linear residue # | FR or CDR | Murine 6B3VL (SEQ ID NO:29) | BAC01558.1 (SEQ ID NO:30) | Hu6B3VLv1 (SEQ ID NO:31) | Hu6B3VLv2 (SEQ ID NO:32) |
| 1 | 1 | Fr1 | D | D | D | D |
| 2 | 2 | Fr1 | I | I | I | I |
| 3 | 3 | Fr1 | Q | Q | Q | Q |
| 4 | 4 | Fr1 | M | M | M | M |
| 5 | 5 | Fr1 | T | T | T | T |
| 6 | 6 | Fr1 | Q | Q | Q | Q |
| 7 | 7 | Fr1 | T | S | S | S |
| 8 | 8 | Fr1 | T | P | P | P |
| 9 | 9 | Fr1 | S | S | S | S |
| 10 | 10 | Fr1 | S | S | S | S |
| 11 | 11 | Fr1 | L | L | L | L |
| 12 | 12 | Fr1 | S | S | S | S |
| 13 | 13 | Fr1 | A | A | A | A |
| 14 | 14 | Fr1 | S | S | S | S |
| 15 | 15 | Fr1 | L | V | V | V |
| 16 | 16 | Fr1 | G | G | G | G |
| 17 | 17 | Fr1 | D | D | D | D |
| 18 | 18 | Fr1 | R | R | R | R |
| 19 | 19 | Fr1 | V | V | V | V |
| 20 | 20 | Fr1 | T | T | T | T |
| 21 | 21 | Fr1 | I | I | I | I |
| 22 | 22 | Fr1 | S | T | T | T |
| 23 | 23 | Fr1 | C | C | C | C |
| 24 | 24 | CDR-L1 | R | R | R | R |
| 25 | 25 | CDR-L1 | A | A | A | A |
| 26 | 26 | CDR-L1 | S | S | S | S |
| 27 | 27 | CDR-L1 | Q | Q | Q | Q |
| 27A | | CDR-L1 | — | — | — | — |
| 27B | | CDR-L1 | — | — | — | — |
| 27C | | CDR-L1 | | | | |
| 27D | | CDR-L1 | | | | |
| 27E | | CDR-L1 | — | — | — | — |
| 27F | | CDR-L1 | | | | |

Figure 12B

| | | | | Hu VL Acceptor Fr Acc# | | |
|---|---|---|---|---|---|---|
| Kabat residue # | Linear residue # | FR or CDR | Murine 6B3VL (SEQ ID NO:29) | BAC01558.1 (SEQ ID NO:30) | Hu6B3VLv1 (SEQ ID NO:31) | Hu6B3VLv2 (SEQ ID NO:32) |
| 28 | 28 | CDR-L1 | D | S | D | D |
| 29 | 29 | CDR-L1 | I | I | I | I |
| 30 | 30 | CDR-L1 | S | S | S | S |
| 31 | 31 | CDR-L1 | N | S | N | N |
| 32 | 32 | CDR-L1 | F | Y | F | F |
| 33 | 33 | CDR-L1 | L | L | L | L |
| 34 | 34 | CDR-L1 | S | N | S | S |
| 35 | 35 | Fr2 | W | W | W | W |
| 36 | 36 | Fr2 | Y | Y | Y | Y |
| 37 | 37 | Fr2 | H | Q | Q | Q |
| 38 | 38 | Fr2 | Q | Q | Q | Q |
| 39 | 39 | Fr2 | K | K | K | K |
| 40 | 40 | Fr2 | P | P | P | P |
| 41 | 41 | Fr2 | D | G | G | G |
| 42 | 42 | Fr2 | G | K | K | K |
| 43 | 43 | Fr2 | T | A | A | A |
| 44 | 44 | Fr2 | V | P | P | P |
| 45 | 45 | Fr2 | K | K | K | K |
| 46 | 46 | Fr2 | L | L | L | L |
| 47 | 47 | Fr2 | L | L | L | L |
| 48 | 48 | Fr2 | I | I | I | I |
| 49 | 49 | Fr2 | Y | Y | Y | Y |
| 50 | 50 | CDR-L2 | Y | A | Y | Y |
| 51 | 51 | CDR-L2 | T | A | T | T |
| 52 | 52 | CDR-L2 | S | S | S | S |
| 53 | 53 | CDR-L2 | R | S | R | R |
| 54 | 54 | CDR-L2 | L | L | L | L |
| 55 | 55 | CDR-L2 | H | Q | H | H |
| 56 | 56 | CDR-L2 | S | S | S | S |
| 57 | 57 | Fr3 | G | G | G | G |
| 58 | 58 | Fr3 | V | V | V | V |
| 59 | 59 | Fr3 | P | P | P | P |
| 60 | 60 | Fr3 | P | S | S | S |

Figure 12C

| Humanized 6B3 VL Regions | | | | | | |
|---|---|---|---|---|---|---|
| Kabat residue # | Linear residue # | FR or CDR | Murine 6B3VL (SEQ ID NO:29) | Hu VL Acceptor Fr Acc# BAC01558.1 (SEQ ID NO:30) | Hu6B3VLv1 (SEQ ID NO:31) | Hu6B3VLv2 (SEQ ID NO:32) |
| 61 | 61 | Fr3 | R | R | R | R |
| 62 | 62 | Fr3 | F | F | F | F |
| 63 | 63 | Fr3 | S | S | S | S |
| 64 | 64 | Fr3 | G | G | G | G |
| 65 | 65 | Fr3 | S | S | S | S |
| 66 | 66 | Fr3 | G | G | G | G |
| 67 | 67 | Fr3 | S | S | S | S |
| 68 | 68 | Fr3 | G | G | G | G |
| 69 | 69 | Fr3 | T | T | T | T |
| 70 | 70 | Fr3 | D | D | D | D |
| 71 | 71 | Fr3 | Y | F | F | Y |
| 72 | 72 | Fr3 | S | T | T | T |
| 73 | 73 | Fr3 | L | L | L | L |
| 74 | 74 | Fr3 | T | T | T | T |
| 75 | 75 | Fr3 | I | I | I | I |
| 76 | 76 | Fr3 | S | S | S | S |
| 77 | 77 | Fr3 | N | S | S | S |
| 78 | 78 | Fr3 | L | L | L | L |
| 79 | 79 | Fr3 | E | Q | Q | Q |
| 80 | 80 | Fr3 | Q | P | P | P |
| 81 | 81 | Fr3 | E | E | E | E |
| 82 | 82 | Fr3 | D | D | D | D |
| 83 | 83 | Fr3 | I | F | F | F |
| 84 | 84 | Fr3 | A | A | A | A |
| 85 | 85 | Fr3 | T | T | T | T |
| 86 | 86 | Fr3 | Y | Y | Y | Y |
| 87 | 87 | Fr3 | F | Y | Y | F |
| 88 | 88 | Fr3 | C | C | C | C |
| 89 | 89 | CDR-L3 | Q | Q | Q | Q |
| 90 | 90 | CDR-L3 | Q | Q | Q | Q |
| 91 | 91 | CDR-L3 | G | S | G | G |
| 92 | 92 | CDR-L3 | K | Y | K | K |
| 93 | 93 | CDR-L3 | T | S | T | T |

Figure 12D

| | | | | Hu VL Acceptor Fr | | |
|---|---|---|---|---|---|---|
| Kabat residue # | Linear residue # | FR or CDR | Murine 6B3VL (SEQ ID NO:29) | Acc# BAC01558.1 (SEQ ID NO:30) | Hu6B3VLv1 (SEQ ID NO:31) | Hu6B3VLv2 (SEQ ID NO:32) |
| Humanized 6B3 VL Regions | | | | | | |
| 94 | 94 | CDR-L3 | L | L | L | L |
| 95 | 95 | CDR-L3 | P | P | P | P |
| 95A | | CDR-L3 | | | | |
| 95B | | CDR-L3 | | | | |
| 95C | | CDR-L3 | | | | |
| 95D | | CDR-L3 | | | | |
| 95E | | CDR-L3 | | | | |
| 95F | | CDR-L3 | | | | |
| 96 | 96 | CDR-L3 | P | P | P | P |
| 97 | 97 | CDR-L3 | I | I | I | I |
| 98 | 98 | Fr4 | F | F | F | F |
| 99 | 99 | Fr4 | G | G | G | G |
| 100 | 100 | Fr4 | G | G | G | Q |
| 101 | 101 | Fr4 | G | G | G | G |
| 102 | 102 | Fr4 | T | T | T | T |
| 103 | 103 | Fr4 | K | K | K | K |
| 104 | 104 | Fr4 | L | V | V | L |
| 105 | 105 | Fr4 | E | E | E | E |
| 106 | 106 | Fr4 | I | I | I | I |
| 106A | | Fr4 | | | | |
| 107 | 107 | Fr4 | K | K | K | K |

Figure 13A

| | | | | Humanized 18G1 VH Regions | | |
|---|---|---|---|---|---|---|
| Kabat residue # | Linear residue # | FR or CDR | Murine 18G1VH (SEQ ID NO: 3) | Hu VH Acceptor FR Acc#AAX82494.1 (SEQ ID NO: 33) | Hu18G1VHv1 (SEQ ID NO: 34) | Hu8G1VHv2 (SEQ ID NO: 35) |
| 1 | 1 | Fr1 | E | Q | Q | E |
| 2 | 2 | Fr1 | V | V | V | V |
| 3 | 3 | Fr1 | Q | Q | Q | Q |
| 4 | 4 | Fr1 | L | L | L | L |
| 5 | 5 | Fr1 | V | Q | Q | V |
| 6 | 6 | Fr1 | E | E | E | E |
| 7 | 7 | Fr1 | S | S | S | S |
| 8 | 8 | Fr1 | G | G | G | G |
| 9 | 9 | Fr1 | G | G | G | G |
| 10 | 10 | Fr1 | G | G | G | G |
| 11 | 11 | Fr1 | L | L | L | L |
| 12 | 12 | Fr1 | V | V | V | V |
| 13 | 13 | Fr1 | K | K | K | Q |
| 14 | 14 | Fr1 | P | P | P | P |
| 15 | 15 | Fr1 | G | G | G | G |
| 16 | 16 | Fr1 | G | G | G | G |
| 17 | 17 | Fr1 | S | S | S | S |
| 18 | 18 | Fr1 | L | L | L | L |
| 19 | 19 | Fr1 | K | K | K | R |
| 20 | 20 | Fr1 | L | L | L | L |
| 21 | 21 | Fr1 | S | S | S | S |
| 22 | 22 | Fr1 | C | C | C | C |
| 23 | 23 | Fr1 | A | A | A | A |
| 24 | 24 | Fr1 | A | A | A | A |
| 25 | 25 | Fr1 | S | S | S | S |
| 26 | 26 | CDR-H1 | G | G | G | G |
| 27 | 27 | CDR-H1 | F | F | F | F |
| 28 | 28 | CDR-H1 | T | T | T | T |
| 29 | 29 | CDR-H1 | F | F | F | F |
| 30 | 30 | CDR-H1 | S | S | S | S |
| 31 | 31 | CDR-H1 | S | S | S | S |
| 32 | 32 | CDR-H1 | Y | Y | Y | Y |
| 33 | 33 | CDR-H1 | A | G | A | A |
| 34 | 34 | CDR-H1 | M | M | M | M |

Figure 13B

Humanized 18G1 VH Regions

| Kabat residue # | Linear residue # | FR or CDR | Murine 18G1VH (SEQ ID NO: 3) | Hu VH Acceptor FR Acc#AAX82494.1 (SEQ ID NO: 33) | Hu18G1VHv1 (SEQ ID NO: 34) | Hu8G1VHv2 (SEQ ID NO: 35) |
|---|---|---|---|---|---|---|
| 35 | 35 | CDR-H1 | S | S | S | S |
| 35A | | CDR-H1 | | | | |
| 35B | | CDR-H1 | | | | |
| 36 | 36 | Fr2 | W | W | W | W |
| 37 | 37 | Fr2 | V | V | V | V |
| 38 | 38 | Fr2 | R | R | R | R |
| 39 | 39 | Fr2 | Q | Q | Q | Q |
| 40 | 40 | Fr2 | T | T | T | A |
| 41 | 41 | Fr2 | P | P | P | P |
| 42 | 42 | Fr2 | E | D | D | G |
| 43 | 43 | Fr2 | K | K | K | K |
| 44 | 44 | Fr2 | R | R | R | G |
| 45 | 45 | Fr2 | L | L | L | L |
| 46 | 46 | Fr2 | E | E | E | E |
| 47 | 47 | Fr2 | W | W | W | W |
| 48 | 48 | Fr2 | V | V | V | V |
| 49 | 49 | Fr2 | A | A | A | S |
| 50 | 50 | CDR-H2 | G | T | G | G |
| 51 | 51 | CDR-H2 | I | I | I | I |
| 52 | 52 | CDR-H2 | S | S | S | S |
| 52A | 53 | CDR-H2 | S | S | S | S |
| 52B | | CDR-H2 | | | | |
| 52C | | CDR-H2 | | | | |
| 53 | 54 | CDR-H2 | G | G | G | G |
| 54 | 55 | CDR-H2 | D | G | D | D |
| 55 | 56 | CDR-H2 | Y | S | Y | Y |
| 56 | 57 | CDR-H2 | Y | Y | Y | Y |
| 57 | 58 | CDR-H2 | T | T | T | T |
| 58 | 59 | CDR-H2 | Y | Y | Y | Y |
| 59 | 60 | CDR-H2 | Y | Y | Y | Y |
| 60 | 61 | CDR-H2 | P | P | P | P |
| 61 | 62 | CDR-H2 | D | D | D | D |
| 62 | 63 | CDR-H2 | T | S | T | T |
| 63 | 64 | CDR-H2 | V | V | V | V |

Figure 13C

| | | | | Humanized 18G1 VH Regions | | |
|---|---|---|---|---|---|---|
| Kabat residue # | Linear residue # | FR or CDR | Murine 18G1VH (SEQ ID NO: 3) | Hu VH Acceptor FR Acc#AAX82494.1 (SEQ ID NO: 33) | Hu18G1VHv1 (SEQ ID NO: 34) | Hu8G1VHv2 (SEQ ID NO: 35) |
| 64 | 65 | CDR-H2 | K | K | K | K |
| 65 | 66 | CDR-H2 | G | G | G | G |
| 66 | 67 | Fr3 | R | R | R | R |
| 67 | 68 | Fr3 | F | F | F | F |
| 68 | 69 | Fr3 | T | T | T | T |
| 69 | 70 | Fr3 | I | I | I | I |
| 70 | 71 | Fr3 | S | S | S | S |
| 71 | 72 | Fr3 | R | R | R | R |
| 72 | 73 | Fr3 | D | D | D | D |
| 73 | 74 | Fr3 | N | N | N | N |
| 74 | 75 | Fr3 | A | A | A | A |
| 75 | 76 | Fr3 | R | K | K | K |
| 76 | 77 | Fr3 | N | N | N | N |
| 77 | 78 | Fr3 | T | T | T | S |
| 78 | 79 | Fr3 | L | L | L | L |
| 79 | 80 | Fr3 | Y | Y | Y | Y |
| 80 | 81 | Fr3 | L | L | L | L |
| 81 | 82 | Fr3 | Q | Q | Q | Q |
| 82 | 83 | Fr3 | M | M | M | M |
| 82A | 84 | Fr3 | R | S | S | N |
| 82B | 85 | Fr3 | S | S | S | S |
| 82C | 86 | Fr3 | L | L | L | L |
| 83 | 87 | Fr3 | R | K | K | R |
| 84 | 88 | Fr3 | S | S | S | A |
| 85 | 89 | Fr3 | E | E | E | E |
| 86 | 90 | Fr3 | D | D | D | D |
| 87 | 91 | Fr3 | T | T | T | T |
| 88 | 92 | Fr3 | A | A | A | A |
| 89 | 93 | Fr3 | M | M | M | V |
| 90 | 94 | Fr3 | Y | Y | Y | Y |
| 91 | 95 | Fr3 | Y | Y | Y | Y |
| 92 | 96 | Fr3 | C | C | C | C |
| 93 | 97 | Fr3 | V | A | A | V |
| 94 | 98 | Fr3 | R | R | R | R |

Figure 13D

| | | | | | | |
|---|---|---|---|---|---|---|
| Humanized 18G1 VH Regions | | | | | | |
| Kabat residue # | Linear residue # | FR or CDR | Murine 18G1VH (SEQ ID NO: 3) | Hu VH Acceptor FR Acc#AAX82494.1 (SEQ ID NO: 33) | Hu18G1VHv1 (SEQ ID NO: 34) | Hu8G1VHv2 (SEQ ID NO: 35) |
| 95 | 99 | CDR-H3 | G | L | G | G |
| 96 | 100 | CDR-H3 | R | Y | R | R |
| 97 | 101 | CDR-H3 | G | Y | G | G |
| 98 | 102 | CDR-H3 | N | G | N | N |
| 99 | 103 | CDR-H3 | T | Y | T | T |
| 100 | 104 | CDR-H3 | G | R | G | G |
| 100A | 105 | CDR-H3 | P | Y | P | P |
| 100B | 106 | CDR-H3 | R | Y | R | R |
| 100C | 107 | CDR-H3 | V | F | V | V |
| 100D | | CDR-H3 | | | | |
| 100E | | CDR-H3 | | | | |
| 100F | | CDR-H3 | | | | |
| 100G | | CDR-H3 | | | | |
| 100H | | CDR-H3 | | | | |
| 100I | | CDR-H3 | | | | |
| 100J | | CDR-H3 | | | | |
| 100K | | CDR-H3 | | | | |
| 101 | 108 | CDR-H3 | G | D | G | G |
| 102 | 109 | CDR-H3 | Y | Y | Y | Y |
| 103 | 110 | Fr4 | W | W | W | W |
| 104 | 111 | Fr4 | G | G | G | G |
| 105 | 112 | Fr4 | Q | Q | Q | Q |
| 106 | 113 | Fr4 | G | G | G | G |
| 107 | 114 | Fr4 | T | T | T | T |
| 108 | 115 | Fr4 | S | M | M | T |
| 109 | 116 | Fr4 | V | V | V | V |
| 110 | 117 | Fr4 | T | T | T | T |
| 111 | 118 | Fr4 | V | V | V | V |
| 112 | 119 | Fr4 | S | S | S | S |
| 113 | 120 | Fr4 | S | S | S | S |

Figure 14A

| | | | | | | |
|---|---|---|---|---|---|---|
| Humanized 18G1 VL Regions | | | | | | |
| Kabat residue # | Linear residue # | FR or CDR | Murine 18G1VL (SEQ ID NO: 36) | Hu VL Acceptor Fr Acc#AAD39507.1 (SEQ ID NO: 37) | Hu18G1VLv1 (SEQ ID NO: 38) | Hu18G1VLv2 (SEQ ID NO: 39) |
| 1 | 1 | Fr1 | D | D | D | D |
| 2 | 2 | Fr1 | I | I | I | I |
| 3 | 3 | Fr1 | V | Q | V | V |
| 4 | 4 | Fr1 | M | M | M | M |
| 5 | 5 | Fr1 | T | T | T | T |
| 6 | 6 | Fr1 | Q | Q | Q | Q |
| 7 | 7 | Fr1 | S | S | S | S |
| 8 | 8 | Fr1 | Q | P | P | P |
| 9 | 9 | Fr1 | K | S | S | S |
| 10 | 10 | Fr1 | F | F | S | S |
| 11 | 11 | Fr1 | M | L | L | L |
| 12 | 12 | Fr1 | S | S | S | S |
| 13 | 13 | Fr1 | T | A | V | V |
| 14 | 14 | Fr1 | S | S | S | S |
| 15 | 15 | Fr1 | V | V | P | P |
| 16 | 16 | Fr1 | G | G | G | G |
| 17 | 17 | Fr1 | D | D | D | D |
| 18 | 18 | Fr1 | R | R | R | R |
| 19 | 19 | Fr1 | V | V | A | A |
| 20 | 20 | Fr1 | S | T | S | S |
| 21 | 21 | Fr1 | V | I | I | I |
| 22 | 22 | Fr1 | T | T | S | S |
| 23 | 23 | Fr1 | C | C | C | C |
| 24 | 24 | CDR-L1 | K | R | K | K |
| 25 | 25 | CDR-L1 | A | A | A | A |
| 26 | 26 | CDR-L1 | S | S | S | S |
| 27 | 27 | CDR-L1 | Q | Q | Q | Q |
| 27A | | CDR-L1 | | | | |
| 27B | | CDR-L1 | | | | |
| 27C | | CDR-L1 | — | — | — | — |
| 27D | | CDR-L1 | — | — | — | — |
| 27E | | CDR-L1 | — | — | — | — |
| 27F | | CDR-L1 | — | — | — | — |
| 28 | 28 | CDR-L1 | N | H | N | N |
| 29 | 29 | CDR-L1 | V | I | V | V |

Figure 14B

| | | | | Humanized 18G1 VL Regions | | |
|---|---|---|---|---|---|---|
| Kabat residue # | Linear residue # | FR or CDR | Murine 18G1VL (SEQ ID NO: 36) | Hu VL Acceptor Fr Acc#AAD39507.1 (SEQ ID NO: 37) | Hu18G1VLv1 (SEQ ID NO: 38) | Hu18G1VLv2 (SEQ ID NO: 39) |
| 30 | 30 | CDR-L1 | G | N | G | G |
| 31 | 31 | CDR-L1 | T | S | T | T |
| 32 | 32 | CDR-L1 | N | W | N | N |
| 33 | 33 | CDR-L1 | V | L | V | V |
| 34 | 34 | CDR-L1 | A | A | A | A |
| 35 | 35 | Fr2 | W | W | W | W |
| 36 | 36 | Fr2 | Y | Y | Y | Y |
| 37 | 37 | Fr2 | Q | Q | Q | Q |
| 38 | 38 | Fr2 | Q | Q | Q | Q |
| 39 | 39 | Fr2 | K | K | K | K |
| 40 | 40 | Fr2 | P | P | P | P |
| 41 | 41 | Fr2 | G | G | G | G |
| 42 | 42 | Fr2 | Q | K | Q | Q |
| 43 | 43 | Fr2 | S | A | A | A |
| 44 | 44 | Fr2 | P | P | P | P |
| 45 | 45 | Fr2 | K | K | Q | K |
| 46 | 46 | Fr2 | A | L | L | L |
| 47 | 47 | Fr2 | L | L | L | L |
| 48 | 48 | Fr2 | I | I | I | I |
| 49 | 49 | Fr2 | Y | Y | Y | Y |
| 50 | 50 | CDR-L2 | S | A | S | S |
| 51 | 51 | CDR-L2 | A | A | A | A |
| 52 | 52 | CDR-L2 | S | S | S | S |
| 53 | 53 | CDR-L2 | Y | R | Y | Y |
| 54 | 54 | CDR-L2 | R | L | R | R |
| 55 | 55 | CDR-L2 | Y | Q | Y | Y |
| 56 | 56 | CDR-L2 | S | S | S | S |
| 57 | 57 | Fr3 | G | G | G | G |
| 58 | 58 | Fr3 | V | V | V | V |
| 59 | 59 | Fr3 | P | P | P | P |
| 60 | 60 | Fr3 | D | S | S | D |
| 61 | 61 | Fr3 | R | R | R | R |
| 62 | 62 | Fr3 | F | F | F | F |
| 63 | 63 | Fr3 | T | S | S | S |
| 64 | 64 | Fr3 | G | G | G | G |

Figure 14C

Humanized 18G1 VL Regions

| Kabat residue # | Linear residue # | FR or CDR | Murine 18G1VL (SEQ ID NO: 36) | Hu VL Acceptor Fr Acc#AAD39507.1 (SEQ ID NO: 37) | Hu18G1VLv1 (SEQ ID NO: 38) | Hu18G1VLv2 (SEQ ID NO: 39) |
|---|---|---|---|---|---|---|
| 65 | 65 | Fr3 | S | S | S | S |
| 66 | 66 | Fr3 | G | G | G | G |
| 67 | 67 | Fr3 | S | S | S | S |
| 68 | 68 | Fr3 | G | G | G | G |
| 69 | 69 | Fr3 | T | T | T | T |
| 70 | 70 | Fr3 | D | E | D | D |
| 71 | 71 | Fr3 | F | F | F | F |
| 72 | 72 | Fr3 | T | T | T | T |
| 73 | 73 | Fr3 | L | L | L | L |
| 74 | 74 | Fr3 | T | T | T | T |
| 75 | 75 | Fr3 | I | I | I | I |
| 76 | 76 | Fr3 | S | S | S | S |
| 77 | 77 | Fr3 | N | S | R | R |
| 78 | 78 | Fr3 | V | L | V | V |
| 79 | 79 | Fr3 | Q | Q | Q | Q |
| 80 | 80 | Fr3 | S | P | A | A |
| 81 | 81 | Fr3 | E | E | E | E |
| 82 | 82 | Fr3 | D | D | D | D |
| 83 | 83 | Fr3 | L | F | F | L |
| 84 | 84 | Fr3 | A | A | A | A |
| 85 | 85 | Fr3 | E | T | V | V |
| 86 | 86 | Fr3 | Y | Y | Y | Y |
| 87 | 87 | Fr3 | F | Y | Y | Y |
| 88 | 88 | Fr3 | C | C | C | C |
| 89 | 89 | CDR-L3 | Q | Q | Q | Q |
| 90 | 90 | CDR-L3 | Q | Q | Q | Q |
| 91 | 91 | CDR-L3 | Y | L | Y | Y |
| 92 | 92 | CDR-L3 | N | N | N | N |
| 93 | 93 | CDR-L3 | S | S | S | S |
| 94 | 94 | CDR-L3 | F | Y | F | F |
| 95 | 95 | CDR-L3 | P | P | P | P |
| 95A | | CDR-L3 | | | | |
| 95B | | CDR-L3 | | | | |
| 95C | | CDR-L3 | | | | |
| 95D | | CDR-L3 | | | | |

Figure 14 D

Humanized 18G1 VL Regions

| Kabat residue # | Linear residue # | FR or CDR | Murine 18G1VL (SEQ ID NO: 36) | Hu VL Acceptor Fr Acc#AAD39507.1 (SEQ ID NO: 37) | Hu18G1VLv1 (SEQ ID NO: 38) | Hu18G1VLv2 (SEQ ID NO: 39) |
|---|---|---|---|---|---|---|
| 95E | | CDR-L3 | | | | |
| 95F | | CDR-L3 | | | | |
| 96 | 96 | CDR-L3 | L | L | L | L |
| 97 | 97 | CDR-L3 | T | T | T | T |
| 98 | 98 | Fr4 | F | F | F | F |
| 99 | 99 | Fr4 | G | G | G | G |
| 100 | 100 | Fr4 | A | G | G | G |
| 101 | 101 | Fr4 | G | G | G | G |
| 102 | 102 | Fr4 | T | T | T | T |
| 103 | 103 | Fr4 | K | K | K | K |
| 104 | 104 | Fr4 | L | L | L | L |
| 105 | 105 | Fr4 | E | E | E | E |
| 106 | 106 | Fr4 | L | I | I | I |
| 106A | | Fr4 | | | | |
| 107 | 107 | Fr4 | K | K | K | K |

ANTIBODIES RECOGNIZING MEDIN

CROSS-REFERENCE TO RELATED APPLICATIONS

This application is a continuation in part of U.S. application Ser. No. 15/004,854 filed Jan. 22, 2016, which claims the benefit under 35 USC 119(e) of U.S. Provisional Application No. 62/106,690 filed Jan. 22, 2015, which are incorporated by reference in their entirety.

REFERENCE TO A SEQUENCE LISTING

The Sequence Listing written in file 481194_SEQLST.txt is 30.5 kilobytes, was created on Jun. 29, 2016, and is hereby incorporated by reference.

BACKGROUND

Several diseases are thought to be caused by the abnormal folding and/or aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Medin, a 50 aa cleavage fragment of lactadherin/MFG-E8 is known to aggregate (e.g., undergo amyloidogenesis). Medin amyloid deposits are seen in patients with aortic aneurysms and in patients with Marfan syndrome. While the pathogenic nature of these aggregates is not fully understood, it is thought that medin may perturb smooth muscle cell function and thereby weaken the integrity of the aorta wall. Lactadherin and/or medin have also been implicated in pancreatitis, lupus, Alzheimer's disease and obesity.

SUMMARY OF THE CLAIMED INVENTION

In one aspect, the invention provides an isolated monoclonal antibody that specifically binds to medin, such as, for example, an antibody that specifically binds to full length medin or an N-terminal or C-terminal fragment of medin. Examples of such antibodies bind to an epitope within amino acid residues 1-50 of SEQ ID NO: 1 or within amino acid residues 44-50 of SEQ ID NO: 1.

Some such antibodies compete for binding to human medin with antibody 18G1 or 6B3. The antibodies may specifically bind medin and not native lactadherin, for example, antibodies that specifically recognize a neo-epitope created when medin is cleaved from lactadherin. Other antibodies may specifically bind medin and misfolded lactadherin, but not native lactadherin, such as the form of lactadherin expressed on MDA-MB-231 cells. Certain of these antibodies preferentially bind dense aggregated medin or medin deposits and only weakly bind to monomeric or oligomeric medin. Other antibodies preferentially bind monomeric or oligomeric medin and only weakly bind to dense aggregated medin or medin deposits, while still other antibodies may specifically bind to multiple aggregated forms of medin (e.g., oligomeric, fibrillar, densely aggregated, deposits) as well as monomeric medin.

Some antibodies comprise three light chain CDRs and three heavy chain CDRs of monoclonal antibody 18G1, such as the mouse antibody characterized by a heavy chain variable region having an amino acid sequence comprising SEQ ID NO: 3 and a light chain variable region having an amino acid sequence comprising SEQ ID NO:36.

Some antibodies are a humanized or chimeric 18G1 antibody that specifically binds to human medin, wherein 18G1 is a mouse antibody characterized by a mature heavy chain variable region of SEQ ID NO:3 and a mature light chain variable region of SEQ ID NO: 36.

Some antibodies are a humanized antibody comprising a humanized mature heavy chain variable region comprising the three heavy chain CDRs of 18G1 and a humanized mature light chain variable region comprising the three light chain CDRs of 18G1.

In some such antibodies, the CDRs are as defined by Kabat/Chothia Composite, for example, SEQ ID NOS: 4, 5 and 6 for the heavy chain CDRs and SEQ ID NOs: 8, 9 and 10 for the light chain CDRs. In some such antibodies, the CDRs are of a definition selected from the group of Kabat, Chothia, Kabat/Chothia Composite, AbM and Contact.

For example, the antibody can be 18G1 or a chimeric, veneered, or humanized form thereof.

In some such antibodies, the humanized mature heavy chain variable region comprises the three Kabat heavy chain CDRs of 18G1 (CDR-H1 residues 6-10 of SEQ ID NO:4; CDR-H2 SEQ ID NO: 5, CDR-H3 SEQ ID NO:6) and the humanized mature light chain variable region comprises the three Kabat light chain CDRs of 18G1 (SEQ ID NOs: 8-10).

In some such antibodies, the humanized mature heavy chain variable region comprises the three Chothia heavy chain CDRs of 18G1 (CDR-H1 residues 1-7 of SEQ ID NO:4; CDR-H2 residues 3-8 of SEQ ID NO: 5, CDR-H3 SEQ ID NO:6) and the humanized mature light chain variable region comprises the three Chothia light chain CDRs of 18G1 (SEQ ID NOs: 8-10).

In some such antibodies, the humanized mature heavy chain variable region comprises the three AbM heavy chain CDRs of 18G1 (CDR-H1 SEQ ID NO:4; CDR-H2 residues 1-10 of SEQ ID NO: 5, CDR-H3 SEQ ID NO:6) and the humanized mature light chain variable region comprises the three AbM light chain CDRs of 18G1 (SEQ ID NOs: 8-10).

In some such antibodies, the humanized mature heavy chain variable region comprises the three Contact heavy chain CDRs of 18G1 (CDR-H1 residues 30-35 of SEQ ID:3; CDR-H2 residues 47-59 of SEQ ID NO: 3, CDR-H3 residues 97-108 of SEQ ID NO:3) and the humanized mature light chain variable region comprises the three Contact light chain CDRs of 18G1 (CDR-L1 residues 30-36 of SEQ ID:36; CDR-L2 residues 46-55 of SEQ ID NO: 36, CDR-L3 residues 89-96 of SEQ ID NO:36).

In some antibodies, the humanized mature heavy chain variable region has an amino acid sequence at least 90% identical to any one of SEQ ID NO:34-35 and the humanized mature light chain variable region has an amino acid sequence at least 90% identical to any one of SEQ ID NO: 37-39.

In some antibodies, at least one of the following positions is occupied by the amino acid as specified: position L3 is occupied by V, position L10 is occupied by S, position L13 is occupied by V, position L15 is occupied by P, position L19 is occupied by A, position L20 is occupied by S, position L22 is occupied by S, position L42 is occupied by Q, position L70 is occupied by D, position L77 is occupied by R, position L78 is occupied by V, position L80 is occupied by A, and position L85 is occupied by V.

In some antibodies, at least one of the following positions is occupied by the amino acid as specified: position L3 is occupied by V, position L10 is occupied by S, position L13 is occupied by V, position L15 is occupied by P, position L19 is occupied by A, position L20 is occupied by S, position L22 is occupied by S, position L24 is occupied by K, position L28 is occupied by N, position L29 is occupied by V, position L42 is occupied by Q, position L46 is occupied by L, position L70 is occupied by D, position L77 is occupied by R, position L78 is occupied by V, position L80 is occupied by A, and position L85 is occupied by V.

In some antibodies, positions L3, L10, L13, L15, L19, L20, L22, L42, L70, L77, L78, L80, and L85 are occupied by V, S, V, P, A, S, S, Q, D, R, V, A, and V, respectively.

In some antibodies, at least one of the following positions is occupied by the amino acid as specified: position H1 is occupied by E or Q, position H5 is occupied by V or Q, position H13 is occupied by Q or K, position H19 is occupied R or K, position H40 is occupied by A or T, position H42 is occupied by G or D, position H44 is occupied G or R, position H49 is occupied by S or A, position H77 is occupied by S or T, position H82a is occupied by N or S, position H83 is occupied by R or K, position H84 is occupied by A or S, position H89 is occupied by V or M, H93 is occupied by V or A, position H108 is occupied by T or M, position L45 is occupied by Q, position L60 is occupied by D, and position L83 is occupied by L.

In some antibodies, at least one of the following positions is occupied by the amino acid as specified: position H1 is occupied by E or Q, position H5 is occupied by V or Q, position H13 is occupied Q or K, position H19 is occupied R or K, position H40 is occupied by A or T, position H42 is occupied by G or D, position H44 is occupied G or R, position H49 is occupied by S or A, position H50 is occupied by G, position 63 is occupied by T, position H77 is occupied by S or T, position H82a is occupied by N or S, position H83 is occupied by R, position H84 is occupied by A, position H89 is occupied by V or M, H93 is occupied by V or A, position H108 is occupied by T or M.

In some antibodies, positions H1, H5, H13, H19, H40, H42, H44, H49, H77, H82a, H83, H84, H89, H93, and H108 are occupied by, E, V, Q, R, A, G, G, S, S, N, R, A, V, V, and T, respectively.

In some antibodies, at least one of the positions L45, L60, and L83 are occupied by Q, D, and L, respectively. In some such antibodies, position L45 is occupied by Q. In some such antibodies, positions L60 and L83 are occupied by D and L, respectively.

In some antibodies, the mature heavy chain variable region has an amino acid sequence at least 95% identical to any one of SEQ ID NO: 34-35 and the mature light chain variable region has an amino acid sequence at least 95% identical to any one of SEQ ID NO: 38-39. In some antibodies, the mature heavy chain variable region has an amino acid sequence at least 98% identical to any one of SEQ ID NO: 34-35 and the mature light chain variable region has an amino acid sequence at least 98% identical to any one of SEQ ID NO: 38-39.

In some antibodies, the mature heavy chain variable region has an amino acid sequence of any of SEQ ID NO:34-35 and the mature light chain variable region has an amino acid sequence of any one of SEQ ID NO:38-39. In some antibodies, the mature heavy chain variable region has an amino acid sequence of SEQ ID NO:34 and the mature light chain variable region has an amino acid sequence of SEQ ID NO:38. In some antibodies, the mature heavy chain variable region has an amino acid sequence of SEQ ID NO:34 and the mature light chain variable region has an amino acid sequence of SEQ ID NO:39. In some antibodies, the mature heavy chain variable region has an amino acid sequence of SEQ ID NO:35 and the mature light chain variable region has an amino acid sequence of SEQ ID NO:38. In some antibodies, the mature heavy chain variable region has an amino acid sequence of SEQ ID NO:35 and the mature light chain variable region has an amino acid sequence of SEQ ID NO:39.

Additional antibodies comprise three light chain CDRs and three heavy chain CDRs of monoclonal antibody 6B3, such as the mouse antibody characterized by a heavy chain variable region having an amino acid sequence comprising SEQ ID NO: 11 and a light chain variable region having an amino acid sequence comprising SEQ ID NO: 29. In some such antibodies, the CDRs are as defined by Kabat/Chothia Composite, for example, SEQ ID NOs: 12, 13 and 14 for the heavy chain CDRs and SEQ ID NOs: 16, 17 and 18 for the light chain CDRs.

For example, the antibody can be 6B3 or a chimeric, veneered, or humanized form thereof.

Some antibodies are a humanized or chimeric 6B3 antibody that specifically binds to human medin, wherein 6B3 is a mouse antibody characterized by a mature heavy chain variable region of SEQ ID NO:11 and a mature light chain variable region of SEQ ID NO: 29.

Some antibodies comprise a humanized mature heavy chain variable region comprising the three heavy chain CDRs of 6B3 and a humanized mature light chain variable region comprising the three light chain CDRs of 6B3.

In some such antibodies, the CDRs are of a definition selected from the group of Kabat, Chothia, Kabat/Chothia Composite, AbM and Contact.

In some such antibodies, the humanized mature heavy chain variable region comprises the three Kabat/Chothia Composite heavy chain CDRs of 6B3 (SEQ ID NOs: 12-14) and the humanized mature light chain variable region comprises the three Kabat/Chothia Composite light chain CDRs of 6B3 (SEQ ID NOs: 16-18).

In some such antibodies, the humanized mature heavy chain variable region comprises the three Kabat heavy chain CDRs of 6B3 (CDR-H1 residues 6-12 of SEQ ID NO:12; CDR-H2 SEQ ID NO: 13, CDR-H3 SEQ ID NO:14) and the humanized mature light chain variable region comprises the three Kabat light chain CDRs of 6B3 (SEQ ID NOs: 16-18).

In some such antibodies, the humanized mature heavy chain variable region comprises the three Chothia heavy chain CDRs of 6B3 (CDR-H1 residues 1-9 of SEQ ID NO:12; CDR-H2 residues 3-7 of SEQ ID NO: 13, CDR-H3 SEQ ID NO:14) and the humanized mature light chain variable region comprises the three Chothia light chain CDRs of 6B3 (SEQ ID NOs: 16-18).

In some such antibodies, n the humanized mature heavy chain variable region comprises the three AbM heavy chain CDRs of 6B3 (CDR-H1 SEQ ID NO:12; CDR-H2 residues 1-9 of SEQ ID NO: 13, CDR-H3 SEQ ID NO:14) and the humanized mature light chain variable region comprises the three AbM light chain CDRs of 6B3 (SEQ ID NOs: 16-18).

In some such antibodies, the humanized mature heavy chain variable region comprises the three Contact heavy chain CDRs of 6B3 (CDR-H1 residues 30-37 of SEQ ID NO:11; CDR-H2 residues 49-60 of SEQ ID NO: 11, CDR-H3 residues 98-106 of SEQ ID NO:11) and the humanized mature light chain variable region comprises the three Contact light chain CDRs of 6B3 (CDR-L1 residues 30-36 of SEQ ID:29; CDR-L2 residues 46-55 of SEQ ID NO: 29, CDR-L3 residues 89-96 of SEQ ID NO:29).

In some antibodies, the humanized mature heavy chain variable region has an amino acid sequence at least 90% identical to any one of SEQ ID NO:26-28 and the humanized mature light chain variable region has an amino acid sequence at least 90% identical to any one of SEQ ID NO: 31-32.

In some antibodies, at least one of the following positions is occupied by the amino acid as specified: H3 is occupied by Q, H5 is occupied by Q, H10 is occupied by G, H15 is occupied by S, and H19 is occupied by S.

In some antibodies, positions H3, H5, H10, H15, and H19 are occupied by, Q, Q, G, S, and S respectively.

In some antibodies, at least one of the following positions is occupied by the amino acid as specified: position: H1 is occupied by E or Q, H44 is occupied by G, H48 is occupied by I or L, H49 is occupied by G or A, H67 is occupied by V or L, H78 is occupied by F or V, H79 is occupied by S or V, H81 is occupied by K or T, H82 is occupied by L or M, H82a is occupied by S or T, H82b is occupied by S or N, H82c is occupied by V or M, H83 is occupied by T or D, H84 is occupied by A or P, H85 is occupied by A or V, H89 is occupied by V or T, H108 is occupied by T or L, L71 is occupied by Y or F, L87 is occupied by F or Y, L100 is occupied by Q or G, and L104 is occupied by L or V.

In some antibodies, at least one of the following positions is occupied by the amino acid as specified: position: H1 is occupied by E or Q, H35 is occupied by G, H35b is occupied by G, H44 is occupied by G or A, H48 is occupied by I or L, H49 is occupied by G or A, H50 is occupied by H, H58 is occupied by Y, H60 is occupied by N, H61 is occupied by I, H62 is occupied by A, H65 is occupied by N, H67 is occupied by V or L, H78 is occupied by F or V, H79 is occupied by S or V, H81 is occupied by K or T, H82 is occupied by L or M, H82a is occupied by S or T, H82b is occupied by S or N, H82c is occupied by V or M, H83 is occupied by T or D, H84 is occupied by A or P, H85 is occupied by A or V, H89 is occupied by V or T, H102 is occupied by Y, H108 is occupied by T or L, L71 is occupied by Y or F, L87 is occupied by F or Y, L100 is occupied by Q or G, and L104 is occupied by L or V.

In some antibodies, positions H1, H44, H79, H81, H82, H82b, H82c, H83, H84, H85, and H89 are occupied by, E, G, S, K, L, S, V, T, A, A, and V, respectively.

In some antibodies, positions H48, H49, H67, H78, H82a, and H108 are occupied by, I, G, V, F, S, and T, respectively.

In some antibodies, positions L71, L87, L100, and L104 are occupied by Y, F, Q, and L, respectively.

Some antibodies comprise a mature heavy chain variable region having an amino acid sequence at least 95% identical to at least one of SEQ ID NO: 26-28 and a mature light chain variable region having an amino acid sequence at least 95% identical to at least one of SEQ ID NO: 31-32.

Some antibodies comprise a mature heavy chain variable region having an amino acid sequence at least 98% identical to SEQ ID NO: 26-28 and a mature light chain variable region having an amino acid sequence at least 98% identical to SEQ ID NO: 31-32.

In some antibodies, the mature heavy chain variable region has an amino acid sequence of any of SEQ ID NO:26-28 and the mature light chain variable region has an amino acid sequence of any one of SEQ ID NO:31-32.

In some antibodies, the mature heavy chain variable region has an amino acid sequence of SEQ ID NO:26 and the mature light chain variable region has an amino acid sequence of SEQ ID NO:31. In some antibodies, the mature heavy chain variable region has an amino acid sequence of SEQ ID NO:26 and the mature light chain variable region has an amino acid sequence of SEQ ID NO:32. In some antibodies, the mature heavy chain variable region has an amino acid sequence of SEQ ID NO:27 and the mature light chain variable region has an amino acid sequence of SEQ ID NO:31. In some antibodies, the mature heavy chain variable region has an amino acid sequence of SEQ ID NO:27 and the mature light chain variable region has an amino acid sequence of SEQ ID NO:32. In some antibodies, the mature heavy chain variable region has an amino acid sequence of SEQ ID NO:28 and the mature light chain variable region has an amino acid sequence of SEQ ID NO:31. In some antibodies, the mature heavy chain variable region has an amino acid sequence of SEQ ID NO:28 and the mature light chain variable region has an amino acid sequence of SEQ ID NO:32.

The antibody can be an intact mouse, chimeric, veneered or humanized antibody or a binding fragment, single-chain antibody Fab fragment, Fab'2 fragment, or single chain Fv. Some of the antibodies have a human IgG1 isotype, while others may have a human IgG2 or IgG4 isotype. Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region.

Some antibodies may have at least one mutation in the constant region, such as a mutation that reduces complement fixation or activation by the constant region, for example, a mutation at one or more of positions 241, 264, 265, 270, 296, 297, 318, 320, 322, 329 and 331 by EU numbering. Some antibodies have an alanine at positions 318, 320 and 322. Some antibodies can be at least 95% w/w pure. The antibody can be conjugated to a therapeutic or cytotoxic agent.

In another aspect, the invention provides a pharmaceutical composition comprising any of the antibodies disclosed herein and a pharmaceutically-acceptable carrier.

In another aspect, the invention provides a nucleic acid encoding the heavy chain and/or light chain of any of the antibodies disclosed herein, a recombinant expression vector comprising the nucleic acid and a host cell transformed with the recombinant expression vector.

In yet another aspect, the invention provides methods of humanizing any non-human antibody described herein, for example, mouse antibodies 18G1 or 6B3. Such methods can involve selecting one or more acceptor antibodies, synthesizing a nucleic acid encoding a humanized heavy chain comprising CDRs of the mouse heavy chain and a nucleic acid encoding a humanized light chain comprising CDRs of the mouse antibody light chain, and expressing the nucleic acids in a host cell to produce a humanized antibody.

Methods of producing antibodies, such as a humanized, chimeric or veneered antibody, for example humanized, chimeric or veneered forms of 18G1 or 6B3, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

Some cells can be propagated under selective conditions and screened for cell lines naturally expressing and secreting at least 100 mg/L/$10^6$ cells/24 hours. Single cells can be isolated from the selected cells. Cells cloned from a single cell can then be banked. Single cells can be selected based on desirable properties, such as the yield of the antibody. Exemplary cell lines are cell lines expressing 18G1 or 6B3.

The invention also provides methods of inhibiting or reducing aggregation of medin in a subject having or at risk of developing a medin-mediated amyloidosis, comprising administering to the subj ect an effective regime of an antibody disclosed herein, thereby inhibiting or reducing aggregation of medin in the subject. An example of amyloidosis is aortic medial amyloid. Exemplary antibodies include humanized versions of 6B3 and 18G1.

Also provided are methods of treating or effecting prophylaxis of a disease associated with medin, medin aggregation or deposition in a subject, comprising administering an effective regime of an antibody disclosed herein and thereby treating or effecting prophylaxis of the disease. Examples of such a disease include pancreatitis, lupus, Alzheimer's disease, obesity, cardiac disease, Marfan syndrome, aortic aneurysm, atheroma, atherosclerosis, hypertension, vein thrombosis, varicose veins, an inflammatory condition affecting the vascular system, and a granulomatous disease. An example of an inflammatory condition affecting the vascular system is giant cell arteritis. Examples of a cardiac disease include myocardial infarction and coronary artery disease. An example of a granulomatous disease is a non-infectious granulomatous disease. Examples of such a granulomatous disease include sarcoidosis, Crohn's disease, berylliosis, granulomatosis with polyangiitis, Churg-Strauss syndrome, rheumatic fever, rheumatoid arthritis, granuloma annulare, vasculitis, foreign-body granulomapulmonary rheumatoid nodules and aspiration of food and other particulate material into the lung. An example of a granulomatous disease is a granulomatous disease chracterized by granulomas seen in an infectious disease. Examples of such an infectious disease include tuberculosis, leprosy, schistosomiasis, histoplasmosis, cryptococcosis, coccidioidomycosis, blastomycosis, listeria monoctogenes, pneumocystis pneumonia, aspiration pneumonia, and cat scratch disease.

Some methods involve a subject that has been diagnosed with Marfan syndrome. Some subjects have one or more risk factors for an aortic aneurysm, such as, for example, smoking, hypertension, atherosclerosis, bicuspid aortic valves and genetic connective disorders. In some methods, the disease is aortic aneurysm.

The invention also provides methods of reducing aortic medial amyloid formation in a subject having or at risk of an aortic aneurysm, comprising administering to the subject an effective amount of an antibody disclosed herein, thereby reducing aortic medial amyloid formation in the subject.

Also provided are methods of inhibiting medin aggregation or reducing aortic medial amyloid in a subject having or at risk of an aortic aneurysm, comprising administering to the subject an effective amount of an antibody disclosed herein, thereby inhibiting medin aggregation or reducing aortic medial amyloid in the subject. For example, the antibody can be a humanized version of 18G1 or 6B3.

The invention also provides a method of improving elasticity of the aorta in subjects having aortic medial amyloid, comprising administering to the subject an effective amount of an antibody disclosed herein, thereby improving the elasticity of the aorta of the subject. Some subjects have aortic medial amyloid in the thoracic aorta.

In another aspect, the invention provides a method of detecting aortic medial amyloid in a subject having or at risk of a disease associated with medin aggregation or deposition, comprising administering to the subject an effective amount of an antibody disclosed herein, wherein the antibody binds to aortic medial amyloid, and detecting bound antibody in the subject.

BRIEF DESCRIPTION OF THE DRAWINGS

The patent or application file contains at least on drawing executed in color. Copies of this patent or patent application publication with color drawing(s) will be provided by the Office upon request and payment of the necessary fee.

FIG. 1A & FIG. 1B: FIG. 1A depicts the position of medin within lactadherin. FIG. 1B depicts the amino acid sequence of full length human medin (SEQ ID NO:1) and peptides derived from C-terminal human medin (SEQ ID NO:2) and from C-terminal murine medin (SEQ ID NO:22).

FIG. 2A & FIG. 2B: FIG. 2A depicts binding curves of murine antibody 6B3 to lactadherin, full length medin, and peptides derived from C-terminal human and murine medin. FIG. 2B depicts binding curves of murine antibody 18G1 to lactadherin, full length medin, and peptides derived from C-terminal human and murine medin.

FIG. 3A depicts a Western blot analysis of a commercial lactadherin antibody binding to human lactadherin, but not to the medin peptide. FIG. 3B depicts a Western blot analysis of murine antibody 6B3 binding to human lactadherin and medin peptide.

FIG. 4A depicts a Western blot analysis of murine antibody 6B3 binding to human lactadherin and medin peptide. FIG. 4B depicts a Western blot analysis of murine antibody 18G1 binding to human medin peptide, but not to lactadherin.

FIG. 7 depicts an alignment of heavy chain variable regions of the mouse 6B3 antibody, human acceptor antibody, and humanized versions of the 6B3 antibody. The CDRs as defined by Kabat/Chothia Composite are enclosed in boxes.

FIG. 9 depicts an alignment of heavy chain variable regions of the mouse 18G1 antibody, human acceptor antibody, and humanized versions of the 18G1 antibody. The CDRs as defined by Kabat/Chothia Composite are enclosed in boxes.

FIG. 10 depicts an alignment of light chain variable regions of the mouse 18G1 antibody, human acceptor antibody, and humanized versions of the 18G1 antibody. The CDRs as defined by Kabat are enclosed in boxes.

FIGS. 11A-D show exemplary humanized 6B3 Vh designs, with backmutations and other mutations based on selected human frameworks. The gray-shaded areas indicate the CDRs as defined by Kabat/Chothia Composite.

FIGS. 12A-D show exemplary humanized 6B3 Vk designs, with backmutations and other mutations based on selected human frameworks. The gray-shaded areas indicate the CDRs as defined by Kabat/Chothia Composite.

FIGS. 13A-D show exemplary humanized 18G1 Vh designs, with backmutations and other mutations based on selected human frameworks. The gray-shaded areas indicate the CDRs as defined by Kabat/Chothia Composite.

FIGS. 14A-D show exemplary 18G1 Vk designs, with backmutations and other mutations bas(on selected human frameworks. The gray-shaded areas indicate the CDRs as defined by Kabat/Chothia Composite.

BRIEF DESCRIPTION OF THE SEQUENCES

SEQ ID NO: 1 sets forth the amino acid equence of human medin.

SEQ ID NO: 2 sets forth the amino acid sequence of a human C-terminal medin peptide immunogen.

SEQ ID NO: 3 sets forth the amino acid sequence of the heavy chain variable region of the mouse 18G1 antibody.

SEQ ID NO: 4 sets forth the amino acid sequence of Kabat/Chothia Composite CDR-H1 of the mouse 18G1 antibody.

SEQ ID NO: 5 sets forth the amino acid sequence of Kabat CDR-H2 of the mouse 18G1 antibody.

SEQ ID NO: 6 sets forth the amino acid sequence of Kabat CDR-H3 of the mouse 18G1 antibody.

SEQ ID NO: 7 sets forth the amino acid sequence of the light chain variable region of the mouse 18G1 antibody.

SEQ ID NO: 8 sets forth the amino acid sequence of Kabat CDR-L1 of the mouse 18G1 antibody.

SEQ ID NO: 9 sets forth the amino acid sequence of Kabat CDR-L2 of the mouse 18G1 antibody.

SEQ ID NO: 10 sets forth the amino acid sequence of Kabat CDR-L3 of the mouse 18G1 antibody.

SEQ ID NO: 11 sets forth the amino acid sequence of the heavy chain variable region of the mouse 6B3 antibody.

SEQ ID NO: 12 sets forth the amino acid sequence of Kabat/Chothia composite CDR-H1 of the mouse 6B3 antibody.

SEQ ID NO: 13 sets forth the amino acid sequence of Kabat CDR-H2 of the mouse 6B3 antibody.

SEQ ID NO: 14 sets forth the amino acid sequence of Kabat CDR-H3 of the mouse 6B3 antibody.

SEQ ID NO: 15 sets forth the amino acid sequence of the light chain variable region of the mouse 6B3 antibody.

SEQ ID NO: 16 sets forth the amino acid sequence of Kabat CDR-L1 of the mouse 6B3 antibody.

SEQ ID NO: 17 sets forth the amino acid sequence of Kabat CDR-L2 of the mouse 6B3 antibody.

SEQ ID NO: 18 sets forth the amino acid sequence of Kabat CDR-L1 of the mouse 6B3 antibody.

SEQ ID NO: 19 sets forth the nucleic acid sequence of a CK3' primer for VL PCR amplification of the medin antibody kappa light chains.

SEQ ID NO: 20 sets forth the nucleic acid sequence of a 3' primer for VH PCR amplification of the 18G1 antibody heavy chain.

SEQ ID NO: 21 sets forth the nucleic acid sequence of a 3' primer for VH PCR amplification of the 6B3 antibody heavy chain.

SEQ ID NO: 22 sets forth the amino acid sequence of a mouse C-terminal medin peptide immunogen.

Figure 5:
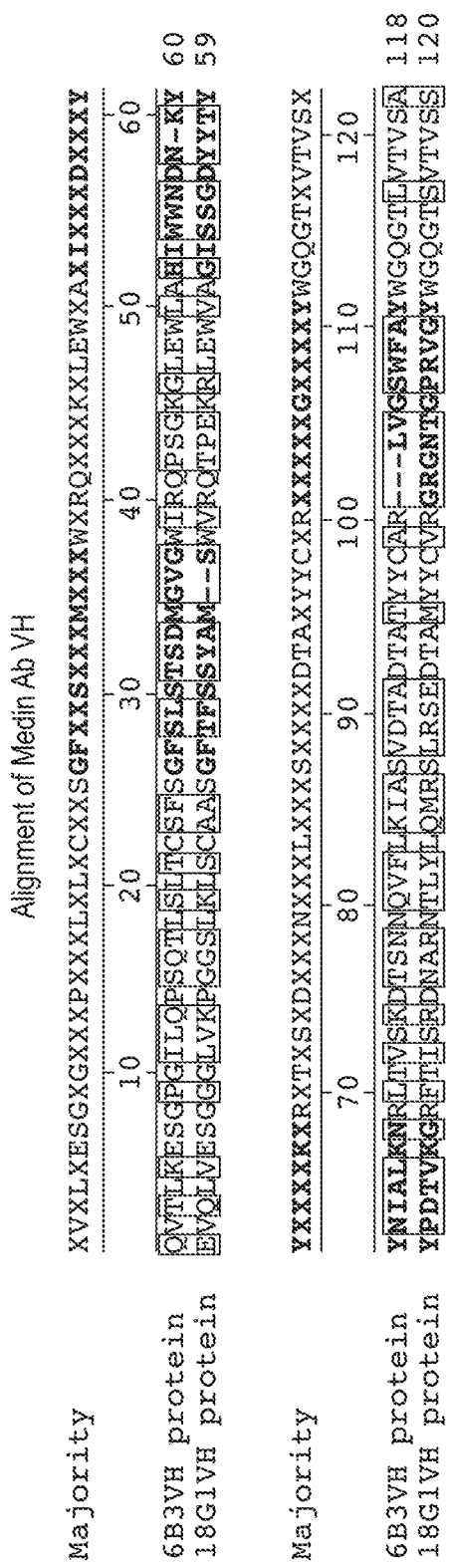
FIG. 5 depicts an alignment of heavy chain variable regions of the murine antibodies 6B3 and 18G1. The 6B3VH protein sequence is SEQ ID NO:11, and the 18G1VH protein sequence is SEQ ID NO:3. The consensus amino acid sequence between the heavy chain variable regions of the 6B3 and 18G1 mouse antibodies (labeled "Majority') is SEQ ID NO:23. The CDRs as defined by Kabat/Chothia Composite are in boldface. Positions where amino acid residues differ between the heavy chain variable regions of murine antibody 6B3 and murine antibody 18G1 are boxed.

SEQ ID NO:23 sets forth the consensus amino acid sequence between the heavy chain variable regions of the 6B3 and 18G1 mouse antibodies (labeled "Majority' in FIG. 5).

Figure 6:
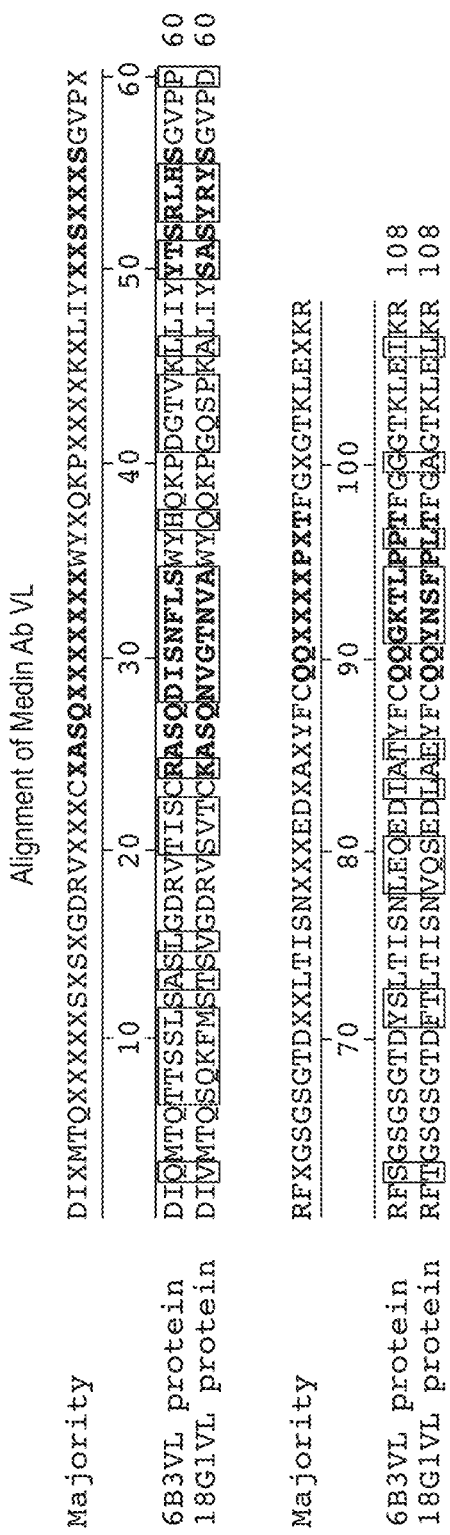
FIG. 6 depicts an alignment of light chain variable regions of the murine antibodies 6B3 and 18G1. The 6B3VL protein sequence is SEQ ID NO:15, and the 18G1VL protein sequence is SEQ ID NO:7. The consensus amino acid sequence between the light chain variable regions of the 6B3 and 18G1 mouse antibodies (labeled "Majority') is SEQ ID NO:24. The CDRs as defined by Kabat are in boldface. Positions where amino acid residues differ between the light chain variable regions of murine antibody 6B3 and murine antibody 18G1 are boxed.

SEQ ID NO:24 sets forth the consensus amino acid sequence between the light chain variable regions of the 6B3 and 18G1 mouse antibodies (labeled "Majority' in FIG. 6).

SEQ ID NO:25 sets forth the amino acid sequence of the heavy chain variable acceptor Acc. #AAD53863.1.

SEQ ID NO:26 sets forth the amino acid sequence of heavy chain variable region of the humanized 6B3 antibody version 1 (Hu6B3VHv1).

SEQ ID NO:27 sets forth the amino acid sequence of the heavy chain variable region of the humanized 6B3 antibody version 2 (Hu6B3VHv2).

SEQ ID NO:28 sets forth the amino acid sequence of the heavy chain variable region of the humanized 6B3 antibody version 1 (Hu6B3VHv3).

SEQ ID NO: 29 sets forth the amino acid sequence of the light chain variable region of the mouse 6B3 antibody minus the C-terminal arginine found in SEQ ID NO:15.

SEQ ID NO:30 sets forth the amino acid sequence of the light chain variable acceptor Acc. #BAC01558.1.

SEQ ID NO:31 sets forth the amino acid sequence of the light chain variable region of the humanized 6B3 antibody version 1 (Hu6B3VLv1).

SEQ ID NO:32 sets forth the amino acid sequence of the light chain variable region of the humanized 6B3 antibody version 2 (Hu6B3VLv2).

SEQ ID NO:33 sets forth the amino acid sequence of the heavy chain variable acceptor Acc. #AAX82494.1.

SEQ ID NO:34 sets forth the amino acid sequence of heavy chain variable region of the humanized 18G1antibody version 1 (Hu18G1VHv1).

SEQ ID NO:35 sets forth the amino acid sequence of the heavy chain variable region of the humanized 18G1 antibody version 2 (Hu18G1VHv2).

SEQ ID NO: 36 sets forth the amino acid sequence of the light chain variable region of the mouse 18G1 antibody minus the C-terminal arginine found in SEQ ID NO:7.

SEQ ID NO:37 sets forth the amino acid sequence of the light chain variable acceptor Acc. #AAD39507.1.

SEQ ID NO:38 sets forth the amino acid sequence of the light chain variable region of the humanized 18G1antibody version 1 (Hu18G1VLv1).

SEQ ID NO:39 sets forth the amino acid sequence of the light chain variable region of the humanized 18G1 antibody version 2 (Hu18G1VLv2).

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3

The assignment of amino acids to each VL and VH domain is in accordance with any conventional definition of CDRs. Conventional definitions include, the Kabat definition (Kabat, Sequences of Proteins of Immunological Interest (National Institutes of Health, Bethesda, Md., 1987 and 1991), the Chothia definition (Chothia & Lesk, J. Mol. Biol. 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modeling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
| --- | --- | --- | --- | --- | --- |
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 . . . H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.*, 79:315-321 (1990); Kostelny et al., *J. Immunol.*, 148:1547-53 (1992)). In some bispecific antibodies, the two different heavy/light chain pairs include a humanized 6B3 or 18G1 heavy chain/light chain pair and a heavy chain/light chain pair specific for a different epitope on medin than that bound by 6B3 or 18G1.

In some bispecific antibodies, one heavy chain/light chain pair is a humanized 6B3 or 18G1 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distributioin in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include disease affected cells. Control samples can be obtained from individuals not afflicted with the disease. Alternatively, control samples can be obtained from patients afflicted with the disease. Such samples can be obtained at the same time as a biological sample thought to comprise the disease or on a different occasion. A biological sample and a control sample can both be obtained from the same tissue). Preferably, control samples consist essentially or entirely of normal, healthy cells and can be used in comparison to a biological sample thought to comprise disease-affected cells. Preferably, the cells in the control sample have the same tissue origin as the cancer cells thought to be in the biological sample. Preferably, the cells thought to be in the biological sample arise from the same cell type as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as-values within a standard margin of error of measurement (e.g., SEM) of a stated value.

Statistical Significance Means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to medin. The antibodies have the capacity to bind to monomeric, misfolded, aggregated or fibril forms of medin. The antibodies can be used for treating or effecting prophylaxis of diseases or disorders associated with medin, medin accumulation or accumulation of medin deposits. For example, one approach to treat aortic aneurysms may be to sequester medin and thereby block aggregation or remove the amyloid deposits from the aorta using a monoclonal antibody. The antibodies can also be used for diagnosing medin amyloidosis and inhibiting or reducing aggregation of medin, among other applications.

II. Target Molecules

Medin is a 50 amino acid peptide, is formed by enzymatic cleavage of lactadherin and has the sequence of SEQ ID NO: 1. Lactadherin is a 364 amino acid glycoprotein also known as Milk Fat Globule-EGF Factor 8 (MFG-E8), SED1, PAS 6/7 and P47. Medin is cleaved by an unknown process and is thought to disrupt lactadherin anchoring of smooth muscle to elastin and thereby lead to reduced elasticity or "hardening" of the aortic artery. The main component of senile aortic amyloid deposits is medin (Haggqvist et al., PNAS 96:8669-8674 (1999). Research indicates that prefibrillar oligomeric aggregates of medin, rather than mature amyloid fibrils, are toxic to the surrounding cells (Peng et al., Lab Invest. 87:1195-1205 (2007). Unless otherwise apparent from context, reference to medin, lactadherin or their fragments includes the natural human amino acid sequences including isoforms, mutants, and allelic variants thereof.

III. Medin Amyloidosis

An accumulation of lactadherin occurs in the arterial wall during inflammatory remodeling seen with aging, hypertension, diabetes mellitus, or atherosclerosis. In the atrial wall, lactadherin signaling promotes vascular smooth muscle cell invasion, proliferation and the secretion of inflammatory molecules. Analysis of senile aortic amyloid deposits revealed that medin, an internal cleavage product of the C-terminal region of Lactadherin was the main component. Medin is thought to disrupt lactadherin anchoring of smooth muscle to elastin and thereby lead to reduced elasticity or "hardening" of the aortic artery. Medin amyloid deposits are very common in aortas of patients over age 55, with one report estimating an incidence of 97%. The highest prevalence of medin amyloid is seen in the thoracic aorta. This may be due to the high levels of elastin in these vessels. Deposits have been seen in the extra-cellular space in close proximity to elastin fibers. Medin is less abundant or has not been detected in other tissues where lactadherin is expressed.

Lactadherin and/or medin have also been implicated in Marfan syndrome (a genetic disease that affects the elastin fibers in the aorta and can eventually lead to an aneurysm), pancreatitis, lupus, Alzheimer's disease and obesity.

Aortic aneurysms are characterized by a reduction in the structural framework and strength of the aorta which can lead to a rupture, severe internal bleeding, and death. Thoracic aneurysms affect approximately 15,000 people in the US each year and only about 20-30% of patients who get to the hospital with a rupture survive. The most common type of aneurysms are degenerative in nature, with a progressive increase in vessel diameter and decrease in wall thickness. Risk factors for aneurysms include smoking, hypertension, atherosclerosis, bicuspid aortic valves, and genetic connective disorders.

Lactadherin and/or medin may also play a role in inflammatory conditions affecting the vascular system, e.g., of the vessel wall, e.g., GCA (giant cell arteritis), vasculitis, vein thrombosis, varicose veins.

Interestingly, as described in more detail in the Examples, applicant has discovered medin to be implicated in diseases associated with granulomas. Granuloma is an inflammation found in many diseases, both infectious and non-infectious. Infections characterized by granulomas include tuberculosis, leprosy, schistosomiasis, histoplasmosis, cryptococcosis, coccidioidomycosis, blastomycosis, Listeria monocytogenes, pneumocystis pneumonia and cat scratch disease. Examples of non-infectious granulomatous diseases are sarcoidosis, Crohn's disease, berylliosis, granulomatosis with polyangiitis, Churg-Strauss syndrome, rheumatic fever, rheumatoid arthritis, aspiration pneumona, granuloma annulare, vasculitis, pulmonary rheumatoid nodules and aspiration of food and other particulate material into the lung.

IV. Antibodies

A. Binding Specificity and Functional Properties

The invention provides monoclonal antibodies binding to epitopes within medin. Some such epitopes are buried in the native form of lactadherin and exposed in misfolded lactadherin. Some epitopes are neo-epitopes exposed upon cleavage of lactadherin to produce medin. Some epitopes are located at the C-terminal region of medin. The epitope can be linear, such as an epitope of 2-5, 3-5, 3-6, 3-7, 3-9, 4-9 or 5-9 contiguous amino acids from SEQ ID NO:1. Some epitopes are within SEQ ID NO:2. The epitope can be a conformational epitope, including, for example, two or more non-contiguous segments of amino acids within residues 1-50 of SEQ ID NO: 1. Antibodies designated 18G1 and 6B3 are two such exemplary mouse antibodies. The sequences of the heavy and light chain mature variable regions of these antibodies are designated SEQ ID NOs: 3 and 7, and 11 and 15 respectively. SEQ ID NO: 29 sets forth the amino acid sequence of the light chain variable region of the mouse 6B3 antibody minus the C-terminal arginine found in SEQ ID NO:15. SEQ ID NO: 36 sets forth the amino acid sequence of the light chain variable region of the mouse 18G1 antibody minus the C-terminal arginine found in SEQ ID NO:7. The C-terminal Arg in SEQ ID NO;7 and SEQ ID NO:29 is sometimes included when linking a variable region to a constant region. As described in detail in the Examples, antibodies were raised to full length medin or a C-terminal fragment of medin and screened by a number of laboratory techniques, including enzyme-linked immunosorbent assay (ELISA), Biacore analysis, Western blot analysis, and immunohistochemistry.

Some antibodies specifically bind to an epitope within residues 44-50 of medin (SEQ ID NO:1). One such antibody is 18G1 and its chimeric, veneered and humanized forms. Unless otherwise apparent from the context, reference to 18G1 should be understood as referring to any of the mouse, chimeric, veneered or humanized forms. A hybridoma cell line that produces monoclonal antibody 18G1 was deposited with the Patent Depository of the American Type Culture Collection (ATCC), Manassas, Va., 20110-2209 on Oct. 25, 2016 and assigned Patent Deposit No PTA-123560. 18G1 specifically binds the medin peptide and does not specifically bind lactadherin.

Some antibodies specifically bind to an epitope different than that of 18G1. For example, 6B3 and its chimeric, veneered and humanized forms bind within residues 1-50 of medin (SEQ ID NO:1). Unless otherwise apparent from the context, reference to 6B3 should be understood as referring to any of the mouse, chimeric, veneered or humanized forms. A hybridoma cell line that produces monoclonal antibody 6B3 was deposited with the Patent Depository of the American Type Culture Collection (ATCC), Manassas, Va., 20110-2209 on Oct. 25, 2016 and assigned Patent Deposit No. PTA-123559. 6B3 binds both full length medin peptide and synthetic lactadherin polypeptide in an ELISA and Western blot and does not bind the human medin C-terminal peptide (SEQ ID NO: 2). Interestingly, 6B3 does not bind lactadherin expressed on cells, suggesting that the medin region of lactadherin is likely hidden inside the native lactadherin molecule and only exposed when lactadherin is misfolded or denatured.

Some antibodies, such as, for example, 6B3 and 18G1, specifically bind monomeric, as well as multimeric and oligomeric forms of medin. Some antibodies specifically bind Thioflavin S positive structures such as dense aggregated material or amyloid deposits found in aneurysms (e.g., 6B3), while other antibodies do not (e.g., 18G1). Some antibodies specifically bind to loose fibrillar, Thioflavin S negative structures (e.g., 18G1). Some antibodies can diffusely stain the tunica media, the region of the aorta that contains the elastin fibers and smooth muscle cells (e.g., 18G1). Some antibodies can bind both aneurysm amyloid deposits and Thioflavin S negative loose fibrillar structures in proximity to Thiovlavin S positive structures (e.g., 6B3).

Some antibodies of the invention bind to the same or overlapping epitope as an antibody designated 6B3 or 18G1. Other antibodies having such a binding specificity can be produced by immunizing mice with medin or a portion thereof including the desired epitope, and screening resulting antibodies for binding to medin or fragments thereof, optionally in competition with 6B3 or 18G1. Antibodies identified by such assays can then be screened for binding specificity as described in the examples, or otherwise. Antibodies can also be screened for differential binding to wild-type medin or fragments thereof compared to mutagenized forms of the medin antigen. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout medin or through a section thereof in which an epitope is known to reside. If the same set of mutations significantly reduces the binding of two antibodies, the two antibodies bind the same epitope.

Antibodies having the binding specificity of a selected murine antibody (e.g., 6B3 or 18G1) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for medin (e.g., at least $10^8$ and preferably at least $10^9$ M$^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for medin are selected. The resulting antibodies usually have the same or similar epitope specificity as the murine starting material.

Kabat CDRs of the heavy chain of 6B3 are designated as follows: (CDR-H1: residues 6-12 of SEQ ID NO:12; CDR-H2 SEQ ID NO: 13, CDR-H3: SEQ ID NO:14); and Kabat CDRs of the light chain of 6B3 are designated SEQ ID NOs: 16-18, respectively. Kabat CDRs of the heavy chain of 18G1 are designated as follows: (CDR-H1: residues 6-10 of SEQ ID NO:4; CDR-H2: SEQ ID NO: 5, CDR-H3: SEQ ID NO:6) and Kabat CDRs of the light chain of 18G1 are designated SEQ ID NOs: 8-10, respectively.

Kabat/Chothia Composite CDRs of the heavy chain of 6B3 are designated SEQ ID NOs: 12-14, respectively, and Kabat/Chothia Composite CDRs of the light chain of 6B3 are designated SEQ ID NOs: 16-18, respectively. Kabat/Chothia Composite CDRs of the heavy chain of 18G1 are designated SEQ ID NOs:4-6, respectively, and Kabat/

Chothia Composite CDRs of the light chain of 18G1 are designated SEQ ID NOs 8-10, respectively.

Table 2 indicates the 18G1 CDRs as defined by Kabat, Chothia, Composite of Chothia and Kabat (also referred to herein as "Kabat/Chothia Composite"), AbM, and Contact. Table 3 indicates the 6B3 CDRs as defined by Kabat, Chothia, Composite of Chothia and Kabat (also referred to herein as "Kabat/Chothia Composite"), AbM, and Contact.

the invention. Monoclonal antibodies having at least 1, 2, 3, 4, 5 and preferably all six CDR(s) as defined by Kabat that are 90%, 95%, 99% or 100% identical to corresponding CDRs of 6B3 or 18G1 are also included.

The invention also provides antibodies having some or all (e.g., 3, 4, 5, and 6) CDRs entirely or substantially from 6B3 or 18G1. Such antibodies can include a heavy chain variable region that has at least two, and usually all three, CDRs

TABLE 2

18G1 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 SEQ ID NO: 8 | L24--L34 SEQ ID NO: 8 | L24--L34 SEQ ID NO: 8 | L24--L34 SEQ ID NO: 8 | L30--L36 residues 30-36 of SEQ ID NO: 36 |
| L2 | L50--L56 SEQ ID NO: 9 | L50--L56 SEQ ID NO: 9 | L50--L56 SEQ ID NO: 9 | L50--L56 SEQ ID NO: 9 | L46--L55 residues 46-55 of SEQ ID NO: 36 |
| L3 | L89--L97 SEQ ID NO: 10 | L89--L97 SEQ ID NO: 10 | L89--L97 SEQ ID NO: 10 | L89--L97 SEQ ID NO: 10 | L89--L96 residues 89-96 of SEQ ID NO: 36 |
| H1 | H31--H35B residues 6-10 of SEQ ID NO: 4 | H26--H32 residues 1-7 of SEQ ID NO: 4 | H26--H35B SEQ ID NO: 4 | H26--H35B SEQ ID NO: 4 | H30--H35B residues 30-35 of SEQ ID NO: 3 |
| H2 | H50--H65 SEQ ID NO: 5 | H52--H56 residues 3-8 of SEQ ID NO: 5 | H50--H65 SEQ ID NO: 5 | H50--H58 residues 1-10 of SEQ ID NO: 5 | H47--H58 residues 47-59 of SEQ ID NO: 3 |
| H3 | H95--H102 SEQ ID NO: 6 | H95--H102 SEQ ID NO: 6 | H95--H102 SEQ ID NO: 6 | H95--H102 SEQ ID NO: 6 | H93--H101 residues 97-108 of SEQ ID NO: 3 |

TABLE 3

6B3 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 SEQ ID NO: 16 | L24--L34 SEQ ID NO: 16 | L24--L34 SEQ ID NO: 16 | L24--L34 SEQ ID NO: 16 | L30--L36 residues 30-36 of SEQ ID NO: 29 |
| L2 | L50--L56 SEQ ID NO: 17 | L50--L56 SEQ ID NO: 17 | L50--L56 SEQ ID NO: 17 | L50--L56 SEQ ID NO: 17 | L46--L55 residues 46-55 of SEQ ID NO: 29 |
| L3 | L89--L97 SEQ ID NO: 18 | L89--L97 SEQ ID NO: 18 | L89--L97 SEQ ID NO: 18 | L89--L97 SEQ ID NO: 18 | L89-L96 Residues 89-96 of SEQ ID NO: 29 |
| H1 | H31--H35B residues 6-12 of SEQ ID NO: 12 | H26--H34 residues 1-9 of SEQ ID NO: 12 | H26--H35B SEQ ID NO: 12 | H26--H35B SEQ ID NO: 12 | H30--H35B residues 30-37 of SEQ ID NO: 11 |
| H2 | H50--H65 SEQ ID NO: 13 | H52--H56 residues 3-7 of SEQ ID NO: 13 | H50--H65 SEQ ID NO: 13 | H50--H58 residues 1-9 of SEQ ID NO: 13 | H47--H58 residues 49-60 of SEQ ID NO: 11 |
| H3 | H95--H102 SEQ ID NO: 14 | H95--H102 SEQ ID NO: 14 | H95--H102 SEQ ID NO: 14 | H95--H102 SEQ ID NO: 14 | H93--H101 residues 98-106 of SEQ ID NO: 11 |

Other antibodies can be obtained by mutagenesis of cDNA encoding the heavy and light chains of an exemplary antibody, such as 6B3 or 18G1. Monoclonal antibodies that are at least 70%, 80%, 90%, 95%, 96%, 97%, 98%, or 99% identical to 6B3 or 18G1 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in entirely or substantially from the heavy chain variable region of 6B3 or 18G1 and/or a light chain variable region having at least two, and usually all three, CDRs entirely or substantially from the light chain variable region of 6B3 or 18G1. The antibodies can include both heavy and light chains. A CDR is substantially from a corresponding CDR when it contains no more than 4, 3, 2, or 1 insertions, or deletions, except that CDRH2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 6B3 or 18G1 in the amino acid sequence of the mature heavy and/or light chain variable regions and maintain their functional properties, and/or differ from 6B3 or 18G1 by a small number of functionally inconsequential amino acid substitutions (e.g., conservative substitutions), deletions, or insertions.

B. Non-Human Antibodies

The production of other non-human antibodies, e.g., murine, guinea pig, primate, rabbit or rat, against medin can be accomplished by, for example, immunizing the animal with medin or a fragment thereof, such as, for example a peptide having the amino acid sequence of SEQ ID NO: 2 or SEQ ID NO: 22. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to medin or desired fragments thereof. Such screening can be accomplished by determining binding of an antibody to a collection of medin variants, and determining which medin variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.*, 320: 415-428, 2002; Iwahashi et al., *Mol. Immunol.* 36:1079-1091, 1999; Tamura et al, *J. Immunol.*, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the heavy chain is the human mature heavy chain variable region with NCBI accession code AAD53863.1 (SEQ ID NO: 25). This acceptor includes CDRs CDR-H1 and CDR-H2 having the same canonical form as mouse 6B3 heavy chain and is a member of Kabat human heavy subgroup 1. An example of an acceptor sequence for the light chain is the human mature light chain variable region with NCBI accession code BAC01558.1 (SEQ ID NO: 25). This acceptor has the same canonical classes for CDR-L1 and CDR-L2 as does mouse 6B3. BAC01558.1 is a member of Kabat human kappa subgroup 2. An example of an acceptor sequence for the heavy chain is the human mature heavy chain variable region with NCBI accession code AAX82494.1 (SEQ ID NO: 33). This acceptor includes CDRs CDR-H1 and CDR-H2 having the same canonical form as mouse 18G1 heavy chain and is a member of Kabat human heavy subgroup 1. An example of an acceptor sequence for the light chain is the human mature light chain variable region with NCBI accession code AAD39507.1 (SEQ ID NO: 37). This acceptor has the same canonical classes for CDR-L1 and CDR-L2 as does mouse 18G1. AAD39507.1 is a member of Kabat human kappa subgroup 2.

If more than one human acceptor antibody sequence is selected, a composite or hybrid of those acceptors can be used, and the amino acids used at different positions in the humanized light chain and heavy chain variable regions can be taken from any of the human acceptor antibody sequences used.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion (Liu, Y. D., et al., 2011, J. Biol. Chem., 286: 11211-11217). Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control. Exemplary humanized antibodies with N-terminal glutamine to glutamate substitutions are Hu6B3VHv2 (SEQ ID NO:27), Hu6B3VHv3 (SEQ DI NO:28), and Hu18G1VHv2 (SEQ ID NO:39).

Exemplary humanized antibodies are humanized forms of the mouse medin antibodies, designated 6B3 and 18G1. The mouse 6B3 antibody comprises mature heavy and light chain variable regions having amino acid sequences comprising SEQ ID NO: 11 and SEQ ID NO: 29, respectively. The mouse 18G1 antibody comprises mature heavy and light chain variable regions having amino acid sequences comprising SEQ ID NO: 3 and SEQ ID NO:36, respectively.

Exemplary humanized antibodies are humanized forms of the mouse 6B3 or 18G1 antibodies, designated Hu6B3 or Hu18G1, respectively.

Figure 8:
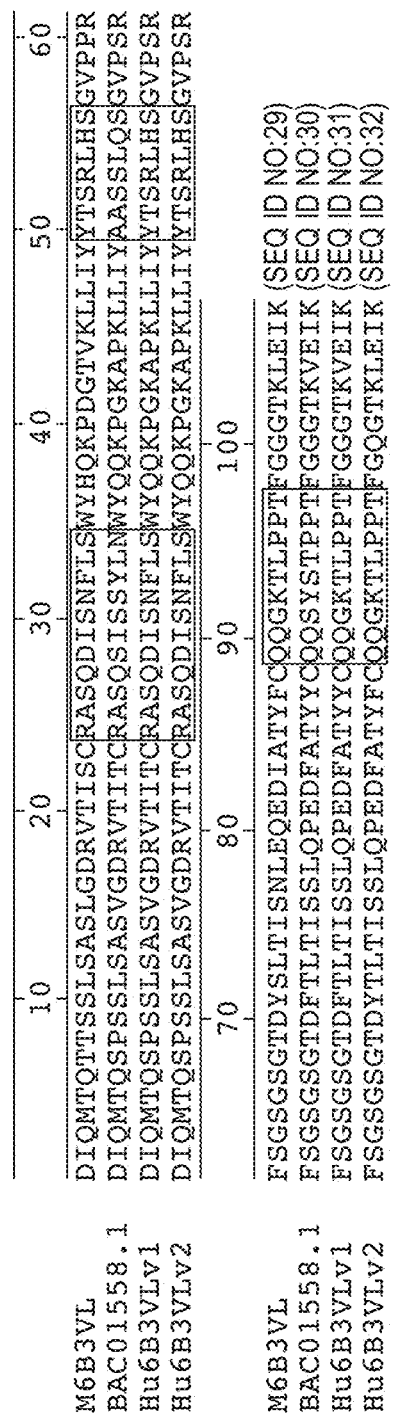
FIG. 8 depicts an alignment of light chain variable regions of the mouse 6B3 antibody, human acceptor antibody, and humanized versions of the 6B3 antibody. The CDRs as defined by Kabat are enclosed in boxes.

The mouse antibody 6B3 comprises mature heavy and light chain variable regions having amino acid sequences comprising SEQ ID NO: 11 and SEQ ID NO:29, respectively. The invention provides three exemplified humanized mature heavy chain variable regions: Hu6B3VHv1 (SEQ ID NO: 26), Hu6B3VHv2 (SEQ ID NO: 27), and Hu6B3VHv3 (SEQ ID NO: 28). The invention further provides two exemplified human mature light chain variable regions: Hu6B3VLv1 (SEQ ID NO: 31) and Hu6B3VLv2 (SEQ ID NO: 32) FIGS. 7 and 8 show alignments of the heavy chain variable region and light chain variable region, respectively, of mouse 6B3, human acceptor antibody, and various humanized antibodies.

The mouse antibody 18G1 comprises mature heavy and light chain variable regions having amino acid sequences comprising SEQ ID NO: 3 and SEQ ID NO:36, respectively. The invention provides two exemplified humanized mature heavy chain variable regions: Hu18G1VHv1 (SEQ ID NO: 34) and Hu18G1VHv2 (SEQ ID NO: 35). The invention further provides two exemplified human mature light chain variable regions: Hu18G1VLv1 (SEQ ID NO: 38) and Hu18G1VLv2 (SEQ ID NO: 39). FIGS. 9 and 10 show alignments of the heavy chain variable region and light chain variable region, respectively, of mouse 18G1, human acceptor antibody, and various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 26 variable region framework positions were considered as candidates for substitutions in the two exemplified Hu6B3 mature light chain variable regions and the three exemplified Hu6B3 mature heavy chain variable regions, as further specified in the examples: L71 (F71Y), L87 (Y87F), L100 (G100Q), L104 (V104L), H1 (Q1E), H3 (T3Q), H5 (K5Q), H10 (A10G), H15 (T15S), H19 (T19S), H44 (A44G), H48 (L48I), H49 (A49G), H67 (L67V), H78 (V78F), H79 (V79S), H81 (T81K), H82 (M82L), H82a (T82aS), H82b (N82bS), H82c (M82cV), H83 (D83T), H84 (P84A), H85 (V85A), H89 (T89V), and H108 (L108T). Likewise, the following 31 variable region framework positions were considered as candidates for substitutions in the two exemplified Hu18G1 mature light chain variable regions and the two exemplified Hu18G1 mature heavy chain variable regions, as further specified in the examples: L3 (Q3V), L10 (F10S), L13 (A13V), L15 (V15P), L19 (V19A), L20 (T20S), L22 (T22S), L42 (K42Q), L45 (K45Q), L60 (S60D), L70 (E70D), L77 (S77R), L78 (L78V), L80 (P80A), L83 (F83L), L85 (T85V), H1 (Q1E), H5 (Q5V), H13 (K13Q), H19 (K19R), H40 (T40A), H42 (D42G), H44 (R44G), H49 (A49S), H77 (T77S), H82a (S82aN), H83 (K83R), H84 (S84A), H89 (M89V), H93 (A93V), and H108 (M108T), Here, as elsewhere, the first-mentioned residue is the residue of a humanized antibody formed by grafting Kabat CDRs or a Chothia-Kabat Composite CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified Hu6B3 antibodies include any permutations or combinations of the exemplified mature heavy and light chain variable regions (e.g., VHv1NLv1 or H1L1, VHv1NLv2 or H1L2, VHv2/VLv1 or H2L1, VHv2/VLv2 or H2L2, VHv3/VLv1 or H3L1, VHv3/VLv2 or H3L2).

The invention provides variants of humanized 6B3 antibodies in which the humanized mature heavy chain variable region shows at least 90%, 95%, 96%, 97%, 98%, or 99% identity to any one of Hu6B3VHv1, Hu6B3VHv2 and Hu6B3VHv3 (SEQ ID NO: 26-28) and the humanized mature light chain variable region shows at least 90%, 95%, 96%, 97%, 98%, or 99% identity to Hu6B3VLv1 or Hu6B3VLv2 (SEQ ID NO: 31-32). In some such antibodies at least 1, 2, 3, 4, 5, 6, 7, 8, 9, 10, 11, 12, 13, 14, 15, 16, 17, 18, 19, 20, 21, 22, 23, 24, 25, or all 26 the backmutations or other mutations found in SEQ ID NO:26-28 and SEQ ID NO:31-32 are retained.

In some humanized 6B3 antibodies, at least one of the following positions in the VH region is occupied by the amino acid as specified: H3 is occupied by Q, H5 is occupied by Q, H10 is occupied by G, H15 is occupied by S, and H19 is occupied by S. In some antibodies, positions H3, H5, H10, H15, and H19 in the VH region are occupied by, Q, Q, G, S, and S respectively In some humanized 6B3 antibodies, at least one of positions in the VH region is occupied by the amino acid as specified: position: H1 is occupied by E or Q, H44 is occupied by G, H48 is occupied by I or L, H49 is occupied by G or A, H67 is occupied by V or L, H78 is occupied by F or V, H79 is occupied by S or V, H81 is occupied by K or T, H82 is occupied by L or M, H82a is occupied by S or T, H82b is occupied by S or N, H82c is occupied by V or M, H83 is occupied by T or D, H84 is occupied by A or P, H85 is occupied by A or V, H89 is occupied by V or T, H108 is occupied by T or L, L71 is occupied by Y or F, L87 is occupied by F or Y, L100 is occupied by Q or G, and L104 is occupied by L or V.

In some humanized 6B3 antibodies, at least one of the following positions in the VH region is occupied by the amino acid as specified: H1 is occupied by E or Q, H35 is occupied by G, H35b is occupied by G, H44 is occupied by G or A, H48 is occupied by I or L, H49 is occupied by G or A, H50 is occupied by H, H58 is occupied by Y, H60 is occupied by N, H61 is occupied by I, H62 is occupied by A, H65 is occupied by N, H67 is occupied by V or L, H78 is occupied by F or V, H79 is occupied by S or V, H81 is occupied by K or T, H82 is occupied by L or M, H82a is occupied by S or T, H82b is occupied by S or N, H82c is occupied by V or M, H83 is occupied by T or D, H84 is occupied by A or P, H85 is occupied by A or V, H89 is occupied by V or T, H102 is occupied by Y, H108 is occupied by T or L, L71 is occupied by Y or F, L87 is occupied by F or Y, L100 is occupied by Q or G, and L104 is occupied by L or V.

In some humanized 6B3 antibodies, positions H1, H44, H79, H81, H82, H82b, H82c, H83, H84, H85, and H89 in the VH region are occupied by, E, G, S, K, L, S, V, T, A, A, and V, respectively. In some humanized 6B3 antibodies, positions H3, H5, H10, H15, and H19 in the VH region are occupied by, Q, Q, G, S, and S respectively as in Hu6B3VHv1. In some humanized 6B3 antibodies, positions H1, H3, H5, H10, H15, H19, H44, H79, H81, H82, H82b, H82c, H83, H84, H85, H89 in the VH region are occupied by, E, Q, Q, G, S, S, G, S, K, L, S, V, T, A, A, and V, respectively, as in Hu6B3VHv2. In some humanized 6B3 antibodies, positions H1, H3, H5, H10, H15, H19, H44, H48, H49, H67, H78, H79, H81, H82, H82a, H82b, H82c, H83, H84, H85, H89, and H108 in the VH region are occupied by E, Q, Q, G, S, S, G, I, G, V, F, S, K, L, S, S, V, T, A, A, V, and T, respectively, as in Hu6B3VHv3. In some humanized 6B3 antibodies, positions L71, L87, L100, and L104 in the VL region are occupied by Y, F, Q, and L, respectively, as in Hu6B3VLv2.

The CDR regions of such humanized antibodies can be identical or substantially identical to the CDR regions of 6B3 mouse donor antibody. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu6B3 heavy and light chains by a small number (e.g., typically no more than 1, 2, 3, 5, 10, or 15) of replacements, deletions or insertions. Such differences are usually in the framework but can also occur in the CDRs.

Exemplified Hu18G1 antibodies include any permutations or combinations of the exemplified mature heavy and light chain variable regions (e.g., VHv1/VLv1 or H1L1, VHv1/VLv2 or H1L2, VHv2/VLv1 or H2L1, VHv2/VLv2 or H2L2).

The invention provides variants of humanized 18G1 antibodies in which the humanized mature heavy chain variable region shows at least 90%, 95%, 96%, 97%, 98%, or 99% identity to Hu18G1VHv1 or 18G1VHv2 (SEQ ID NO: 34-35) and the humanized mature light chain variable region shows at least 90%, 95%, 96%, 97%, 98%, or 99% identity to Hu18G1VLv1 or Hu18G1VLv2 (SEQ ID NO: 38-39). In some such antibodies at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or all 31 of the backmutations or other mutations found in SEQ ID NO:34-35 and SEQ ID NO:38-39 are retained.

In some humanized 18G1 antibodies, at least one of the following positions in the VL region is occupied by the amino acid as specified: position L3 is occupied by V, position L10 is occupied by S, position L13 is occupied by V, position L15 is occupied by P, position L19 is occupied by A, position L20 is occupied by S, position L22 is occupied by S, position L42 is occupied by Q, position L70 is occupied by D, position L77 is occupied by R, position L78 is occupied by V, position L80 is occupied by A, and position L85 is occupied by V.

In some humanized 18G1 antibodies, at least one of the following positions is occupied by the amino acid as specified: position L3 is occupied by V, position L10 is occupied by S, position L13 is occupied by V, position L15 is occupied by P, position L19 is occupied by A, position L20 is occupied by S, position L22 is occupied by S, position L24 is occupied by K, position L28 is occupied by N, position L29 is occupied by V, position L42 is occupied by Q, position L46 is occupied by L, position L70 is occupied by D, position L77 is occupied by R, position L78 is occupied by V, position L80 is occupied by A, and position L85 is occupied by V.

In some humanized 18G1 antibodies, positions L3, L10, L13, L15, L19, L20, L22, L42, L70, L77, L78, L80, and L85 in the VL region are occupied by V, S, V, P, A, S, S, Q, D, R, V, A, and V, respectively. In some humanized 18G1 antibodies, at least one of the following positions is occupied by the amino acid as specified: H1 is occupied by E or Q, position H5 is occupied by V or Q, position H13 is occupied Q or K, position H19 is occupied R or K, position H40 is occupied by A or T, position H42 is occupied by G or D, position H44 is occupied G or R, position H49 is occupied by S or A, position H77 is occupied by S or T, position H82a is occupied by N or S, position H83 is occupied by R or K, position H84 is occupied by A or S, position H89 is occupied by V or M, position H108 is occupied by T or M, position L45 is occupied by Q, position L60 is occupied by D, and position L83 is occupied by L.

In some humanized 18G1 antibodies, at least one of the following positions is occupied by the amino acid as specified: H1 is occupied by E or Q, position H5 is occupied by V or Q, position H13 is occupied Q or K, position H19 is occupied R or K, position H40 is occupied by A or T, position H42 is occupied by G or D, position H44 is occupied G or R, position H49 is occupied by S or A, position H50 is occupied by G, position H63 is occupied by T, position H77 is occupied by S or T, position H82a is occupied by N or S, position H83 is occupied by R, position H84 is occupied by A, position H89 is occupied by V or M, H93 is occupied by V or A, position H108 is occupied by T or M.

In some humanized 18G1 antibodies, at least one of positions L45, L60, and L83 in the VL region is occupied by Q, D, and L, respectively.

In some humanized 18G1 antibodies, positions H1, H5, H13, H19, H40, H42, H44, H49, H77, H82a, H83, H84, H89, H93, and H108 in the VH region are occupied by, E, V, Q, R, A, G, G, S, S, N, R, A, V, V, and T, respectively, as in Hu18G1VHv2. In some humanized 18G1 antibodies, positions L3, L10, L13, L15, L19, L20, L22, L42, L45, L70, L77, L78, L80, and L85 in the VL region are occupied by, V, S, V, P, A, S, S, Q, Q, D, R, V, A, and V respectively, as in Hu18G1VLv1. In some humanized 18G1 antibodies, positions L3, L10, L13, L15, L19, L20, L22, L42, L60, L70, L77, L78, L80, L83, and L85 in the VL region are occupied by, V, S, V, P, A, S, S, Q, D, D, R, V, A, L, and V, respectively, as in Hu18G1VLv2.

The CDR regions of such humanized antibodies can be identical or substantially identical to the CDR regions of 18G1 mouse donor antibody. The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu18G1 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 6B3 or 18G1 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 6B3 or 18G1 variants (whether or not conservative) have no substantial effect on the binding affinity or potency of the humanized mAb, that is, its ability to bind to medin (e.g., the potency in some or all of the assays described in the present examples of the variant humanized 6B3 or 18G1 antibody is essentially the same, i.e., within experimental error, as that of murine 6B3 or 18G1 antibody.

D. Chimeric and Veneered Antibodies

The invention further provides chimeric and veneered forms of non-human antibodies, particularly the medin antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 6B3 and 18G1 antibodies are included in the invention.

E. Human Antibodies

Human antibodies against medin are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of medin, such as a C-terminal fragment of medin.

Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; U.S. Pat. No. 5,814,318; 5,789,650; 5,770,429; 5,661,016; 5,633,425; 5,625,126; 5,569,825; 5,545,806; Neuberger, *Nat. Biotechnol.* 14:826 (1996); and Kucherlapati, WO 91/10741 (1991)) and phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332); and methods described in WO 2008/081008 (e.g., immortalizing memory B cells isolated from humans, e.g., with EBV, screening for desired properties, and cloning and expressing recombinant forms).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, Md., 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra). One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 Glm3with or without the C-terminal lysine. Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mc1 for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. Saccharomyces is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof.

See Winnacker, From Genes to Clones, (VCH Publishers, NY, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, Protein Purification (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

H. Antibody Screening Assays

Antibodies can be subject to several screens including binding assays, functional screens, screens in animal models of diseases associated with medin, and clinical trials. Binding assays test for specific binding and, optionally, affinity and epitope specificity to medin (or a fragment thereof, such as amino acid residues 44-50 of SEQ ID NO: 1). Such screens are sometimes performed in competition with an exemplary antibody, such as 6B3 or 18G1. Optionally, either the antibody or medin target is immobilized in such assay.

Animal model screens test the ability of the antibody to therapeutically or prophylactically treat signs or symptoms in an animal model simulating a human disease associated with medin, such as a murine model of thoracic aortic aneurysms, such as that created by abluminal application of $CaCl_2$ to 129/SvE mice (Ikonomidis et al., J Surg Res. 115:157-163 (2003)) or a porcine model of thoracic aortic aneurysm, such as that created through intra-adventitial injections of collagenase and periadventitial application of crystalline $CaCl_2$ (Eckhouse et al., Circulation 128:S186-193 (2013)). Aortic structural changes such as elastic lamellar degradation and decreased collagen content can be assessed by magnetic resonance imaging (MRI), as well as biochemical and histological measurements. To facilitate testing in animal models, chimeric antibodies having a constant region appropriate for the animal model can be used (e.g., mouse-rat chimeras could be used for testing antibodies in rats). It can be concluded that a humanized version of an antibody will be effective if the corresponding mouse antibody or chimeric antibody is effective in an appropriate animal model and the humanized antibody has similar binding affinity (e.g., within experimental error, such as by a factor of 1.5, 2, or 3).

Clinical trials test for safety and efficacy in a human having a disease associated with medin.

I. Nucleic Acids

The invention further provides nucleic acids encoding any of the heavy and light chains described above (e.g., SEQ ID NOs: 3, 36, 11 and 29). Optionally, such nucleic acids further encode a signal peptide and can be expressed with the signal peptide linked to the constant region. Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens, such as medin, are useful in aortic aneurysms, Marfan syndrome, pancreatitis, Alzheimer's disease and obesity. For example, such antibodies can be conjugated with other therapeutic moieties, other proteins, other antibodies, and/or detectable labels. See WO 03/057838; U.S. Pat. No. 8,455, 622. Such therapeutic moieties can be any agent that can be used to treat, combat, ameliorate, prevent, or improve an unwanted condition or disease in a patient, such as aortic aneurysms, Marfan syndrome, pancreatitis, Alzheimer's disease and obesity. Therapeutic moieties can include cytotoxic agents, cytostatic agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. An immunomodulator can be any agent that stimulates or inhibits the development or maintenance of an immunologic response. A radiotherapeutic agent can be any molecule or compound that emits radiation. If such therapeutic moieties are coupled to a tumor-specific antibody, such as the antibodies described herein, the coupled therapeutic moieties will have a specific affinity for tumor cells or cancer cells over normal cells. Consequently, administration of the conjugated antibodies directly targets cancer cells with minimal damage to surrounding normal, healthy tissue. This can be particularly useful for therapeutic moieties that are too toxic to be administered on their own. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio) propionate for ricin. See Pietersz et al., *Cancer Res.* 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., *Leukemia* 18:1215-1222 (2004).

Some such antibodies can be linked to radioisotopes. Examples of radioisotopes include, for example, yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer. Chemother. Pharmacol.*, 48 Suppl 1:S91-S95 (2001).

Some such antibodies can be linked to other therapeutic moieties. Such therapeutic moieties can be, for example, cytotoxic or cytostatic. For example, antibodies can be conjugated with toxic chemotherapeutic drugs such as maytansine, geldanamycin, tubulin inhibitors such as tubulin binding agents (e.g., auristatins), or minor groove binding agents such as calicheamicin.

Antibodies can also be coupled with other proteins or peptides. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within medin or can bind to a different target antigen.

Antibodies can also be coupled with a detectable label. Such antibodies can be used, for example, for diagnosing the reduction of elasticity or increase in thickening of the vessel wall, for monitoring propensity for an aortic aneurysm, and/or for assessing efficacy of treatment. Such antibodies are particularly useful for performing such determinations in subjects having or being susceptible to aortic aneurysms, or in appropriate biological samples obtained from such subjects. Representative detectable labels that may be coupled or linked to a medin antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I), carbon ($^{14}$C, $^{11}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{64}$Cu, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as $^{111}$In and $^{90}$Y, ibritumomab tiuxetan can be used and will react with such isotopes to form $^{111}$In-ibritumomab tiuxetan and $^{90}$Y-ibritumomab tiuxetan, respectively. See Witzig, Cancer Chemother. Pharmacol. 48 Suppl 1:S91-S95 (2001).

Therapeutic moieties, other proteins, other antibodies, and/or detectable labels may be coupled or conjugated, directly or indirectly through an intermediate (e.g., a linker), to a murine, chimeric, veneered, or humanized medin antibody using techniques known in the art. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.,* 62:119-58

(1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

V. Therapeutic Applications

The above antibodies can be used for treating or effecting prophylaxis of a disease in a patient having or at risk for the disease mediated at least in part by medin. In some such diseases, for example, in subjects with Marfan's syndrome or subjects at risk for an aortic aneurysm, the antibody may reduce the degradation of elasticity and/or reduce the deposition of aortic medial amyloid.

Although an understanding of mechanism is not required for practice, it is believed that any or all of the following mechanisms may contribute to treatment of medin-related diseases: sequestration of free medin, inhibiting or reducing aggregation of medin, inhibiting or reducing medin fibril formation, reducing aortic medial amyloid deposits, clearing aggregated medial amyloid deposits, stabilizing a non-toxic conformation of medin, and/or preserving elasticity of the vessels. Antibody-drug conjugates can have additional mechanisms of action including the cytotoxic or cytostatic effect of the linked agent, typically after uptake within a cancer cell. Antibody-drug conjugates may also induce tumor-associated macrophage toxicity.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-20 mg/kg body weight, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

VI. Pharmaceutical Compositions and Methods of Use

Provided herein are several methods of diagnosing, monitoring, treating or effecting prophylaxis of diseases or conditions associated with medin (e.g., aortic aneurysm, diseases that weaken the layers of the aortic wall and increase the risk of thoracic aortic aneurysms, including Marfan syndrome, Loeys-Dietz and other familial connective tissue disorders, other non-specific connective tissue disorders (characterized by a family history of aneurysms), presence of a bicuspid aortic valve, infections, inflammatory disease, and other diseases such as pancreatitis, Alzheimer's disease, lupus, obesity). Additional cardiac diseases and vascular diseases include, atheroma, atherosclerosis, hypertension, coronary artery disease, myocardial infarction, vein thrombosis, varicose veins and vasculitis. Also provided are methods of diagnosing, monitoring, treating or effecting prophylaxis of diseases associated with granulomas, for example, infectious or non-infectious granulomatous diseases such as tuberculosis, leprosy, schistosomiasis, histoplasmosis, cryptococcosis, coccidioidomycosis, blastomycosis, Listeria monocytogenes, pneumocystis pneumonia, cat scratch disease, sarcoidosis, Crohn's disease, berylliosis, granulomatosis with polyangiitis, Churg-Strauss syndrome, rheumatic fever, rheumatoid arthritis, aspiration pneumona, granuloma annulare, vasculitis, pulmonary rheumatoid nodules and aspiration of food and other particulate material into the lung. Antibodies described above can be incorporated into a pharmaceutical composition for use in such methods. In general, an antibody or pharmaceutical composition containing an antibody is administered to a subject in need thereof. Patients amenable to treatment include individuals at risk of a disease associated with medin but not showing symptoms, as well as patients presently showing symptoms. Therefore, the pharmaceutical compositions can be administered prophylactically to individuals who have a known genetic risk of aortic aneurysm, e.g. subjects with Marfan syndrome. Such individuals include those having relatives who have experienced such a disease, and those whose risk is determined by analysis of genetic or biochemical markers. The identification of the subject can occur in a clinical setting, or elsewhere, such as in the subject's home, for example, through the subject's own use of a self-testing kit. As warranted by family history, genetic testing or medical screening, treatment can begin at any age (e.g., 10, 20, 30, 40, 50, 60, or 70 years of age). Usually, however, it is not necessary to begin treatment until a patient reaches 40, 50, 60 or 70. Treatment typically entails multiple dosages over a period of time and can be monitored by assaying antibody or activated T-cell or B-cell responses to a therapeutic agent (e.g., a truncated form of medin) over time. If the response falls, a booster dosage is indicated.

Although thoracic aortic aneurysms often go unnoticed because patients rarely feel any symptoms, possible warning signs include pain in the jaw, neck and upper back, chest or back pain, coughing, hoarseness or difficulty breathing. For some diseases, the subject can be identified using imaging techniques, such as MRI or imaging using antibodies that specifically bind medin may be available in the future.

In prophylactic applications, an antibody or a pharmaceutical composition of the same is administered to a subject susceptible to, or otherwise at risk of a disease in a regime (dose, frequency and route of administration) effective to reduce the risk, lessen the severity, or delay the onset of at least one sign or symptom of the disease. In therapeutic applications, an antibody or immunogen to induce an antibody is administered to a subject suspected of, or already suffering from a disease in a regime (dose, frequency and route of administration) effective to ameliorate or at least inhibit further deterioration of at least one sign or symptom of the disease.

A regime is considered therapeutically or prophylactically effective if an individual treated subject achieves an outcome more favorable than the mean outcome in a control population of comparable subjects not treated by methods disclosed herein, or if a more favorable outcome is demonstrated for a regime in treated subjects versus control subjects in a controlled clinical trial (e.g., a phase II, phase II/III, or phase III trial) or an animal model at the p<0.05 or 0.01 or even 0.001 level.

Effective doses vary depending on many different factors, such as means of administration, target site, physiological state of the subject, whether the subject is human or an animal, other medications administered, and whether treatment is prophylactic or therapeutic.

An exemplary dose range for antibodies can be from about 0.1-20 mg/kg body weight, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Antibody can be administered in such doses daily, on alternative days, weekly, fortnightly, monthly, quarterly, or according to any other schedule determined by empirical analysis. An exemplary treatment entails administration in multiple doses over a prolonged period, for example, of at least six months. Additional exemplary treatment regimes entail administration once per every two weeks or once a month or once every 3 to 6 months.

Antibodies can be administered via a peripheral route. Routes of administration include topical, intravenous, oral, subcutaneous, intraarterial, intracranial, intrathecal, intraperitoneal, intranasal or intramuscular. Routes for administration of antibodies can be intravenous or subcutaneous. Intravenous administration can be, for example, by infusion over a period such as 30-90 min. This type of injection is most typically performed in the arm or leg muscles. In some methods, agents are injected directly into a particular tissue where deposits have accumulated, for example intracranial injection.

Pharmaceutical compositions for parenteral administration can be sterile and substantially isotonic (250-350 mOsm/kg water) and manufactured under GMP conditions. Pharmaceutical compositions can be provided in unit dose form (i.e., the dose for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with another agent effective in treatment or prophylaxis of the disease being treated.

After treatment, the subject's condition can be evaluated to determine the progress or efficacy of such treatment.

A. Diagnostics and Monitoring Methods

Also provided are methods of detecting an immune response against medin in a patient suffering from or susceptible to diseases associated with medin. The methods can be used to monitor a course of therapeutic and prophylactic treatment with the agents provided herein. For example, the methods can be used to monitor active immunization (e.g., antibody produced in response to administration of immunogen) and passive immunization (e.g., measuring level of administered antibody).

Also provided are methods of detecting medin deposition or aggregation in a subject, for example, by measuring medin in a sample from a subject or by in vivo imaging of medin in a subject. Such methods are useful to diagnose or confirm diagnosis of diseases associated with medin, or susceptibility thereto. The methods can also be used on asymptomatic subjects. The presence of medin indicates susceptibility to future symptomatic disease. The methods are also useful for monitoring disease progression and/or response to treatment in subjects who have been previously diagnosed with a disease associated with medin, such as, for example, Marfan syndrome or aortic aneurysm.

The in vivo imaging methods can work by administering a reagent, such as antibody that binds to medin in the subject, and then detecting the reagent after it has bound. Antibodies typically bind to an epitope of medin. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the subject, or via other routes deemed reasonable. The dose of reagent should be within the same ranges as for treatment methods. Typically, the reagent is labeled, although in some methods, the primary reagent with affinity for medin is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. A decrease in values relative to base line generally signals a positive response to treatment.

B. Passive Immunization

The antibody profile following passive immunization typically shows an immediate peak in antibody concentration followed by an exponential decay. Without a further dose, the decay approaches pretreatment levels within a period of days to months depending on the half-life of the antibody administered. For example the half-life of some human antibodies is of the order of 20 days.

In some methods, a baseline measurement of antibody to medin in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

IX. Kits

The invention further provides kits (e.g., containers) comprising the medin antibodies or other antagonists disclosed herein and related materials, such as instructions for use (e.g., package insert). The instructions for use may contain, for example, instructions for administration of the medin antibody and optionally one or more additional agents. The containers of medin antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

X. Other Applications

The antibodies can be used for detecting medin, or fragments thereof, in the context of clinical diagnosis or treatment or in research. For example, the antibodies can be used to detect the presence of medin in a biological sample or biopsy as an indication that the biological sample comprises medin. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of medin) to the biological sample(s) is increased, decreased, or the same relative to antibody binding to the control sample(s). Increased binding of the antibody to the biological sample(s) relative to the control sample(s) indicates the presence of medin in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the medin in a biological sample or biopsy to monitor and evaluate the efficacy of a therapeutic agent being used to treat a patient diagnosed with a disease associated with medin. A biological sample from a patient diagnosed with a disease associated with medin is evaluated to establish a baseline for the binding of the antibodies to the sample (i.e., a baseline for the presence of the medin in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of the medin) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of medin) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of medin), it can be concluded that the therapeutic agent was effective in treating the medin toxicity, aggregation or deposition in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of diseases associated with medin.

The antibodies can also be used as research reagents for laboratory research in detecting medin, fragments thereof, or misfolded lactadherin. In such uses, antibodies can be labeled with fluorescent molecules, spin-labeled molecules, enzymes, or radioisotopes, and can be provided in the form of kit with all the necessary reagents to perform the detection assay for medin, or fragments thereof. The antibodies can also be used to purify medin, or binding partners of medin, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of Medin Monoclonal Antibodies

Mice were immunized with a c-terminal peptide or full-length human medin, hybridomas cloned and antibodies screened for activity using ELISA, Western blot, Biacore and immunocytochemistry.

Initial ELISA studies revealed that antibodies raised against full-length 50 aa medin (e.g. 6B3) bind both medin peptide and lactadherin polypeptide, while antibodies raised against a c-terminal peptide (e.g. 18G1) appeared to be medin specific.

Subsequent studies confirmed these observations and revealed that 18G1 recognized the c-terminal end of medin, a neo-epitope created when medin is cleaved from lactadherin.

Data from Western blot also showed that both 6B3 and 18G1 were capable of binding both monomeric and oligomeric forms of medin.

To assess the specificity for endogenous human medin, a series of immunohistochemical studies were conducted with thoracic aorta samples from aneurysm or Marfan syndrome patients. The results demonstrated that anti-medin antibodies were able to bind endogenous medin, although the intensity and pattern of staining appeared to be antibody specific. While 6B3 stained dense aggregated (Thioflavin S+) material or amyloid deposits with high affinity in and around the patient aneurysm, 18G1 showed little to no specific staining. In contrast, 18G1 widely stained structures in the tunica media, the region of the aorta that contains the elastin fibers and smooth muscle cells.

These data demonstrated that anti-medin antibodies can detect endogenous medin peptide present in aneurysm and Marfan patient samples and showed that the antibody epitope can play an important role in determining the size (monomer, dimer, trimer, etc.) and aggregation state (oligomer, protofibril, aggregate) of medin detected.

Specifically, monoclonal antibodies against medin were generated as described in Materials and Methods.

Characterization of Anti-Medin Antibody Clones

The immunization of mice with full-length human medin (50 aa, FIGS. 1A and B) or the c-terminal human peptide (7 aa, FIG. 1B) generated a panel of anti-medin monoclonal antibodies of interest. The IgGs emanating from the cloning of these antibodies were first assessed in a two-pronged ELISA, an assay that determined binding to human lactadherin polypeptide and human medin peptide (50 aa). The results of this initial screen revealed that almost all antibodies raised against the full-length medin peptide were able to bind both medin and lactadherin, while antibodies raised against the c-terminal peptide were largely medin specific (data not shown). Since the lactadherin used in the ELISA was a synthetic polypeptide and likely not properly folded, additional FACS studies were conducted with MDA-MB-231 cells, a human breast cancer cell line that expresses native lactadherin. Interestingly, the results of these studies showed that the antibodies raised against the full-length peptide were not able to bind medin when the lactadherin was expressed on cells and properly folded (data not shown). These data suggested that the medin peptide was likely hidden inside the lactadherin molecule and only exposed when the lactadherin was misfolded or denatured.

Based on results from this initial screen, a subpopulation of full-length and c-terminal medin antibodies were further screened with a four-pronged ELISA. This assay looked at the binding to human lactadherin, full-length human medin (50 aa), the human c-terminal peptide and the mouse c-terminal peptide. As shown in FIG. 2, a full titration curve was generated for each antibody of interest. A comparison of these curves highlighted some of the differences noted among antibodies. Antibodies like 6B3, raised against full-length human medin bound to full-length medin and lactadherin polypeptide, but not the c-terminal peptides (FIG. 2A). This data indicated that the epitope for these antibodies was not in the c-terminal domain. In contrast, c-terminal antibodies such as 18G1 were able to bind full length medin and the c-terminal peptides, but had little to no affinity for lactadherin (FIG. 2B). These observations were the first to indicate that antibodies like 18G1 might recognize the c-terminal end of medin, a neo-epitope created when medin is cleaved from the lactadherin polypeptide.

Characterization of Anti-Medin Antibodies with Western Blotting

Figures 3A, 3B:
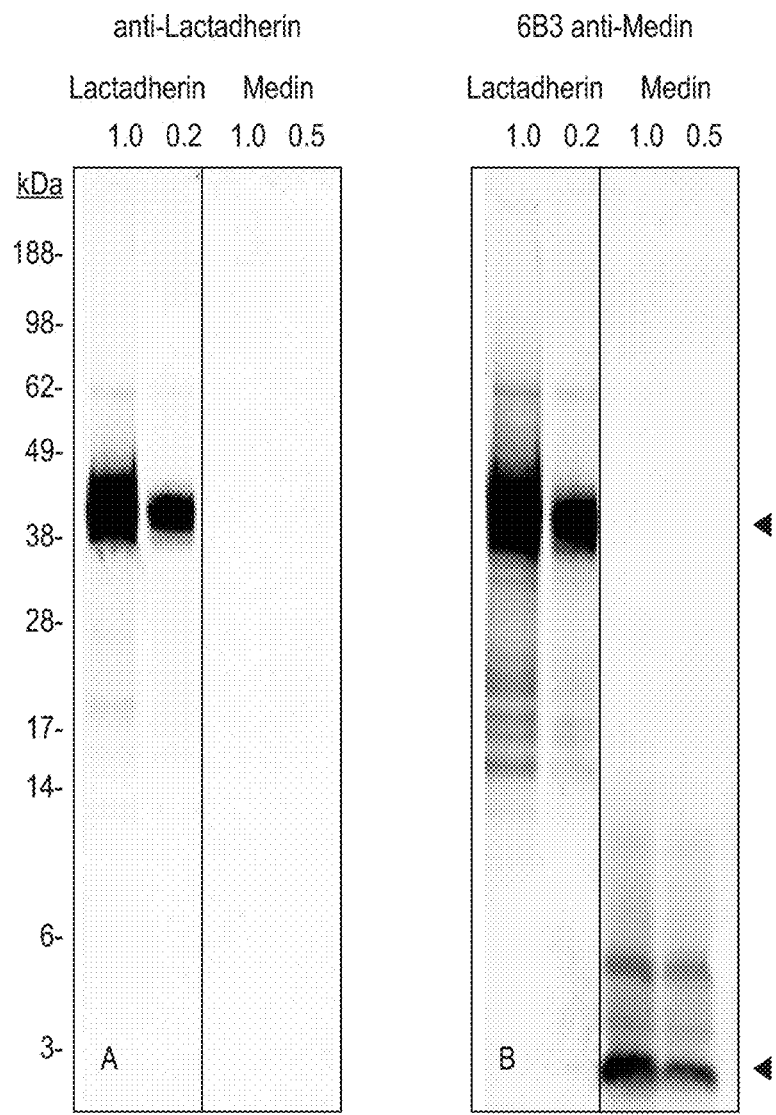
FIG. 3A & FIG. 3B.
Figures 4A, 4B:
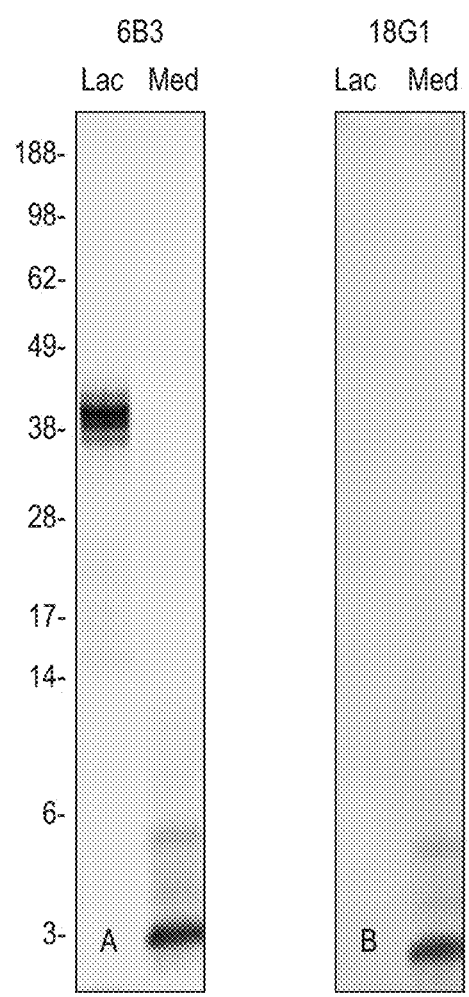
FIG. 4A & FIG. 4B.

The results from ELISA studies showed that some anti-medin monoclonal antibodies could differentially bind to full-length lactadherin and the excised medin peptide. To better understand the selectivity of anti-medin antibodies and see if mutimeric or oligomer forms of medin were also recognized, Western blot analysis was used. As shown in FIG. 3A, the use of a commercial anti-lactadherin antibody revealed a predominant lactadherin band at ~46 kDa, but did not recognize the 50 aa medin peptide. When, however, the anti-medin antibody 6B3 was used, a pronounced lactadherin band was seen, a band similar to that detected with the anti-lactadherin antibody (FIGS. 3A and 3B). In contrast, 6B3 also recognized several bands in the medin sample (FIG. 3B), including a 3-4.5 kDa band that corresponded to the predicted monomer form of medin. In addition, several weaker medin bands with a higher molecular weight were also observed. Since medin is prone to aggregate, these bands likely represent multimers or oligomers of medin. A comparison of a full-length and c-terminal medin antibody (6B3 with 18G1, FIG. 4), further highlighted the differences between these antibodies. Whereas 6B3 recognized medin embedded within the lactadherin peptide as well as the 50aa medin peptide (FIG. 4A), 18G1 only recognized the cleaved medin peptide (FIG. 4B). It is noteworthy that 18G1 looked identical to 6B3 in its ability to recognize both medin monomer and multimers of medin.

Table 4 depicts Biacore analysis of the binding affinity of 6B3 and 18G1 to full length medin. 6B3 and 18G1 had 1 nM and 12 nM affinities for medin, respectively. The affinity for lactadherin has yet to be determined.

TABLE 4

|  | Ka (1/Ms) | Kd (1/s) | KD (M) | Rmax |
| --- | --- | --- | --- | --- |
| 6B3 | 1.11E+06 | 9.51E−04 | 1.04E−9 | 46.16 |
| 18G1 | 5.90E+05 | 0.007117 | 12.06E−9 | 59.09 |

Example 2. Experiments Specific to the Antibody and Disease State

Immunohistochemistry Characterization of Anti-Medin Antibodies with Human Tissue The ELISA and Western blot data clearly showed that anti-medin antibodies can bind full-length human medin, the predicted form found in vivo and thought to be deposited in aortic amyloid plaques (Haggqvist et al.). To further assess the specificity of 6B3 and 18G1 for endogenous human medin, a series of immunohistochemical studies were conducted with thoracic aorta samples from patients with aneurysms. The results of these studies demonstrated that all anti-medin antibodies assessed when able to bind endogenous medin, although the intensity and pattern of staining appeared to be antibody specific. When antibody 6B3 was used to stain tissues, immunoreactivity was localized to regions in and around the patient aneurysm. In particular, 6B3 stained dense aggregated material or amyloid deposits with high affinity. The finding that these deposits also stained with Thioflavin S, a marker of misfolded amyloid proteins, suggested that 6B3 stained the medin aggregates previously described (Haggqvist et al.; Peng et al.). Interestingly, 6B3 also stained loose fibrillar, Thioflavin S negative structures that were seen in close proximity to the dense aggregates. While the exact nature of these deposits is unknown, it is possible that these may be medin oligomers or multimers that are assembling into larger, Thioflavin S positive structures.

The pattern of staining seen with antibody 18G1 was distinctly different from 6B3. The most notable difference was the lack of 18G1 staining of the Thioflavin S positive dense aggregates seen in and around the aneurysms. This lack of staining was quite striking since the loose fibrillar deposits associated with the aggregates were still immunoreactive. Pronounced diffuse 18G1 staining was also detected in the tunica media, the region of the aorta that contains the elastin fibers and smooth muscle cells. Since previous in vitro studies suggest that medin binds to and disrupts the link between elastin and smooth muscle cells (Peng et al.), the observed 18G1 staining in the tunica media was not surprising.

Based on these observations, additional studies were conducted with samples from Marfan syndrome patients, a genetic disease that affects the elastin fibers in the aorta and can eventually led to an aneurysm. Initial studies showed that both 6B3 and 18G1 stained structures in the aorta from Marfan patients, although clear differences in the degree of staining and distribution of signal were noted. As seen in aneurysm patient tissue samples, 6B3 largely stained the dense aggregated amyloid deposits and loose fibrillar deposits seen in the aorta of Marfan patients. However, since these structures appeared to be less prevalent in the samples evaluated, the staining also appeared to be attenuated. In contrast, the immunoreactivity seen with 18G1 in the Marfan patient tissues was both widely distributed and intense in signal. Specific 18G1 staining was present throughout the tunica media and clearly associated with the elastin fibers and smooth muscle cells. In addition, moderate staining was also detected in the tunica intima, tunica adventitia and associated with fat cells. Together these data demonstrated that anti-medin antibodies can detect endogenous medin peptide present in aneurysm and Marfan patient samples and showed that the epitope of the antibody can play an important role in determining the size (monomer, dimer, trimer, etc.) and aggregation state (oligomer, profibril, aggregate) of medin.

Example 3. Sequence Analysis of Antibodies

Based on data generated from the medin and lactadherin binding assays, tissue staining and other in vitro assays (data not shown), several antibodies were selected for further analysis. As a first step, the complete amino acid sequence for the variable regions of 18G1 and 6B3 were determined (FIGS. 5 and 6). The results of this work highlighted the differences among these antibodies despite their affinity of medin.

Example 4. Materials and Methods

Generation of Anti-Medin Monoclonal Antibodies

Mice were immunized weekly for 4 to 10 weeks with 10, 25, or 50 µg of full length human medin (see FIGS. 1A and B) (SEQ ID NO: 1) or human C-terminal peptide (FIG. 1B) (SEQ ID NO: 2) conjugated to KLH with RIBI adjuvant (Sigma Adjuvant System, Sigma-Aldrich). Three to four days prior to fusion, selected mice with the highest titers for full length human medin were given a final IV boost of immunogen in saline solution. Fusions were performed using a modified procedure described by Kohler and Milstein (Kohler and Milstein, 1975) and electrofusion. Fused cells in selection media were plated in 96-well plates and screened 7-10 days later using an ELISA screen.

ELISA

Hybridoma selection was performed using a Direct ELISA method as the primary screen. Briefly, 96-well plates (Costar RIA/EIA plates) were coated with full length human medin (FIG. 1B) and incubated at room temperature for 1 hour. The plates were then blocked with 1% BSA (bovine serum albumin)/PBS (phosphate buffered saline) at room temperature. After about 15 minutes, plates were emptied and supernatants from the fusion or cloning plates were then added and incubated for 1 hour at room temperature. After incubation and washing in wash buffer (PBS+0.05% Tween 20), antibody binding was detected with a goat anti-mouse antibody conjugated to horseradish peroxidase (Jackson Immuno Research) diluted 1:2,000 and incubated for 1 hour at room temperature. The horseradish peroxidase label was then visualized with ABTS (Thermo Scientific) as a substrate and read at 405 nm on a microplate reader. Wells with ~1.0 OD units were considered positive.

To further characterize antibodies of interest, ELISA titration curves were generated to determine antibody binding to human lactadherin (FIG. 1A, Sino Biological In.), full-length human medin peptide (50 aa, FIGS. 1A and B) or to the human or mouse C-terminal peptides (see FIG. 1B). Plates were coated with full length human medin, human C-terminal peptide-OVA, mouse C-terminal peptide-OVA and lactadherin at 2.5 ug/mL, 50 uL/well and incubated for about 1 hour at room temperature. The plates were then blocked with 1% BSA/PBS at room temperature. After about 15 minutes, plates were emptied and antibodies of interest were then added to the plates and after a 1 hour incubation at room temperature, the plates were washed with wash buffer. The detection antibody, goat anti-mouse antibody conjugated to horseradish peroxidase (Jackson ImmunoResearch) diluted 1:2,000 in 0.5% BSA/PBS/TBS-T was added to plates and incubated for 1 hour at room temperature. Finally, the plates were washed and then incubated with ABTS substrate (Thermo Scientific) for 15 minutes at room temperature to visualize signal and read at 405 nm on a microplate reader.

Western Blot

Western blot analysis was used to further assess the binding of a panel of anti-medin monoclonal antibodies to full-length medin peptide (FIGS. 1A and B) or lactadherin (FIG. 1A). Briefly, 0.2-1 ug lactadherin (Sino Biologicals, Inc.; Cat #10853-H08B) or medin peptide (American Peptide, Cat #: 366587) was diluted in 1×LDS sample buffer (Life Technologies), loaded onto 10% NuPAGE bis-tris gels and subjected to electrophoresis in 2-(N-morpholino)ethanesulfonic acid buffer at a constant 90V for 105 minutes. After electrophoresis, the SDS-PAGE gels were blotted onto nitrocellulose filter paper (iBlot, P7 Program) and blocked with blocking buffer (Licor) for 30 minutes. The filters were then incubated in 0.5 ug/ml rabbit anti-lactadherin (Santa Cruz Biotech, Cat #sc-33546) or mouse anti-medin antibodies (including 6B3 and 18G1) in blocking buffer for 1 hour at room temperature (or overnight at 4° C.), followed by three, 10 minute washes with 1×TBS. The filters were placed in the appropriate IRDye 800CW-conjugated secondary antibody (goat anti-mouse or goat anti-rabbit, Odyssey) diluted 1:20,000 in block buffer. After incubating the filters in secondary antibody solution for 1 hour at room temperature, the filters were washed and imaged on an Odyssey CLx infrared imager (Licor).

Immunohistochemistry

Human aorta samples from patients with a thoracic aorta aneurysm or Marfan syndrome were procured, fixed in formalin, embedded in paraffin wax and 5-6 um sections cut and collected on microscope slides. At the time of staining, section-mounted slides were baked at 60° C. for 20 minutes, treated with xylene (2×10 minutes) and rehydrated with a graded series of ethanol rinses. Tissue sections were then rinsed for 5 minutes in 0.01 M phosphate buffered saline (PBS, pH 7.4; Sigma) and incubated for 60 minutes at 37° C. in a glucose oxidase blocking solution (Andrew et al., J. Histochem 19:426). Subsequently, slides were rinsed in PBS (3×5 minutes) and incubated for 24-72 hours at 4° C. with an anti-medin antiserum such as 6B3 or 18G1 (diluted to 0.25-1 µg/ml in 1% BSA/0.3% triton X100/PBS). To visualize staining, the sections were washed (3×10 minutes) in PBS and then incubated with an anti-mouse labeled polymer DAB staining system (30 minutes at room temperature; Dako EnVision). The sections were washed in PBS (3×10 minutes) and 0.05M Tris (pH 7.6, 1×10 minutes) before the 10-minute DAB reaction (100 mg 3,3'-diaminobenzidine, 250 ml Tris, 30 µl 30% $H_2O_2$). The sections were then transferred to Tris (2×5 minutes), rinsed in $H_2O$ (1 minute) and stained with Myer's hematoxylin (Dako). Sectioned were then covered slipped with Cytoseal 60 (Richard Allen Scientific). Additional sections were stained with Thioflavin S (5 minutes; 0.5 g/50 ml $H_2O$) after the hematoxylin step to visualize aggregated amyloid deposits in tissues. These slides were rinse in 70% ethanol (5 minutes) and $H_2O$ (2×30 seconds) and coverslipped with Prolong Gold (Life Technologies). Slides were visualized with bright-field and fluorescence microscopy and digital images acquired using the MetaMorph software.

BiaCore

Anti-mouse antibody (GE Heathcare) was immobilized on a sensor chip C5 (lacking dextran chains) via amine coupling following the instructions provided in the GE Healthcare anti-mouse kit. Anti-medin monoclonal antibodies of interest were then captured on the chip at a level that ensured a maximum binding of analyte at 30-50 RU. Various concentrations of analyte, full-length human medin (50 aa, FIGS. 1A and B) were passed over the captured ligand at 30 ul/min in running buffer (Hepes buffered saline+0.05% P-20, 1 mg/mL BSA) in either 2-fold or 3-fold dilutions, depending on the magnitude of the spanned concentration range. For each concentration, the reaction proceeded for a period of time needed for the higher analyte concentrations to reach equilibrium during association, as well as at least 10% of signal to decay during dissociation. At least one concentration (not the highest or lowest) was run in duplicate. The concentration ranges of analyte were selected based on preliminary experimentation to span at least 10-fold above $K_D$ to 10-fold below $K_D$. The data were doubled referenced to both an irrelevant sensor not containing the medin antibodies and a 0 nM concentration of medin to account for the dissociation of antibodies from the antimouse sensor. The data was then analyzed with a global 1:1 fit using the Biacore software.

Sequencing

In order to sequence the variable domains of each medin monoclonal antibody, the total mRNA was extracted from $1×10^7$ hybridoma cells using the Oligotex Direct mRNA Mini Kit (Qiagen Cat. No. 72022). Double strand cDNAs was then generated by using 80 µg of total mRNA as a template and the Marathon cDNA Amplification Kit (Clontech Cat. no. 634913). In order to amplify the variable region heavy chain (VH) and variable region light chain (VL) DNA for sequencing, PCR was performed by using the universal adaptor primer included in Marathon cDNA Amplification kit as the 5' primer for both the VH and VL amplification. Since the anti-medin monoclonal antibodies of interest have a kappa light chain, the CK 3' primer ACTAGTCGACATGAAGTTGCCTGTTAGGCTGTTGGTGCTG (SEQ ID NO: 19) was used for VL PCR amplification. For VH amplification, the following 3' primers were used respectively:

```
18G1 (heavy chain is gamma 2a):
                              (SEQ ID NO: 20)
GGATCCCGGGAGTGGATAGACCGATGG 6B3 (heavy chain is gamma 2b):
                              (SEQ ID NO: 21)
GGATCCCGGGAGTGGATAGACTGATGG
```

The PCR products were then gel purified and cloned into the Topo 4 vector using the Zero Blunt TOPO PCR cloning kit (Lifetech, Cat. No. K2800-20) and sent to Elimbio for sequencing.

Example 5. Design of Humanized_6B3 Antibodies

The starting point or donor antibody for humanization was the mouse antibody 6B3. The heavy chain variable amino acid sequence of mature m6B3 is provided as SEQ ID NO:11. The light chain variable amino acid sequence of mature m6B3 is provided as SEQ ID NO:29. The heavy chain Kabat/Chothia Composite CDR1, CDR2, and CDR3 amino acid sequences are provided as SEQ ID NOS:12-14, respectively. The light chain Kabat CDR1, CDR2, and CDR3 amino acid sequences are provided as SEQ ID NOS:16-18, respectively. Kabat numbering is used throughout.

The variable kappa (Vk) of 6B3 belongs to mouse Kabat subgroup 5 which corresponds to human Kabat subgroup 1 and variable heavy (Vh) to mouse Kabat subgroup 1b which corresponds to human Kabat subgroup 1 (Kabat, 1991, supra)

11 residue CDR-L1 belongs to canonical class 2; 7 residue CDR-L2 to class 1 and 9 residue CDR-L3 to class 1 in Vk

[Martin A C, and Thornton J M. 1996, J Mol Biol. 263:800-15.]. 12 residue CDR-H1 belongs to class 3; 16 residue CDR-H2 to class 1 [Martin & Thornton, supra). CDR-H3 has no canonical classes. (Shirai H, et al., (1999) FEBS Lett. 455:188-197)

The residues at the interface between the Vk and Vh domains are the ones commonly found; except that light chain V44 is typically Proline, therefore, this interface residue is specifically targeted for back-mutation.

A search was made over the protein sequences in the PDB database (Deshpande N, et al., 2005 Nucleic Acids Res. 33: D233-D237) to find structures, which would provide a rough structural model of 6B3. We used the crystal structure of antibody fab (pdb code 3CFD) (Debler E W, et al., Science. 2008; 319:1232-1235) for the Vk structure since it had reasonably good resolution (2.5 A) and overall sequence similarity to 6B3 Vk, retaining the same canonical structures for the loops. An antibody fab with pdb code 3MBX (Teplyakov A, et al., Mol Immunol. 2010; 47: 2422-2426) was used for the Vh structure. It had good overall sequence similarity and reasonably good resolution (1.6 A). In addition, CDRs-H1 and H2 had the same canonical structures as 6B3 Vh. We used Bioluminate software to model a rough structure of 6B3. This software is licensed from Schrodinger Inc.

A search of the non-redundant protein sequence database from NCBI allowed selection of suitable human frameworks into which to graft the murine CDRs. For Vk, a human kappa light chain with NCBI accession code BAC01558.1 (GI: 21669067) (Akahori, Y., et al., Direct Submission (25 Jun. 2001) Yoshikazu Kurosawa, Institute for Comprehensive Medical Science, Fujita Health University; Kutsukake-cho, Toyoake 470-1192, Japan) was chosen. This has the same canonical classes for CDR-L1 and L2. It is a member of Kabat human kappa subgroup 2. For Vh, human Ig heavy chain AAD53863.1 (GI: 5834194) (Wang, X. and Stollar, B. D., Clin. Immunol. 1999, 93, 132-142) was chosen, again with the same canonical classes. It is a member of Kabat human heavy subgroup 1.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www. who.int/medicines/services/inn/BioRev2014.pdf) Residues were changed to align with corresponding human germ line sequence, where possible, to enhance humanness.

6B3VH was aligned to human germ line sequence IGHV4-30-3*01 and 6B3VL was aligned against IGKV1-NL1*01.

Three humanized heavy chain variable region variants and two humanized light chain variable region variants were constructed containing different permutations of substitutions (Hu6B3VHv1, Hu6B3VHv2, and Hu6B3VHv3, (SEQ ID NOS:26-28, respectively) and Hu6B3VLv1 and Hu6B3VLv2 (SEQ ID NOS:31-32, respectively) (FIGS. 11A-D and FIGS. 12A-D). The exemplary humanized Vh and Vk designs, with backmutations and other mutations based on selected human frameworks, are shown in FIGS. 11A-D and FIGS. 12A-D, respectively. The gray-shaded areas in FIGS. 11A-D and FIGS. 12A-D indicate the CDRs as defined by Kabat/Chothia Composite. SEQ ID NOS:26-28 and 32 contain backmutations and other mutations as shown in Table 5. The amino acids at positions H1, H3, H5, H10, H15, H19, H44, H48, H49, H67, H78, H79, H81, H82, H82a, H82b, H82c, H83, H84, H85, H89, and H108 in Hu6B3VHv1, Hu6B3VHv2, and Hu6B3VHv3, and at positions L71, L87, L100, and L104 in Hu6B3VLv1 and Hu6B3VLv2, are listed in Table 6.

TABLE 5

$V_H$, $V_L$ Backmutations and Other Mutations for Humanized 6B3

| $V_H$ or $V_L$ Variant | $V_H$ or $V_L$ Exon Acceptor Sequence | Changes from Acceptor Framework Residues (based on Kabat/Chothia Composite CDRs) |
| --- | --- | --- |
| Hu6B3VHv1 (SEQ ID NO: 26) | NCBI accession code AAD53863.1 (SEQ ID NO: 25) | H3, H5, H10, H15, H19 |
| Hu6B3VHv2 (SEQ ID NO: 27) | NCBI accession code AAD53863.1 (SEQ ID NO: 25) | H1, H3, H5, H10, H15, H19, H44, H79, H81, H82, H82b, H82c, H83, H84, H85, H89 |
| Hu6B3VHv3 (SEQ ID NO: 28) | NCBI accession code AAD53863.1 (SEQ ID NO: 25) | H1, H3, H5, H10, H15, H19, H44, H48, H49, H67, H78, H79, H81, H82, H82a, H82b, H82c, H83, H84, H85, H89, H108 |
| Hu6B3VLv1 (SEQ ID NO: 31) | NCBI accession code BAC01558.1 (SEQ ID NO: 30) | (none) |
| Hu6B3VLv2 (SEQ ID NO: 32) | NCBI accession code BAC01558.1 (SEQ ID NO: 30) | L71, L87, L100, L104 |

TABLE 6

Kabat Numbering of Framework Residues (based on Kabat/Chothia Composite CDRs) for Backmutations and Other Mutations in Humanized 6B3 Antibodies

| Residue | AAD53863.1 (Heavy Chain) | BAC01558.1 (Light Chain) | Mouse 6B3 | Hu6B3VHv1 | Hu6B3VHv2 | Hu6B3VHv3 | Hu6B3VLv1 | Hu6B3VLv2 |
| --- | --- | --- | --- | --- | --- | --- | --- | --- |
| L71 |  | F | Y |  |  |  | F | Y |
| L87 |  | Y | F |  |  |  | Y | F |
| L100 |  | G | G |  |  |  | G | Q |

TABLE 6-continued

Kabat Numbering of Framework Residues (based on Kabat/Chothia Composite CDRs) for Backmutations and Other Mutations in Humanized 6B3 Antibodies

| Residue | AAD53863.1 (Heavy Chain) | BAC01558.1 (Light Chain) | Mouse 6B3 | Hu6B3VHv1 | Hu6B3VHv2 | Hu6B3VHv3 | Hu6B3VLv1 | Hu6B3VLv2 |
|---|---|---|---|---|---|---|---|---|
| L104 | | V | L | | | | V | L |
| H1 | Q | | Q | Q | E | E | | |
| H3 | T | | T | Q | Q | Q | | |
| H5 | K | | K | Q | Q | Q | | |
| H10 | A | | G | G | G | G | | |
| H15 | T | | S | S | S | S | | |
| H19 | T | | S | S | S | S | | |
| H44 | A | | G | A | G | G | | |
| H48 | L | | L | L | L | I | | |
| H49 | A | | A | A | A | G | | |
| H67 | L | | L | L | L | V | | |
| H78 | V | | V | V | V | F | | |
| H79 | V | | F | V | S | S | | |
| H81 | T | | K | T | K | K | | |
| H82 | M | | I | M | L | L | | |
| H82a | T | | A | T | T | S | | |
| H82b | N | | S | N | S | S | | |
| H82c | M | | V | M | V | V | | |
| H83 | D | | D | D | T | T | | |
| H84 | P | | T | P | A | A | | |
| H85 | V | | A | V | A | A | | |
| H89 | T | | T | T | V | V | | |
| H108 | L | | L | L | L | T | | |

An alignment of the murine 6B3 Vh sequence (SEQ ID NO:11) with the human acceptor sequence (AAD53863.1; SEQ ID NO:25, and the Hu6B3VHv1, Hu6B3VHv2, and Hu6B3VHv3, (SEQ ID NOs:26-28, respectively), is shown in FIG. 7. The CDR regions as defined by Kabat/Chothia Composite are boxed. Positions at which canonical, vernier, or interface residues differ between mouse and human acceptor sequences are candidates for substitution. Examples of canonical/CDR interacting residues include Kabat residue H48 in FIGS. 11A-D. Examples of interface/packing (VH+VL) residues include Kabat residues H35, H37, H39, H45, H47, H93, H95, H101, and H103 in FIGS. 11A-D.

An alignment of the murine 6B3 Vk sequence (SEQ ID NO:29) with the human acceptor sequence (BAC01558.1; SEQ ID NO:30), and the Hu6B3VLv1 and Hu6B3VLv2 (SEQ ID NOs 31 and 32, respectively), is shown in FIG. 8. The CDR regions as defined by Kabat are boxed. Positions at which canonical, vernier, or interface residues differ between mouse and human acceptor sequences are candidates for substitution. Examples of interface/packing (VH+VL) residues include Kabat residues L34, L36, L38, L44, L46, L87, L89, L91, L96, and L98 in FIGS. 12A-D.

The rationales for selection of the positions indicated in Tables 5 and 6 in the light chain variable region as candidates for substitution are as follows.

F71Y; Y87F; G100Q and V104L are frequency/germ-line aligning mutations.

The rationales for selection of the positions indicated in Tables 5 and 6 in the heavy chain variable region as candidates for substitution are as follows.

Q1E is a stability enhancing mutation to mitigate pyroglutamate formation potential. (Liu, 2011, supra)

T3Q; K5Q; A10G; T15S; T19S; A44G; L48I; A49G; L67V; V78F; V79S; T81K; M82L; T82aS; N82bS; M82cV; D83T; P84A; V85A; T89V, and L108T are frequency based back-mutations or germ-line aligning mutations.

The designs based on these human frameworks were:

VARIABLE KAPPA
>Hu6B3VLv1
(SEQ ID NO: 31)
DIQMTQSPSSLSASVGDRVTITCRASQDISNFLSWYQQKPGKAPKLLIYY

TSRLHSGVPSRFSGSGSGTDFTLTISSLQPEDFATYYCQQGKTLPPTFGG

GTKVEIK

>Hu6B3VLv2
(SEQ ID NO: 32)
DIQMTQSPSSLSASVGDRVTITCRASQDISNFLSWYQQKPGKAPKLLIYY

TSRLHSGVPSRFSGSGSGTDYTLTISSLQPEDFATYFCQQGKTLPPTFGQ

GTKLEIK

VARIABLE HEAVY
>Hu6B3VHv1
(SEQ ID NO: 26)
QVQLQESGPGLVKPSQTLSLTCTFSGFSLSTSDMGVGWIRQPPGKALEWL

AHIWWNDNKYYNIALKNRLTISKDTSKNQVVLTMTNMDPVDTATYYCARL

VGSWFAYWGQGTLVTVSS

>Hu6B3VHv2
(SEQ ID NO: 27)
EVQLQESGPGLVKPSQTLSLTCTFSGFSLSTSDMGVGWIRQPPGKGLEWL

AHIWWNDNKYYNIALKNRLTISKDTSKNQVSLKLTSVTAADTAVYYCARL

VGSWFAYWGQGTLVTVSS

>Hu6B3VHv3
(SEQ ID NO: 28)
EVQLQESGPGLVKPSQTLSLTCTFSGFSLSTSDMGVGWIRQPPGKGLEWI

GHIWWNDNKYYNIALKNRVTISKDTSKNQFSLKLSSVTAADTAVYYCARL

VGSWFAYWGQGTTVTVSS

Example 6. Design of Humanized 18G1 Antibodies

The starting point or donor antibody for humanization was the mouse antibody 18G1. The heavy chain variable amino acid sequence of mature m18G1 is provided as SEQ ID NO:3. The light chain variable amino acid sequence of mature m18G1 is provided as SEQ ID NO:36. The heavy chain Kabat/Chothia Composite CDR1, CDR2, and CDR3 amino acid sequences are provided as SEQ ID NOS:4-6, respectively. The light chain Kabat CDR1, CDR2, and CDR3 amino acid sequences are provided as SEQ ID NOS:8-10, respectively. Kabat numbering is used throughout.

The variable kappa (Vk) of 18G1 belongs to mouse Kabat subgroup 5 which corresponds to human Kabat subgroup 1 and variable heavy (Vh) to mouse Kabat subgroup 3d which corresponds to human Kabat subgroup 3 (Kabat et al, 1991, supra).

11 residue CDR-L1 belongs to canonical class 2; 7 residue CDR-L2 to class 1 and 9 residue CDR-L3 to class 1 in Vk (Martin & Thornton, supra). 12 residue CDR-H1 belongs to class 3; 16 residue CDR-H2 to class 1 (Martin & Thornton, supra). CDR-H3 has no canonical classes (Shirai, supra).

The residues at the interface between the Vk and Vh domains are the ones commonly found; therefore none of the interface residues is specifically targeted for back-mutation.

A search was made over the protein sequences in the PDB database (Deshpande, supra) to find structures, which would provide a rough structural model of 18G1. We used the crystal structure of antibody fab (pdb code 3CLE) Nishiama V, et al., Direct submission, 2008) for the Vk structure since it had reasonably good resolution (2.5 A) and overall sequence similarity to 18G1 Vk, retaining the same canonical structures for the loops. An antibody fab with pdb code 2ZUQ (Inaba K, et al., 2009; 28:779-791) was used for the Vh structure. It had good overall sequence similarity and reasonably good resolution (3.3 A). In addition, CDRs-H1 and H2 had the same canonical structures as 18G1 Vh. We used Bioluminate software to model a rough structure of 18G1. This software is licensed from Schrodinger Inc.

A search of the non-redundant protein sequence database from NCBI allowed selection of suitable human frameworks into which to graft the murine CDRs. For Vk, a human kappa light chain with NCBI accession code AAD39507.1 (GI: 5081723) (Van Den Brink E. N. et al., 2000, Blood 95, 558-563) was chosen. This has the same canonical classes for CDR-L1 and L2. It is a member of Kabat human kappa subgroup 2. For Vh, human Ig heavy chain AAX82494.1 (GI: 62421461) (Lundquist, R. et al, 2006 Infect. Immun. 74, 3222-3231) was chosen, again with the same canonical classes. It is a member of Kabat human heavy subgroup 1.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN, supra) Residues were changed to align with corresponding human germ line sequence, where possible, to enhance humanness.

18G1VH was aligned to human germ line sequence IGHV3-13*01 and 18G1VL was aligned against IGKV2D-29*02.

Two humanized heavy chain variable region variants and two humanized light chain variable region variants were constructed containing different permutations of substitutions (Hu6B3VHv1 and Hu18G1VHv2, (SEQ ID NOS:34-35, respectively) and Hu18G1VLv1 and Hu18G1VLv2 (SEQ ID NOS:38-39, respectively)) (FIGS. 13A-D and FIGS. 14A-D). The exemplary humanized Vh and Vk designs, with backmutations and other mutations based on selected human frameworks, are shown in Table 7. The gray-shaded areas in FIGS. 13A-D and FIGS. 14A-D indicate the CDRs as defined by Kabat/Chothia Composite SEQ ID NOS:35, 38, and 39 contain backmutations and other mutations as shown in Table 7. The amino acids at positions H1, H5, H13, H19, H40, H42, H44, H49, H77, H82a, H83, H84, H89, H93, and H108 in Hu18G1VHv1 and Hu18G1VHv2, and at positions L3, L10, L13, L15, L19, L20, L22, L42, L45, L60, L70, L77, L78, L80, L83, and L85 in Hu18G1VLv1 and Hu18G1VLv2, are listed in Table 8.

TABLE 7

$V_H$, $V_L$ Backmutations and Other Mutations for Humanized 18G1

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| Hu18G1VHv1 (SEQ ID NO: 34) | NCBI accession codeAAX82494.1 (SEQ ID NO: 33) | (none) |
| Hu18G1VHv2 (SEQ ID NO: 35) | NCBI accession code AAX82494.1 (SEQ ID NO: 33) | H1, H5, H13, H19, H40, H42, H44, H49, H77, H82a, H83, H84, H89, H93, H108 |
| Hu18G1VLv1 (SEQ ID NO: 38) | NCBI accession code AAD39507.1 (SEQ ID NO: 37) | L3, L10, L13, L15, L19, L20, L22, L42, L45, L70, L77, L78, L80, L85 |
| Hu18G1VLv2 (SEQ ID NO: 39) | NCBI accession code AAD39507.1 (SEQ ID NO: 37) | L3, L10, L13, L15, L19, L20, L22, L42, L60, L70, L77, L78, L80, L83, L85 |

TABLE 8

Kabat Numbering of Framework Residues (based on Kabat/Chothia Composite CDRs) for Backmutations and Other Mutations in Humanized 18G1 Antibodies

| Residue | AAX82494.1 (Heavy Chain) | AAD39507.1 (Light Chain) | Mouse 18G1 | Hu18G1VHv1 | Hu18G1VHv2 | Hu18G1VLv1 | Hu18G1VLv2 |
|---|---|---|---|---|---|---|---|
| L3 | | Q | V | | | V | V |
| L10 | | F | F | | | S | S |
| L13 | | A | T | | | V | V |
| L15 | | V | V | | | P | P |
| L19 | | V | V | | | A | A |
| L20 | | T | S | | | S | S |
| L22 | | T | T | | | S | S |
| L42 | | K | Q | | | Q | Q |
| L45 | | K | K | | | Q | K |
| L60 | | S | D | | | S | D |
| L70 | | E | D | | | D | D |
| L77 | | S | N | | | R | R |
| L78 | | L | V | | | V | V |
| L80 | | P | S | | | A | A |
| L83 | | F | L | | | F | L |
| L85 | | T | E | | | V | V |
| H1 | Q | | E | Q | E | | |
| H5 | Q | | V | Q | V | | |
| H13 | K | | K | K | Q | | |
| H19 | K | | K | K | R | | |
| H40 | T | | T | T | A | | |
| H42 | D | | E | D | G | | |
| H44 | R | | R | R | G | | |
| H49 | A | | A | A | S | | |
| H77 | T | | T | T | S | | |
| H82a | S | | R | S | N | | |
| H83 | K | | R | K | R | | |
| H84 | S | | S | S | A | | |
| H89 | M | | M | M | V | | |
| H93 | A | | V | A | V | | |
| H108 | M | | S | M | T | | |

An alignment of the murine 18G1 Vh sequence (SEQ ID NO:3) with the human acceptor sequence (AAX824494.1; SEQ ID NO:33, and the Hu18G1VHv1 and Hu18G1VHv2, (SEQ ID NOs:34 and 35, respectively), is shown in FIG. 9. The CDR regions as defined by Kabat/Chothia Composite are boxed. Positions at which canonical, vernier, or interface residues differ between mouse and human acceptor sequences are candidates for substitution. Examples of canonical/CDR interacting residues include Kabat residue H48 in FIGS. 13A-D. Examples of interface/packing (VH+ VL) residues include Kabat residues H35, H37, H39, H45, H47, H91, H93, H95, H101, and H103 in FIGS. 13A-D.

An alignment of the murine 18G1 Vk sequence (SEQ ID NO:36) with the human acceptor sequence (AAD39507.1; SEQ ID NO:37), and the Hu18G1VLv1 and Hu18G1VLv2 (SEQ ID NOs 38 and 39, respectively), is shown in FIG. 10. The CDR regions as defined by Kabat are boxed. Positions at which canonical, vernier, or interface residues differ between mouse and human acceptor sequences are candidates for substitution. Examples of interface/packing (VH+ VL) residues include Kabat residues L34, L36, L38, L44, L46, L87, L89, L91, L96, and L98 in FIGS. 14A-D.

The rationales for selection of the positions indicated in Tables 7 and 8 in the light chain variable region as candidates for substitution are as follows. Q3V; F10S; A13V; V15P; V19A; T20S; T22S; K42Q; K45Q; S60D; E70D; S77R; L78V; P80A; F83L, and T85V are germ-line aligning mutations or frequency based back mutations.

The rationales for selection of the positions indicated in Tables 7 and 8 in the heavy chain variable region as candidates for substitution are as follows.

Q1E is a stability enhancing mutation to mitigate pyroglutamate formation potential. (Liu, supra).

Q5V; K13Q; K19R; T40A; D42G; R44G; A49S; T77S; S82aN; K83R; S84A; M89V, A93V, and M108T are frequency based back-mutations or germ-line aligning mutations.

The designs based on these human frameworks were:

VARIABLE KAPPA
>hu18G1vk Version1
(SEQ ID NO: 38)
DIVMTQSPSSLSVSPGDRASISCKASQNVGTNVAWYQQKPGQAPQLLIYS

ASYRYSGVPSRFSGSGSGTDFTLTISRVQAEDFAVYYCQQYNSFPLTFGG

GTKLEIK

>hu18G1vk Version2
(SEQ ID NO: 39)
DIVMTQSPSSLSVSPGDRASISCKASQNVGTNVAWYQQKPGQAPKLLIYS

ASYRYSGVPDRFSGSGSGTDFTLTISRVQAEDLAVYYCQQYNSFPLTFGG

GTKLEIK

VARIABLE HEAVY
18G1vh Version 1
(SEQ ID NO: 34)
QVQLQESGGGLVKPGGSLKLSCAASGFTFSSYAMSWVRQTPDKRLEWVAG

ISSGDYYTYYPDTVKGRFTISRDNAKNTLYLQMSSLKSEDTAMYYCARGR

GNTGPRVGYWGQGTMVTVSS

```
>18G1vh Version 2
                                                       (SEQ ID NO: 35)
EVQLVESGGGLVQPGGSLRLSCAASGFTFSSYAMSWVRQAPGKGLEWVSG

ISSGDYYTYYPDTVKGRFTISRDNAKNSLYLQMNSLRAEDTAVYYCVRGR

GNTGPRVGYWGQGTTVTVSS
```

Example 7. Evaluation of Cardiovascular Tissue Arrays

Materials and Methods. Tissue microarrays of human vascular tissues (Catalog No. 401 4201), human right heart tissue myocardial hypertrophy II (Catalog No. 401 4103), human left heart tissue myocardial hypertrophy I (Catalog No. 401 4102) cardiovascular tissue microarray (Catalog No. 401 4101) were purchased from Provitro and a cardiovascular disease tissue array (Catalog No. CVD231 was purchased from US Biomax. Tissue microarray sections were immunoperoxidase labeled on a Leica Bond Rx using the Polymer Refine Detection Kit (DS980, Leica Biosystems, Buffalo Grove, Ill.). Briefly, slides were deparaffinized and quenched of endogenous peroxidases before incubating with primary mouse monoclonal antibodies to medin clone 18G1 (0.1 μg/mL), clone 6B3 (0.5 μg/mL), or a matched IgG2blk (0.5 μg/mL; Biolegend; San Diego, Calif.) for 1 hour in diluent buffer (5% (v/v) normal goat serum with 0.25% (v/v) Triton X-100 in 1×PBS). The slides were then incubated in an anti-mouse and anti-rabbit polymeric HRP-linker antibody-conjugate (8 minutes). Staining was visualized with diaminobenzidine (DAB) chromogen, which produced a brown precipitate. Slides were counterstained with hematoxylin and dehydrated through an ascending alcohol series and cleared in three changes of xylene and coverslipped. Reagent controls included performing the staining procedure on adjacent TMA slides with non-immune isotype control (IgG2b1k) primary antibodies. Whole slides were digitally imaged at 40× with a NanoZoomer 2.0HT slide scanner (Hamamatsu, Bridgewater, N.J.) fitted with an UPlanSApo 20×/0.75 objective (Olympus; Central Valley, Pa.).

Results. 6B3 showed strong staining of all aortic (normal, aneurysm, atheroma, atherosclerosis and hypertension) and diseased coronary artery and vena cava samples and some staining in smaller vessels in the heart and kidney.

18G1 staining was seen in normal and diseased aorta but at a lower intensity than was seen with 6B3.

18G1 stained necrotic areas of cardiac tissue and myocardial scar tissue after acute myocardial infarction; additional staining was observed in venin thrombosis and varaicose vein tissue.

In addition, 18G1 labeled a wide variety of granulation tissue derived from the groin, intestine, ovary, abdominal wall and stomach.

Differential patterns and degrees of staining by immunohistochemistry were seen with 6B3 and 18G1 in patient tissue samples. A comparison was made of the distribution of PRT6B3 versus PRT18G1 immunoreactivity detected in tissue samples from patients with Marfan syndrome (aorta), hypertension (aorta), atheroma (aorta), coronary artery disease, myocardial infarction and granulation tissue (stomach) by immunohistochemistry. The pattern and degree of staining seen in the aorta of patients with Marfan syndrome and in an atheroma was similar with both antibodies, although PRT6B3 immunoreactivity was more abundant. In contrast, PRT6B3 staining was prevalent in patients with hypertension and coronary artery disease, while PRT18G1 immunoreactivity was sparse or absent. Likewise, PRT18G1 was seen in heart after a myocardial infarction and in granulation tissues, but PRT6B3 staining was weak.

What is claimed is:

1. An isolated monoclonal antibody that specifically binds to medin, comprising three light chain CDRs and three heavy chain CDRs of monoclonal antibody 18G1, wherein 18G1 is a mouse antibody characterized by a heavy chain variable region having an amino acid sequence comprising SEQ ID NO: 3 and a light chain variable region having an amino acid sequence comprising SEQ ID NO: 36.

2. The antibody of claim 1, wherein the three heavy chain CDRs are as defined by Kabat/Chothia Composite (SEQ ID NOS: 4, 5 and 6) and the three light chain CDRs are as defined by Kabat/Chothia Composite (SEQ ID NOS: 8, 9 and 10).

3. The antibody of claim 1 that is 18G1 or a chimeric, veneered, or humanized form thereof.

4. The antibody of claim 1, wherein the antibody is a humanized antibody.

5. The antibody of claim 3, that is a humanized or chimeric 18G1 antibody that specifically binds to human medin, wherein 18G1 is a mouse antibody characterized by a mature heavy chain variable region of SEQ ID NO:3 and a mature light chain variable region of SEQ ID NO: 36.

6. The humanized antibody of claim 5 comprising a humanized mature heavy chain variable region comprising the three heavy chain CDRs of 18G1 and a humanized mature light chain variable region comprising the three light chain CDRs of 18G1.

7. The humanized antibody of claim 6, wherein the CDRs are of a definition selected from the group of Kabat, Chothia, Kabat/Chothia Composite, AbM and Contact.

8. The humanized antibody of claim 7 wherein the humanized mature heavy chain variable region comprises the three Kabat/Chothia Composite heavy chain CDRs of 18G1 (SEQ ID NOs: 4-6) and the humanized mature light chain variable region comprises the three Kabat/Chothia Composite light chain CDRs of 18G1 (SEQ ID NOs: 8-10).

9. The humanized antibody of claim 7 wherein the humanized mature heavy chain variable region comprises the three Kabat heavy chain CDRs of 18G1 (CDR-H1 residues 6-10 of SEQ ID NO:4; CDR-H2 SEQ ID NO: 5, CDR-H3 SEQ ID NO:6) and the humanized mature light chain variable region comprises the three Kabat light chain CDRs of 18G1 (SEQ ID NOs: 8-10).

10. The humanized antibody of claim 7 wherein the humanized mature heavy chain variable region comprises the three Chothia heavy chain CDRs of 18G1 (CDR-H1 residues 1-7 of SEQ ID NO:4; CDR-H2 residues 3-8 of SEQ ID NO: 5, CDR-H3 SEQ ID NO:6) and the humanized mature light chain variable region comprises the three Chothia light chain CDRs of 18G1 (SEQ ID NOs: 8-10).

11. The humanized antibody of claim 7 wherein the humanized mature heavy chain variable region comprises the three AbM heavy chain CDRs of 18G1 (CDR-H1 SEQ ID NO:4; CDR-H2 residues 1-10 of SEQ ID NO: 5, CDR-H3 SEQ ID NO:6) and the humanized mature light chain variable region comprises the three AbM light chain CDRs of 18G1 (SEQ ID NOs: 8-10).

12. The humanized antibody of claim 7 wherein the humanized mature heavy chain variable region comprises the three Contact heavy chain CDRs of 18G1 (CDR-H1 residues 30-35 of SEQ ID:3; CDR-H2 residues 47-59 of SEQ ID NO: 3, CDR-H3 residues 97-108 of SEQ ID NO:3) and the humanized mature light chain variable region comprises the three Contact light chain CDRs of 18G1 (CDR-L1 residues 30-36 of SEQ ID:36; CDR-L2 residues 46-55 of SEQ ID NO: 36, CDR-L3 residues 89-96 of SEQ ID NO:36).

13. The humanized antibody of claim 7 comprising a humanized mature heavy chain variable region having an amino acid sequence at least 90% identical to any one of SEQ ID NO:34-35 and a humanized mature light chain variable region having an amino acid sequence at least 90% identical to SEQ ID NO: 38-39.

14. The humanized antibody of claim 13, wherein at least one of the following positions is occupied by the amino acid as specified: position L3 is occupied by V, position L10 is occupied by S, position L13 is occupied by V, position L15 is occupied by P, position L19 is occupied by A, position L20 is occupied by S, position L22 is occupied by S, position L42 is occupied by Q, position L70 is occupied by D, position L77 is occupied by R, position L78 is occupied by V, position L80 is occupied by A, and position L85 is occupied by V.

15. The humanized antibody of claim 13, provided positions L3, L10, L13, L15, L19, L20, L22, L42, L70, L77, L78, L80, and L85 are occupied by V, S, V, P, A, S, S, Q, D, R, V, A, and V, respectively.

16. The humanized antibody of claim 13 or 14, wherein at least one of the following positions is occupied by the amino acid as specified: position H1 is occupied by E or Q, position H5 is occupied by V or Q, position H13 is occupied by Q or K, position H19 is occupied R or K, position H40 is occupied by A or T, position H42 is occupied by G or D, position H44 is occupied G or R, position H49 is occupied by S or A, position H77 is occupied by S or T, position H82a is occupied by N or S, position H83 is occupied by R or K, position H84 is occupied by A or S, position H89 is occupied by V or M, H93 is occupied by V or A, and position H108 is occupied by T or M.

17. The humanized antibody of claim 16, provided positions H1, H5, H13, H19, H40, H42, H44, H49, H77, H82a, H83, H84, H89, H93, and H108 are occupied by, E, V, Q, R, A, G, G, S, S, N, R, A, V, V, and T, respectively.

18. The humanized antibody of claim 13, comprising a mature heavy chain variable region having an amino acid sequence at least 95% identical to any one of SEQ ID NO: 34-35 and a mature light chain variable region having an amino acid sequence at least 95% identical to any one of SEQ ID NO: 38-39.

19. The humanized antibody of claim 18, comprising a mature heavy chain variable region having an amino acid sequence at least 98% identical to any one of SEQ ID NO: 34-35 and a mature light chain variable region having an amino acid sequence at least 98% identical to any one of SEQ ID NO: 38-39.

20. The humanized antibody of claim 19 wherein the mature heavy chain variable region has the amino acid sequence of any of SEQ ID NO:34-35 and the mature light chain variable region has the amino acid sequence of any one of SEQ ID NO:38-39.

21. The humanized antibody of claim 20, wherein the mature heavy chain variable region has the amino acid sequence of SEQ ID NO:35 and the mature light chain variable region has the amino acid sequence of SEQ ID NO:39.

22. The antibody of claim 1 that is an intact antibody.

23. The antibody of claim 1, that is a single-chain antibody, Fab, or Fab'2 fragment.

24. The antibody of claim 5, wherein the isotype is human IgG1.

25. The humanized antibody of claim 24, wherein the mature light chain variable region is fused to a light chain constant region and the mature heavy chain variable region is fused to a heavy chain constant region.

26. The humanized antibody of claim 25, wherein the heavy chain constant region is a mutant form of a natural human heavy chain constant region which has reduced binding to a Fcγ receptor relative to the natural human heavy chain constant region.

27. The antibody of claim 25, having at least one mutation in the constant region.

28. The antibody of claim 27, wherein the mutation reduces complement fixation or activation by the constant region.

29. The antibody of claim 1, wherein the antibody is conjugated to a therapeutic or cytotoxic agent.

30. A pharmaceutical composition comprising an antibody as defined in claim 1 and a pharmaceutically-acceptable carrier.

31. The humanized antibody of claim 15, wherein at least one of the following positions is occupied by the amino acid as specified: L45 is occupied by Q, L60 is occupied by D, and L83 is occupied by L.

32. The humanized antibody of claim 31, provided positions L45, L60 and L83 are occupied by Q, D and L, respectively.

33. The humanized antibody of claim 16, wherein positions L3, L10, L13, L15, L19, L20, L22, L42, L70, L77, L78, L80, and L85 are occupied by V, S, V, P, A, S, S, Q, D, R, V, A, and V, respectively.

* * * * *

SEQUENCE LISTING

```
<160> NUMBER OF SEQ ID NOS: 39

<210> SEQ ID NO 1
<211> LENGTH: 50
<212> TYPE: PRT
<213> ORGANISM: Homo sapiens

<400> SEQUENCE: 1

Arg Leu Asp Lys Gln Gly Asn Phe Asn Ala Trp Val Ala Gly Ser Tyr
1               5                   10                  15

Gly Asn Asp Gln Trp Leu Gln Val Asp Leu Gly Ser Ser Lys Glu Val
            20                  25                  30

Thr Gly Ile Ile Thr Gln Gly Ala Arg Asn Phe Gly Ser Val Gln Phe
        35                  40                  45

Val Ala
    50

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Cys Gly Gly Ser Val Gln Phe Val Ala
1               5
```

<210> SEQ ID NO 3
<211> LENGTH: 120
<212> TYPE: PRT
<213> ORGANISM: Artificial Sequence
<220> FEATURE:
<223> OTHER INFORMATION: Synthesized

<400> SEQUENCE: 3

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Gly Ile Ser Ser Gly Asp Tyr Tyr Thr Tyr Tyr Pro Asp Thr Val
    50                  55                  60

Lys Gly Arg Phe Thr Ile Ser Arg Asp Asn Ala Arg Asn Thr Leu Tyr
65                  70                  75                  80

Leu Gln Met Arg Ser Leu Arg Ser Glu Asp Thr Ala Met Tyr Tyr Cys
                85                  90                  95

Val Arg Gly Arg Gly Asn Thr Gly Pro Arg Val Gly Tyr Trp Gly Gln
            100                 105                 110

Gly Thr Ser Val Thr Val Ser Ser
        115                 120
```

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

```
Gly Phe Thr Phe Ser Ser Tyr Ala Met Ser
1               5                   10
```

<210> SEQ ID NO 5
<211> LENGTH: 17
<212> TYPE: PRT
<213> ORGANISM: Artificial Sequence
<220> FEATURE:
<223> OTHER INFORMATION: Synthesized

<400> SEQUENCE: 5

```
Gly Ile Ser Ser Gly Asp Tyr Tyr Thr Tyr Tyr Pro Asp Thr Val Lys
1               5                   10                  15

Gly
```

<210> SEQ ID NO 6
<211> LENGTH: 11
<212> TYPE: PRT
<213> ORGANISM: Artificial Sequence
<220> FEATURE:
<223> OTHER INFORMATION: Synthesized

<400> SEQUENCE: 6

```
Gly Arg Gly Asn Thr Gly Pro Arg Val Gly Tyr
1               5                   10
```

<210> SEQ ID NO 7
<211> LENGTH: 108

```
<212> TYPE: PRT
<213> ORGANISM: Artificial Sequence
<220> FEATURE:
<223> OTHER INFORMATION: Synthesized

<400> SEQUENCE: 7

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Phe Pro Leu
                85                  90                  95

Thr Phe Gly Ala Gly Thr Lys Leu Glu Leu Lys Arg
            100                 105

<210> SEQ ID NO 8
<211> LENGTH: 11
<212> TYPE: PRT
<213> ORGANISM: Artificial Sequence
<220> FEATURE:
<223> OTHER INFORMATION: Synthesized

<400> SEQUENCE: 8

Lys Ala Ser Gln Asn Val Gly Thr Asn Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthesized

<400> SEQUENCE: 9

Ser Ala Ser Tyr Arg Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

Gln Gln Tyr Asn Ser Phe Pro Leu Thr
1               5

<210> SEQ ID NO 11
<211> LENGTH: 118
<212> TYPE: PRT
<213> ORGANISM: Artificial Sequence
<220> FEATURE:
<223> OTHER INFORMATION: Synthesized

<400> SEQUENCE: 11

Gln Val Thr Leu Lys Glu Ser Gly Pro Gly Ile Leu Gln Pro Ser Gln
1               5                   10                  15
```

```
Thr Leu Ser Leu Thr Cys Ser Phe Ser Gly Phe Ser Leu Ser Thr Ser
            20                  25                  30

Asp Met Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Ile Ala
    50                  55                  60

Leu Lys Asn Arg Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Leu Val Gly Ser Trp Phe Ala Tyr Trp Gly Gln Gly Thr
            100                 105                 110

Leu Val Thr Val Ser Ala
        115

<210> SEQ ID NO 12
<211> LENGTH: 12
<212> TYPE: PRT
<213> ORGANISM: Artificial Sequence
<220> FEATURE:
<223> OTHER INFORMATION: Synthesized

<400> SEQUENCE: 12

Gly Phe Ser Leu Ser Thr Ser Asp Met Gly Val Gly
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthesized

<400> SEQUENCE: 13

His Ile Trp Trp Asn Asp Asn Lys Tyr Tyr Asn Ile Ala Leu Lys Asn
1               5                   10                  15

<210> SEQ ID NO 14
<211> LENGTH: 8
<212> TYPE: PRT
<213> ORGANISM: Artificial Sequence
<220> FEATURE:
<223> OTHER INFORMATION: Synthesized

<400> SEQUENCE: 14

Leu Val Gly Ser Trp Phe Ala Tyr
1               5

<210> SEQ ID NO 15
<211> LENGTH: 108
<212> TYPE: PRT
<213> ORGANISM: Artificial Sequence
<220> FEATURE:
<223> OTHER INFORMATION: Synthesized

<400> SEQUENCE: 15

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Ser Trp Tyr His Gln Lys Pro Asp Gly Thr Val Lys Leu Leu Ile
        35                  40                  45
```

```
Tyr Tyr Thr Ser Arg Leu His Ser Gly Val Pro Pro Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Lys Thr Leu Pro Pro
                 85                  90                  95

Thr Phe Gly Gly Gly Thr Lys Leu Glu Ile Lys Arg
            100                 105
```

<210> SEQ ID NO 16
<211> LENGTH: 11
<212> TYPE: PRT
<213> ORGANISM: Artificial Sequence
<220> FEATURE:
<223> OTHER INFORMATION: Synthesized

<400> SEQUENCE: 16

```
Arg Ala Ser Gln Asp Ile Ser Asn Phe Leu Ser
 1               5                  10
```

<210> SEQ ID NO 17
<211> LENGTH: 7
<212> TYPE: PRT
<213> ORGANISM: Artificial Sequence
<220> FEATURE:
<223> OTHER INFORMATION: Synthesized

<400> SEQUENCE: 17

```
Tyr Thr Ser Arg Leu His Ser
 1               5
```

<210> SEQ ID NO 18
<211> LENGTH: 9
<212> TYPE: PRT
<213> ORGANISM: Artificial Sequence
<220> FEATURE:
<223> OTHER INFORMATION: Synthesized

<400> SEQUENCE: 18

```
Gln Gln Gly Lys Thr Leu Pro Pro Thr
 1               5
```

<210> SEQ ID NO 19
<211> LENGTH: 40
<212> TYPE: DNA
<213> ORGANISM: Artificial Sequence
<220> FEATURE:
<223> OTHER INFORMATION: Synthesized

<400> SEQUENCE: 19
actagtcgac atgaagttgc ctgttaggct gttggtgctg                    40

<210> SEQ ID NO 20
<211> LENGTH: 27
<212> TYPE: DNA
<213> ORGANISM: Artificial Sequence
<220> FEATURE:
<223> OTHER INFORMATION: Synthesized

<400> SEQUENCE: 20
ggatcccggg agtggataga ccgatgg                                  27

<210> SEQ ID NO 21
<211> LENGTH: 27

<212> TYPE: DNA
<213> ORGANISM: Artificial Sequence
<220> FEATURE:
<223> OTHER INFORMATION: Synthesized

<400> SEQUENCE: 21
ggatcccggg agtggataga ctgatgg                                          27

<210> SEQ ID NO 22
<211> LENGTH: 9
<212> TYPE: PRT
<213> ORGANISM: Artificial Sequence
<220> FEATURE:
<223> OTHER INFORMATION: Synthesized

<400> SEQUENCE: 22

Cys Gly Gly His Ile Gln Tyr Val Ala
1               5

<210> SEQ ID NO 23
<211> LENGTH: 122
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (1)..(1)
<223> OTHER INFORMATION: Xaa = Non-consensus amino acid
<220> FEATURE:
<221> NAME/KEY: VARIANT
<222> LOCATION: (3)..(3)
<223> OTHER INFORMATION: Xaa = Non-consensus amino acid
<220> FEATURE:
<221> NAME/KEY: VARIANT
<222> LOCATION: (5)..(5)
<223> OTHER INFORMATION: Xaa = Non-consensus amino acid
<220> FEATURE:
<221> NAME/KEY: VARIANT
<222> LOCATION: (9)..(9)
<223> OTHER INFORMATION: Xaa = Non-consensus amino acid
<220> FEATURE:
<221> NAME/KEY: VARIANT
<222> LOCATION: (11)..(13)
<223> OTHER INFORMATION: Xaa = Non-consensus amino acid
<220> FEATURE:
<221> NAME/KEY: VARIANT
<222> LOCATION: (15)..(17)
<223> OTHER INFORMATION: Xaa = Non-consensus amino acid
<220> FEATURE:
<221> NAME/KEY: VARIANT
<222> LOCATION: (19)..(19)
<223> OTHER INFORMATION: Xaa = Non-consensus amino acid
<220> FEATURE:
<221> NAME/KEY: VARIANT
<222> LOCATION: (21)..(21)
<223> OTHER INFORMATION: Xaa = Non-consensus amino acid
<220> FEATURE:
<221> NAME/KEY: VARIANT
<222> LOCATION: (23)..(24)
<223> OTHER INFORMATION: Xaa = Non-consensus amino acid
<220> FEATURE:
<221> NAME/KEY: VARIANT
<222> LOCATION: (28)..(29)
<223> OTHER INFORMATION: Xaa = Non-consensus amino acid
<220> FEATURE:
<221> NAME/KEY: VARIANT
<222> LOCATION: (31)..(33)
<223> OTHER INFORMATION: Xaa = Non-consensus amino acid
<220> FEATURE:
<221> NAME/KEY: VARIANT
<222> LOCATION: (35)..(37)
<223> OTHER INFORMATION: Xaa = Non-consensus amino acid
<220> FEATURE:
<221> NAME/KEY: VARIANT

```
<222> LOCATION: (39)..(39)
<223> OTHER INFORMATION: Xaa = Non-consensus amino acid
<220> FEATURE:
<221> NAME/KEY: VARIANT
<222> LOCATION: (42)..(44)
<223> OTHER INFORMATION: Xaa = Non-consensus amino acid
<220> FEATURE:
<221> NAME/KEY: VARIANT
<222> LOCATION: (46)..(46)
<223> OTHER INFORMATION: Xaa = Non-consensus amino acid
<220> FEATURE:
<221> NAME/KEY: VARIANT
<222> LOCATION: (50)..(50)
<223> OTHER INFORMATION: Xaa = Non-consensus amino acid
<220> FEATURE:
<221> NAME/KEY: VARIANT
<222> LOCATION: (52)..(52)
<223> OTHER INFORMATION: Xaa = Non-consensus amino acid
<220> FEATURE:
<221> NAME/KEY: VARIANT
<222> LOCATION: (54)..(56)
<223> OTHER INFORMATION: Xaa = Non-consensus amino acid
<220> FEATURE:
<221> NAME/KEY: VARIANT
<222> LOCATION: (58)..(60)
<223> OTHER INFORMATION: Xaa = Non-consensus amino acid
<220> FEATURE:
<221> NAME/KEY: VARIANT
<222> LOCATION: (63)..(66)
<223> OTHER INFORMATION: Xaa = Non-consensus amino acid
<220> FEATURE:
<221> NAME/KEY: VARIANT
<222> LOCATION: (68)..(68)
<223> OTHER INFORMATION: Xaa = Non-consensus amino acid
<220> FEATURE:
<221> NAME/KEY: VARIANT
<222> LOCATION: (70)..(70)
<223> OTHER INFORMATION: Xaa = Non-consensus amino acid
<220> FEATURE:
<221> NAME/KEY: VARIANT
<222> LOCATION: (72)..(72)
<223> OTHER INFORMATION: Xaa = Non-consensus amino acid
<220> FEATURE:
<221> NAME/KEY: VARIANT
<222> LOCATION: (74)..(74)
<223> OTHER INFORMATION: Xaa = Non-consensus amino acid
<220> FEATURE:
<221> NAME/KEY: VARIANT
<222> LOCATION: (76)..(78)
<223> OTHER INFORMATION: Xaa = Non-consensus amino acid
<220> FEATURE:
<221> NAME/KEY: VARIANT
<222> LOCATION: (80)..(82)
<223> OTHER INFORMATION: Xaa = Non-consensus amino acid
<220> FEATURE:
<221> NAME/KEY: VARIANT
<222> LOCATION: (84)..(86)
<223> OTHER INFORMATION: Xaa = Non-consensus amino acid
<220> FEATURE:
<221> NAME/KEY: VARIANT
<222> LOCATION: (88)..(91)
<223> OTHER INFORMATION: Xaa = Non-consensus amino acid
<220> FEATURE:
<221> NAME/KEY: VARIANT
<222> LOCATION: (95)..(95)
<223> OTHER INFORMATION: Xaa = Non-consensus amino acid
<220> FEATURE:
<221> NAME/KEY: VARIANT
<222> LOCATION: (99)..(99)
<223> OTHER INFORMATION: Xaa = Non-consensus amino acid
<220> FEATURE:
<221> NAME/KEY: VARIANT
<222> LOCATION: (101)..(105)
<223> OTHER INFORMATION: Xaa = Non-consensus amino acid
<220> FEATURE:
<221> NAME/KEY: VARIANT
<222> LOCATION: (107)..(110)
<223> OTHER INFORMATION: Xaa = Non-consensus amino acid
<220> FEATURE:
```

<221> NAME/KEY: VARIANT
<222> LOCATION: (117)..(117)
<223> OTHER INFORMATION: Xaa = Non-consensus amino acid
<220> FEATURE:
<221> NAME/KEY: VARIANT
<222> LOCATION: (122)..(122)
<223> OTHER INFORMATION: Xaa = Non-consensus amino acid

<400> SEQUENCE: 23

Xaa Val Xaa Leu Xaa Glu Ser Gly Xaa Gly Xaa Xaa Xaa Pro Xaa Xaa
 1               5                  10                  15

Xaa Leu Xaa Leu Xaa Cys Xaa Xaa Ser Gly Phe Xaa Xaa Ser Xaa Xaa
            20                  25                  30

Xaa Met Xaa Xaa Xaa Trp Xaa Arg Gln Xaa Xaa Xaa Lys Xaa Leu Glu
        35                  40                  45

Trp Xaa Ala Xaa Ile Xaa Xaa Xaa Asp Xaa Xaa Xaa Tyr Tyr Xaa Xaa
    50                  55                  60

Xaa Xaa Lys Xaa Arg Xaa Thr Xaa Ser Xaa Asp Xaa Xaa Xaa Asn Xaa
65                  70                  75                  80

Xaa Xaa Leu Xaa Xaa Xaa Ser Xaa Xaa Xaa Xaa Asp Thr Ala Xaa Tyr
                85                  90                  95

Tyr Cys Xaa Arg Xaa Xaa Xaa Xaa Xaa Gly Xaa Xaa Xaa Xaa Tyr Trp
            100                 105                 110

Gly Gln Gly Thr Xaa Val Thr Val Ser Xaa
        115                 120

<210> SEQ ID NO 24
<211> LENGTH: 108
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (3)..(3)
<223> OTHER INFORMATION: Xaa = Non-consensus amino acid
<220> FEATURE:
<221> NAME/KEY: VARIANT
<222> LOCATION: (7)..(11)
<223> OTHER INFORMATION: Xaa = Non-consensus amino acid
<220> FEATURE:
<221> NAME/KEY: VARIANT
<222> LOCATION: (13)..(13)
<223> OTHER INFORMATION: Xaa = Non-consensus amino acid
<220> FEATURE:
<221> NAME/KEY: VARIANT
<222> LOCATION: (15)..(15)
<223> OTHER INFORMATION: Xaa = Non-consensus amino acid
<220> FEATURE:
<221> NAME/KEY: VARIANT
<222> LOCATION: (20)..(22)
<223> OTHER INFORMATION: Xaa = Non-consensus amino acid
<220> FEATURE:
<221> NAME/KEY: VARIANT
<222> LOCATION: (24)..(24)
<223> OTHER INFORMATION: Xaa = Non-consensus amino acid
<220> FEATURE:
<221> NAME/KEY: VARIANT
<222> LOCATION: (28)..(34)
<223> OTHER INFORMATION: Xaa = Non-consensus amino acid
<220> FEATURE:
<221> NAME/KEY: VARIANT
<222> LOCATION: (37)..(37)
<223> OTHER INFORMATION: Xaa = Non-consensus amino acid
<220> FEATURE:
<221> NAME/KEY: VARIANT
<222> LOCATION: (41)..(44)
<223> OTHER INFORMATION: Xaa = Non-consensus amino acid
<220> FEATURE:
<221> NAME/KEY: VARIANT

```
<222> LOCATION: (46)..(46)
<223> OTHER INFORMATION: Xaa = Non-consensus amino acid
<220> FEATURE:
<221> NAME/KEY: VARIANT
<222> LOCATION: (50)..(51)
<223> OTHER INFORMATION: Xaa = Non-consensus amino acid
<220> FEATURE:
<221> NAME/KEY: VARIANT
<222> LOCATION: (53)..(55)
<223> OTHER INFORMATION: Xaa = Non-consensus amino acid
<220> FEATURE:
<221> NAME/KEY: VARIANT
<222> LOCATION: (60)..(60)
<223> OTHER INFORMATION: Xaa = Non-consensus amino acid
<220> FEATURE:
<221> NAME/KEY: VARIANT
<222> LOCATION: (63)..(63)
<223> OTHER INFORMATION: Xaa = Non-consensus amino acid
<220> FEATURE:
<221> NAME/KEY: VARIANT
<222> LOCATION: (71)..(72)
<223> OTHER INFORMATION: Xaa = Non-consensus amino acid
<220> FEATURE:
<221> NAME/KEY: VARIANT
<222> LOCATION: (78)..(80)
<223> OTHER INFORMATION: Xaa = Non-consensus amino acid
<220> FEATURE:
<221> NAME/KEY: VARIANT
<222> LOCATION: (83)..(83)
<223> OTHER INFORMATION: Xaa = Non-consensus amino acid
<220> FEATURE:
<221> NAME/KEY: VARIANT
<222> LOCATION: (85)..(85)
<223> OTHER INFORMATION: Xaa = Non-consensus amino acid
<220> FEATURE:
<221> NAME/KEY: VARIANT
<222> LOCATION: (91)..(94)
<223> OTHER INFORMATION: Xaa = Non-consensus amino acid
<220> FEATURE:
<221> NAME/KEY: VARIANT
<222> LOCATION: (96)..(96)
<223> OTHER INFORMATION: Xaa = Non-consensus amino acid
<220> FEATURE:
<221> NAME/KEY: VARIANT
<222> LOCATION: (100)..(100)
<223> OTHER INFORMATION: Xaa = Non-consensus amino acid
<220> FEATURE:
<221> NAME/KEY: VARIANT
<222> LOCATION: (106)..(106)
<223> OTHER INFORMATION: Xaa = Non-consensus amino acid

<400> SEQUENCE: 24

Asp Ile Xaa Met Thr Gln Xaa Xaa Xaa Xaa Xaa Ser Xaa Ser Xaa Gly
1               5                   10                  15

Asp Arg Val Xaa Xaa Xaa Cys Xaa Ala Ser Gln Xaa Xaa Xaa Xaa Xaa
            20                  25                  30

Xaa Xaa Trp Tyr Xaa Gln Lys Pro Xaa Xaa Xaa Xaa Lys Xaa Leu Ile
        35                  40                  45

Tyr Xaa Xaa Ser Xaa Xaa Xaa Ser Gly Val Pro Xaa Arg Phe Xaa Gly
    50                  55                  60

Ser Gly Ser Gly Thr Asp Xaa Xaa Leu Thr Ile Ser Asn Xaa Xaa Xaa
65                  70                  75                  80

Glu Asp Xaa Ala Xaa Tyr Phe Cys Gln Gln Xaa Xaa Xaa Xaa Pro Xaa
                85                  90                  95

Thr Phe Gly Xaa Gly Thr Lys Leu Glu Xaa Lys Arg
                100                 105

<210> SEQ ID NO 25
<211> LENGTH: 119
<212> TYPE: PRT
<213> ORGANISM: Artificial Sequence
```

```
<220> FEATURE:
<223> OTHER INFORMATION: Synthesized

<400> SEQUENCE: 25

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Met Met Gly Asn Trp Phe Asp Pro Trp Gly Gln Gly
            100                 105                 110

Thr Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Synthesized

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Phe Ser Gly Phe Ser Leu Ser Thr Ser
            20                  25                  30

Asp Met Gly Val Gly Trp Ile Arg Gln Pro Pro Gly Lys Ala Leu Glu
        35                  40                  45

Trp Leu Ala His Ile Trp Trp Asn Asp Asn Lys Tyr Tyr Asn Ile Ala
    50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Val Gly Ser Trp Phe Ala Tyr Trp Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Synthesized

<400> SEQUENCE: 27

Glu Val Gln Leu Gln Glu Ser Gly Pro Gly Leu Val Lys Pro Ser Gln
1               5                   10                  15

Thr Leu Ser Leu Thr Cys Thr Phe Ser Gly Phe Ser Leu Ser Thr Ser
            20                  25                  30
```

Asp Met Gly Val Gly Trp Ile Arg Gln Pro Pro Gly Lys Gly Leu Glu
            35                  40                  45

Trp Leu Ala His Ile Trp Asn Asp Asn Lys Tyr Tyr Asn Ile Ala
 50                  55                  60

Leu Lys Asn Arg Leu Thr Ile Ser Lys Asp Thr Ser Lys Asn Gln Val
 65                  70                  75                  80

Ser Leu Lys Leu Thr Ser Val Thr Ala Ala Asp Thr Ala Val Tyr Tyr
                 85                  90                  95

Cys Ala Arg Leu Val Gly Ser Trp Phe Ala Tyr Trp Gly Gln Gly Thr
                100                 105                 110

Leu Val Thr Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: Synthesized

<400> SEQUENCE: 28

Glu Val Gln Leu Gln Glu Ser Gly Pro Gly Leu Val Lys Pro Ser Gln
 1               5                  10                  15

Thr Leu Ser Leu Thr Cys Thr Phe Ser Gly Phe Ser Leu Ser Thr Ser
                 20                  25                  30

Asp Met Gly Val Gly Trp Ile Arg Gln Pro Pro Gly Lys Gly Leu Glu
            35                  40                  45

Trp Ile Gly His Ile Trp Trp Asn Asp Asn Lys Tyr Tyr Asn Ile Ala
 50                  55                  60

Leu Lys Asn Arg Val Thr Ile Ser Lys Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu Val Gly Ser Trp Phe Ala Tyr Trp Gly Gln Gly Thr
                100                 105                 110

Thr Val Thr Val Ser Ser
        115

<210> SEQ ID NO 29
<211> LENGTH: 107
<212> TYPE: PRT
<213> ORGANISM: Artificial Sequence
<220> FEATURE:
<223> OTHER INFORMATION: Synthesized

<400> SEQUENCE: 29

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Phe
                 20                  25                  30

Leu Ser Trp Tyr His Gln Lys Pro Asp Gly Thr Val Lys Leu Leu Ile
            35                  40                  45

Tyr Tyr Thr Ser Arg Leu His Ser Gly Val Pro Pro Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Lys Thr Leu Pro Pro
                 85                  90                  95

Thr Phe Gly Gly Gly Thr Lys Leu Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Synthesized

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gly Gly Thr Lys Val Glu Ile Lys
            100                 105

<210> SEQ ID NO 31
<211> LENGTH: 107
<212> TYPE: PRT
<213> ORGANISM: Artificial Sequence
<220> FEATURE:
<223> OTHER INFORMATION: Synthesized

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Ser Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Lys Thr Leu Pro Pro
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthesized

<400> SEQUENCE: 32

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Ser Asn Phe
            20                  25                  30

Leu Ser Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Lys Thr Leu Pro Pro
                85                  90                  95

Thr Phe Gly Gln Gly Thr Lys Leu Glu Ile Lys
            100                 105

<210> SEQ ID NO 33
<211> LENGTH: 120
<212> TYPE: PRT
<213> ORGANISM: Artificial Sequence
<220> FEATURE:
<223> OTHER INFORMATION: Synthesized

<400> SEQUENCE: 33

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: Synthesized

<400> SEQUENCE: 34

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Asp Lys Arg Leu Glu Trp Val
        35                  40                  45

Ala Gly Ile Ser Ser Gly Asp Tyr Tyr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95
```

```
Ala Arg Gly Arg Gly Asn Thr Gly Pro Arg Val Gly Tyr Trp Gly Gln
            100                 105                 110

Gly Thr Met Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: Synthesized

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Asp Tyr Tyr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Arg Gly Asn Thr Gly Pro Arg Val Gly Tyr Trp Gly Gln
            100                 105                 110

Gly Thr Thr Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Synthesized

<400> SEQUENCE: 36

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Phe Pro Leu
                85                  90                  95

Thr Phe Gly Ala Gly Thr Lys Leu Glu Leu Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthesized
```

<400> SEQUENCE: 37

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln His Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Leu Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Synthesized

<400> SEQUENCE: 38

Asp Ile Val Met Thr Gln Ser Pro Ser Ser Leu Ser Val Ser Pro Gly
1               5                   10                  15

Asp Arg Ala Ser Ile Ser Cys Lys Ala Ser Gln Asn Val Gly Thr Asn
            20                  25                  30

Val Ala Trp Tyr Gln Gln Lys Pro Gly Gln Ala Pro Gln Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Arg Val Gln Ala
65                  70                  75                  80

Glu Asp Phe Ala Val Tyr Tyr Cys Gln Gln Tyr Asn Ser Phe Pro Leu
                85                  90                  95

Thr Phe Gly Gly Gly Thr Lys Leu Glu Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: Synthesized

<400> SEQUENCE: 39

Asp Ile Val Met Thr Gln Ser Pro Ser Ser Leu Ser Val Ser Pro Gly
1               5                   10                  15

Asp Arg Ala Ser Ile Ser Cys Lys Ala Ser Gln Asn Val Gly Thr Asn
            20                  25                  30

Val Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Arg Val Gln Ala
65                  70                  75                  80

```
Glu Asp Leu Ala Val Tyr Tyr Cys Gln Gln Tyr Asn Ser Phe Pro Leu
                85                  90                  95

Thr Phe Gly Gly Gly Thr Lys Leu Glu Ile Lys
            100                 105
```